United States Patent
Bornstein et al.

(10) Patent No.: US 8,983,257 B2
(45) Date of Patent: Mar. 17, 2015

(54) THERAPEUTIC LIGHT DELIVERY APPARATUS, METHOD, AND SYSTEM

(75) Inventors: Eric Bornstein, Woodmere, NY (US); Edward Sinofsky, Dennis, MA (US)

(73) Assignee: Nomir Medical Technologies, Inc., Woodmere, NY (US)

(*) Notice: Subject to any disclaimer, the term of this patent is extended or adjusted under 35 U.S.C. 154(b) by 0 days.

(21) Appl. No.: 13/474,320

(22) Filed: May 17, 2012

(65) Prior Publication Data

US 2012/0319010 A1 Dec. 20, 2012

Related U.S. Application Data

(63) Continuation of application No. 13/246,447, filed on Sep. 27, 2011, now abandoned, which is a continuation of application No. 13/058,765, filed as application No. PCT/US2009/053752 on Aug. 13, 2009, now abandoned, said application No. 13/058,765 is a continuation-in-part of application No. 11/981,486, filed on Oct. 31, 2007, now abandoned, and a continuation-in-part of application No. 10/776,106, filed on Feb. 11, 2004, now abandoned, and a continuation-in-part of application No. PCT/US2006/028616, filed on Jul. 21, 2006, said application No. 11/981,486 is a continuation-in-part of application No. PCT/US2006/030434, filed on Aug. 3, 2006, said application No. 13/058,765 is a continuation-in-part of application No. 11/930,941, filed on Oct. 31, 2007, now Pat. No. 7,713,294, which is a continuation-in-part of application No. PCT/US2006/028616, filed on Jul. 21, 2006, and a continuation of application No. PCT/US2006/030434, filed on Aug. 3, 2006, and a continuation-in-part of application No. 10/776,106, filed on Feb. 11, 2004, now abandoned, which is a continuation-in-part of application No. 10/649,910, filed on Aug. 26, 2003, now abandoned.

(60) Provisional application No. 61/088,401, filed on Aug. 13, 2008, provisional application No. 60/874,424, filed on Dec. 12, 2006, provisional application No. 60/701,896, filed on Jul. 21, 2005, provisional application No. 60/711,091, filed on Aug. 23, 2005, provisional application No. 60/780,998, filed on Mar. 9, 2006, provisional application No. 60/789,090, filed on Apr. 4, 2006, provisional application No. 60/705,630, filed on Aug. 3, 2005, provisional application No. 60/406,493, filed on Aug. 28, 2002.

(51) Int. Cl.
*G02B 6/00* (2006.01)
*A61B 1/07* (2006.01)
*A61B 18/22* (2006.01)
*A61N 5/06* (2006.01)
*A61N 5/067* (2006.01)

(52) U.S. Cl.
CPC ......... *A61N 5/062* (2013.01); *A61N 2005/0659* (2013.01); *A61N 2005/067* (2013.01); *A61N 2005/063* (2013.01)
USPC ............... 385/117; 385/35; 385/38; 600/129; 606/15

(58) Field of Classification Search
CPC ............... A61B 2018/2261; A61B 2018/2266; A61B 2018/2272; G02B 6/3624
USPC .......................................................... 385/35
See application file for complete search history.

(56) References Cited

U.S. PATENT DOCUMENTS

| | | | | |
|---|---|---|---|---|
| 3,809,072 | A * | 5/1974 | Ersek et al. | 600/249 |
| 4,498,481 | A * | 2/1985 | Lemke | 600/547 |
| 4,852,567 | A * | 8/1989 | Sinofsky | 606/3 |
| 5,151,096 | A * | 9/1992 | Khoury | 606/15 |
| 5,403,308 | A * | 4/1995 | Wood et al. | 606/17 |
| 5,509,917 | A * | 4/1996 | Cecchetti et al. | 606/15 |
| 5,637,877 | A * | 6/1997 | Sinofsky | 250/492.1 |
| 5,784,508 | A * | 7/1998 | Turner | 385/31 |
| 6,270,492 | B1 * | 8/2001 | Sinofsky | 606/15 |
| 7,609,927 | B2 * | 10/2009 | Gowda et al. | 385/117 |
| 8,393,804 | B2 * | 3/2013 | Nielson et al. | 385/79 |
| 2003/0123825 | A1 * | 7/2003 | Sanso | 385/117 |
| 2003/0219202 | A1 * | 11/2003 | Loeb et al. | 385/33 |
| 2009/0210038 | A1 * | 8/2009 | Neuberger et al. | 607/89 |
| 2009/0287199 | A1 * | 11/2009 | Hanley et al. | 606/15 |

*Primary Examiner* — Michelle R Connelly

(74) *Attorney, Agent, or Firm* — The Marbury Law Group, PLLC

(57) ABSTRACT

An optical delivery apparatus is disclosed including: an optical fiber extending between a distal end having a distal end face and a proximal end having a proximal end face, an optical element positioned to receive the light emitted from the distal end face and direct the light to an illumination region; and a non-metallic housing containing the optical fiber and the optical element and maintaining the relative position of the optical fiber and the optical element.

20 Claims, 35 Drawing Sheets

PHOSPHOLIPID BILAYER

PHOSOPHOLIPID

Δψ-STEADY-BACT, Δψ-STEADY-MITO-MAM, AND
Δψ-STEADY-MITO-FUNGI PRIOR TO NIMELS IRRADIATION

Δψ-TRANS-BACT, Δψ-TRANS-MITO-MAM AND
Δψ-TRANS-MITO-FUNGI DURING AND AFTER NIMELS
IRRADIATION.

TRANS-MEMBRANE PROTEINS

DETECTION OF GLUTATHIONE IN MRSA AT SUB-LETHAL NIMELS DOSIMETRY THAT ALTERS $\Delta\Psi-$ STEADY-BACT TO ONE OF $\Delta\Psi$-TRANS-BACT:

DETECTION OF GLUTATHIONE IN HEK (HUMAN EMBRYONIC KIDNEY CELLS) AT SUB-LETHAL NIMELS DOSIMETRY THAT ALTERS $\Delta\Psi$-STEADY-MITO-MAM TO $\Delta\Psi$-TRANS-MITO-MAM.

PHOTOTHERAPHY OF ERYTHROMYCIN RESISTANT MSSA.

PHOTOTHERAPHY OF ERYTHROMYCIN RESISTANT MRSA.

TREATMENT PROTOCOL

THERAPEUTIC LIGHT DELIVERY APPARATUS, METHOD, AND SYSTEM

RELATED APPLICATIONS

This application is a continuation of U.S. patent application Ser. No. 13/246,447, filed Sep. 27, 2011, which is a continuation of U.S. patent application Ser. No. 13/058,765, filing date not yet assigned, which is the U.S. National Stage of PCT International Application No. PCT/US2009/053752, filed Aug. 13, 2009, which claims the benefit under 35 USC 119(e) of U.S. Provisional Patent Application No. 61/088,401, filed Aug. 13, 2008.

U.S. patent application Ser. No. 13/058,765 is additionally a continuation-in-part of U.S. patent application Ser. No. 11/981,486, filed Oct. 31, 2007, which claims the benefit under 35 USC 119(e) of U.S. Provisional Patent Application No. 60/874,424, filed Dec. 12, 2006.

U.S. patent application Ser. No. 11/981,486 is a continuation-in-part of U.S. patent application Ser. No. 10/776,106, filed Feb. 11, 2004 and of PCT International Patent Application No. PCT/US2006/028616, filed Jul. 21, 2006, which claims the benefit under 35 USC 119(e) to U.S. Provisional Patent Application No. 60/701,896, filed Jul. 21, 2005, 60/711,091, filed Aug. 23, 2005, 60/780,998, filed Mar. 9, 2006, and 60/789,090, filed Apr. 4, 2006.

U.S. patent application Ser. No. 11/981,486 is a continuation-in-part of PCT International Patent Application No. PCT/US2006/030434, filed Aug. 3, 2006, which claims the benefit under 35 USC 119(e) to U.S. Provisional Patent Application No. 60/705,630, filed Aug. 3, 2005.

U.S. patent application Ser. No. 13/058,765 is a continuation-in-part of U.S. patent application Ser. No. 11/930,941, filed Oct. 31, 2007, which is a continuation-in-part of PCT International Patent Application No. PCT/US2006/028616, filed Jul. 21, 2006.

U.S. patent application Ser. No. 11/930,941 is a continuation of PCT International Patent Application No. PCT/US2006/030434, filed Aug. 3, 2006.

U.S. patent application Ser. No. 11/930,941 is further a continuation-in-part of U.S. patent application Ser. No. 10/776,106, filed Feb. 11, 2004, which is a continuation-in-part of U.S. patent application Ser. No. 10/649,910, filed Aug. 26, 2003, which claims the benefit under 35 USC 119(e) to U.S. Provisional Patent Application No. 60/406,493, filed Aug. 28, 2002.

The contents of all the foregoing applications are hereby incorporated herein in their entireties.

FIELD OF THE INVENTION

The present invention generally relates to methods and systems for generating infrared optical radiation in selected energies and dosimetries that will modify the bioenergetic steady-state trans-membrane and mitochondrial potentials of irradiated cells through a depolarization effect, and more particularly, relates to methods and systems for membrane depolarization to potentiate antibiotic compounds in bacterial cells, and particularly antibiotic resistant bacterial cells. This invention also relates generally to phototherapy and, in particular, instruments employing optical fibers or other flexible waveguides to deliver radiation to a targeted biological site.

BACKGROUND OF THE INVENTION

The universal rise of bacteria, fungi and other biological contaminants resistant to antimicrobial agents presents humanity with a grievous threat to its very existence. Since the advent of sulfa drugs (sulfanilamide, first used in 1936) and penicillin (1942, Pfizer Pharmaceuticals), exploitation of significant quantities of antimicrobial agents of all kinds across the planet has created a potent environment for the materialization and spread of resistant contaminants and pathogens. Certain resistant contaminants take on an extraordinary epidemiological significance, because of their predominance in hospitals and the general environment. Widespread use of antibiotics not only prompts generation of resistant bacteria; such as, for example, methicillin-resistant *staphylococcus aureus* (MRSA) and vancomycin-resistant *enterococci* (VRE); but also creates favorable conditions for infection with the fungal organisms (mycosis), such as, *Candida*. Given the increasing world's population and the prevalence of drug resistant bacteria and fungi, the rise in incidence of bacterial or fungal infections is anticipated to continue unabated for the foreseeable future.

Currently, available therapies for bacterial infections include administration of antibacterial therapeutics or, in some instances, application of surgical debridement of the infected area. Because antibacterial therapies alone are rarely curative, especially in view of newly emergent drug resistant pathogens and the extreme morbidity of highly disfiguring surgical therapies, it has been imperative to develop new strategies to treat or prevent microbial infections.

Therefore, there exist a need for methods and systems that can reduce the risk of bacterial infections, in/at a given target site, without intolerable risks and/or intolerable adverse effects to the host organism (e.g., mammalian tissues) other than the targeted microbial contaminants.

Generally, fiber optic phototherapy is an increasingly popular modality for the diagnosis and/or treatment of a wide variety of diseases. For example, in surgery, infrared laser radiation will often be delivered to a surgical site via a handheld instrument incorporating an optically transmissive fiber in order to coagulate blood or cauterize tissue. Other uses for optical fiber-delivered radiation include treatment of atherosclerotic disease and prostatic disease. U.S. Pat. No. 4,878,492 issued to Sinofsky et al., incorporated herein by reference, discloses the use of infrared radiation to heat blood vessel walls during balloon angioplasty in order to fuse the endothelial lining of the blood vessel and seal the surface. Fiber optic delivery systems have been incorporated in endoscopic or catheter-based instruments to deliver radiation to a targeted biological site within a body lumen or cavity. Typically, the fiber optic phototherapy device is inserted through an instrument lumen or catheter for delivery in-vivo. Conventional optical fiber phototherapy devices can include an optical element, such as a focusing lens, that is coupled to the optical fiber by a cylindrical housing. The housing is typically a metallic band or cuff, constructed from stainless steel or gold that is sized to hold both the lens and the optical fiber. Alternatively, the housing can be glued to the optical fiber or can be threaded to facilitate connection to the fiber. Fluoropolymer housings in the prior art are thermally fused to the buffer of the fiber.

The performance of such conventional phototherapy devices incorporating a metallic housing has proven less than optimal. Additional problems associated with such conventional phototherapy devices include loosening of the optical element due to thermal cycling, as the metallic housing and the optical element, as well as the optical fiber, have significantly different thermal characteristics, such as the coefficient thermal expansion. Thus, during the application of radiation, the housing tends to expand greater than both the optical fiber and the optical element, resulting in loosening of the connection between the housing, the optical fiber and optical element, often breaking adhesive bonds. Thermal cycling can also result from sterilization procedures. Moreover, the effects of thermal cycling are magnified by the presence of the metallic housing which can absorb significant amounts of radiation from the optical fiber thereby further increasing the temperature of the housing. Many materials that are typically used for cylindrical cuff material absorb some laser radiation, despite the fact that they look "shiny". For example, a stainless-steel housing can absorb approximately 40% of the incident radiation. Most of the prior art that describes the mounting of an optical element on the end of a fiber-optic teach the use of epoxies to hold all or some of parts of the tip together. The use of epoxies to hold the elements can be troublesome, since the epoxies have limited operating temperatures, may absorb part of the radiation, and darken as they degrade. When an epoxy darkens it absorbs more radiation which can then lead to a thermal runaway failure. Baxter et al, in U.S. Pat. No. 6,102,905 discloses an optical system that is held together by thermoforming the cuff onto a fiber with the identical material as the fiber buffer. This technique although effective, requires a complex thermoforming machine, and can damage the system's optical elements by exposing them to the 500 degrees C. it takes to melt the fluoro-polymers together. This temperature exceeds the recommended temperature for both the optical fiber cladding and the grin lens. This technique can also not be used when the fiber and cuff are not similar materials.

In some applications, it is important in phototherapy that a precise, uniform beam be employed for many conditions. Biophotonic responses are complex and unpredictable variations in illumination may result in unnecessary damage to healthy tissues by overheating, or the survival of malignant pockets by under treating, among other side effects. Uniform output illumination has been the goal of many of the fiber optic devices in the field of photonic medicine.

As the above described optical fiber phototherapy devices have proven less than optimal, it is an object of the present invention to provide improved phototherapy devices provide a precise, stable, controlled illumination of multiple wavelengths. A further object of the present invention is to provide phototherapy devices that inhibit the effects of heat cycling. A further object of the present invention is to provide phototherapy devices that are simple and inexpensive to manufacture.

Another object of the present invention is to provide an improved method of making a phototherapy device. Other general and more specific objects of this invention will in part be obvious and will in part be evident from the drawings and the description which follow.

SUMMARY OF THE INVENTION

These and other objects of the present invention are attained by the phototherapy devices of the present invention which include an integrating optical fiber, having an optical element which is optically coupled to the fiber disposed at its distal end, and a precisely defined, elastic housing physically coupling the optical fiber buffer to the optical element. The phototherapy device of the present invention may further include two or more source optical fibers having a diameter less than that of the integrating fiber optically coupled to the proximal end of the integrating fiber.

A significant advantage the present invention over prior art devices is that coupling and positioning between multiple source fibers, the integrating optical fiber, the housing, the buffer, and the optical element enables a substantially improved precise and stable uniform beam in a durable construction unaffected by the extreme thermal cycling of sterilization and other treatments. Another advantage is that the assembly of the device is performed at room temperature, so the heat sensitive optical components and claddings are not negatively affected. According to a preferred embodiment of the invention, the housing is made from a material having a coefficient of thermal expansion approximately equal to the coefficient of thermal expansion of the buffer. In this manner, both the housing and the buffer will thermally expand (and contract) approximately the same amount, thus minimizing the effects of heat cycling on the device.

According to one embodiment, the housing is made from a polymer material having a anisotropic, non-linear Young's modulus with the greater value co-axial with the optical fiber. Also according to preferred embodiment of the invention, the housing is made with a low index of refraction material to act as a cladding to the encased optical component. According to a further aspect of the present invention, multiple source optical fibers having a combined packed cross-section less than that of the integrating optical fiber may be couple the integrating optical fiber.

An embodiment of a method for making a phototherapy device includes the steps of providing an optical fiber with a perfluorinated polymer buffer coating and attaching an optical element to a distal end of the optical fiber. The optical element can be attached to the distal end of the fiber by encasing the optical element in a housing and press fitting the housing to at least a portion of the buffer. Preferably, the housing is also press fitted to the buffer.

In some embodiments, the step of attaching the optical element can further include the step of employing a precision, press-fit template to facilitate the stable assembly of the elements.

The present invention provides an apparatus, systems and methods for microbial reduction using optical energy. Specific near infrared wavelength ranges photodamage cell membranes, causing oxidative stress and membrane depolarization. Bacteria in the field of the optical beam are photodamaged in that ATP production is compromised, efflux pumps are inhibited, cell wall biosynthesis is disrupted, and the bacteria display increased sensitivity to antibiotics. In many cases, optical photodamage can reverse a drug resistance phenotype, permitting the (re)use of common antibiotics against even multiple drug resistance (MDR) strains.

Accordingly, in a first aspect, the invention includes a method of effectuating antimicrobial activity at a microbial colonization site in a subject, by applying a redox modifying and membrane depolarizing dosage of near infrared energy to the site, the near infrared energy having a first wavelength of about 870 nm and a second wavelength of 930 nm, the dosage of near infrared energy being insufficient to cause thermolysis of subject tissues at the site; and applying one or more antimicrobial agents to the microbial colonization site, wherein at least a two-fold log reduction in microbial colonization is observed in the subject at the colonization site.

In another aspect, the invention provides a method of inhibiting bacterial viability at a microbial colonization site in a subject, by applying a peptidoglycan biosynthesis inhibiting dosage of near infrared energy to the site, the near infrared energy having a first wavelength of about 870 nm and a second wavelength of 930 nm, the dosage of near infrared energy being insufficient to cause thermolysis of subject tissues at the site; and applying one or more antimicrobial agents to the microbial colonization site wherein at least one of the antimicrobial agents binds the active site of a bacterial transpeptidase enzyme, wherein at least a two-fold log reduction in microbial colonization is observed in the subject at the colonization site.

In another aspect, the invention includes a method of inhibiting microbial viability at a microbial colonization site in a subject, comprising: a) applying a DNA replication and transcription inhibiting dosage of near infrared energy to the site, the near infrared energy having a first wavelength of about 870 nm and a second wavelength of 930 nm, the dosage of near infrared energy being insufficient to cause thermolysis of subject tissues at the site; and b) applying one or more antimicrobial agents to the microbial colonization site, wherein at least a two-fold log reduction in microbial colonization is observed in the subject at the colonization site.

In yet another aspect, the invention provides a method of reducing the number and viability of microbes at a microbial colonization site in a subject, comprising: a) applying a bacterial phospholipid biosynthesis inhibiting dosage of near infrared energy to the site, the near infrared energy having a first wavelength of about 870 nm and a second wavelength of 930 nm, the dosage of near infrared energy being insufficient to cause thermolysis of subject tissues at the site; and b) applying one or more antimicrobial agents to the microbial colonization site, wherein at least a two-fold log reduction in microbial colonization is observed in the subject at the colonization site.

In still yet another aspect, the invention provides a method of decontaminating an area of a subject, comprising: a) identifying in or on a subject, a wound or infection site or a surgical location in need of a reduction in bacterial colonization; b) applying one or more photodamaging doses of optical radiation to the area without thermally damaging the area; c) applying an antimicrobial agent to the area.

In another aspect diffuser tip assembly adapted to receive the distal end of optical fiber is disclosed. The assembly includes a reflective cavity including: a first reflector positioned proximal the distal end of the received fiber and including an aperture adapted to admit light emitted from the fiber into the cavity; and a second reflector positioned distal the first reflector. The assembly also includes a diffuser tube positioned between the first and second reflectors about a cavity axis extending from the first reflector to the second reflector, the diffuser tube including an inner void surrounded by an outer portion including a diffusive scattering material. The cavity and diffuser tube are arranged such that at least a portion of light admitted into the cavity is scattered by the diffusive scattering material out of the tip assembly through the outer portion in a direction transverse to the cavity axis. In some embodiments, the cavity and diffuser tube are configured such that light admitted into the cavity is directed from the aperture towards the second reflector; a portion of the light directed towards the second reflector impinges upon the diffusive scattering material and is scattered out of the tip assembly in a direction transverse to the axis; at least a portion of unscattered light impinges upon the second reflector and is reflected back towards the first reflector; and a portion of the light directed back towards the first reflector impinges upon the diffusive scattering material and is scattered out of the tip assembly in a direction transverse to the axis.

In some embodiments, the cavity and diffuser tube are configured such that light admitted into the cavity travels multiple passes between the first and second reflectors; and on each pass, at least a portion of the light is scattered by the diffusive scattering material out of the tip assembly in a direction transverse to the axis. In some embodiments, the light scattered out of the tip assembly on each pass combine to produce a cumulative illumination pattern. In some embodiments, the cumulative illumination pattern is characterized by substantially uniform axial intensity profile along at least a portion of the diffuser tube. In some embodiments, the cumulative illumination pattern is characterized by a substantially uniform azimuthal illumination profile. In some embodiments, the cumulative illumination pattern is characterized by substantially proscribed illumination in the direction parallel to the axis. In some embodiments, the cumulative illumination pattern is a substantially uniform cylindrical illumination pattern emitted radially from the outer surface of the diffuser tube. In some embodiments, the cumulative illumination pattern is determined by at least on at least one chosen from the list consisting of: a length of the diffuser tube, the diameter of the inner void of the diffuser tube, a numerical aperture associate with the aperture in the first reflector. In some embodiments, the inner void is filled with a substantially transparent non-scattering material.

In some embodiments, the at least one of the first and second reflectors includes a curved reflector. In some embodiments, the first reflector is a diffuse reflector and the second reflector is a specular reflector.

In some embodiments, the ratio of the distance between the first reflector and the second reflector along the cavity axis to the outer diameter of the diffusion tube is about 10 or less, about 1 or less, or even about 0.1 or less.

In some embodiments, diffusive scattering material includes a plastic, a glass, a polymer, or a fluid. In some embodiments, the diffusive scattering material includes PTFE. In some embodiments, the diffusive scattering material is adapted to scatter light in the near infrared.

In some embodiments, the reflective cavity and the diffuser tube are autoclavable. Some embodiments include substantially transparent outer jacket adapted to contain the reflective cavity and the diffuser tube. In some embodiments, the outer jacket is detachable from the reflective cavity and the diffuser tube. 22. The diffuser tip assembly of any of the preceding claims, where the tip assembly is adapted to scatter about 80% or more of the light delivered from the fiber while absorbing about 20% or less of the light delivered from the fiber.

In another aspect, a kit for treating an antimicrobial resistant biological contaminate at a treatment site is disclosed which includes: a diffuser tip adapted to receive near infrared therapeutic light from a light delivery system and diffuse the light to illuminate at least a portion of the treatment site; a quantity of an antimicrobial agent; instructions to use the antimicrobial agent in conjunction with the therapeutic light to potentiate the antimicrobial agent to treat the biological contaminate; and suitable packaging. In some embodiments, the diffuser tip is a diffuser tip assembly of the any of the types described herein.

In some embodiments, the therapeutic light includes optical radiation substantially in a first wavelength range from about 865 nm to about 875 nm or a second wavelength range having a wavelength from about 925 nm to about 935 nm, or both wavelength ranges.

In some embodiments, the diffuser tip assembly is adapted to provide substantially uniform illumination of the illuminated portion of the treatment site. In some embodiments, the diffuser tip assembly is adapted to illuminate the illuminated portion of the treatment site at a power density and an energy density which potentiates the antimicrobial agent at the treatment site without causing substantial photothermal or photomechanical damage to the treatment site. In some embodiments, the diffuser tip assembly is adapted to illuminate the illuminated portion of the treatment site at a power density of about 0.2 W/cm$^2$ to about 1 W/cm$^2$ and an energy density from about 100 J/cm² to about 400 J/cm² at the illuminated target region. In some embodiments, the diffuser tip is adapted to operate for about 30 seconds or more at an operating temperature of 110° F. or less.

In some embodiments, the diffuser tip assembly is adapted for detachable connection to a distal end of an optical fiber which transmits the therapeutic light from a light source to the distal end of the fiber.

In some embodiments, the quantity of antimicrobial agent includes a topical paste.

In some embodiments, the antimicrobial agent includes an antibiotic or a pharmacologically acceptable salt thereof, selected from the group consisting of: β-lactams, glycopeptides, cyclic polypeptides, macrolides, ketolides, anilinouracils, lincosamides, chloramphenicols, tetracyclines, aminoglycosides, bacitracins, cefazolins, cephalosporins, mupirocins, nitroimidazoles, quinolones and fluoroquinolones, novobiocins, polymixins, cationic detergent antibiotics, oxazolidinones or other heterocyclic organic compounds, glycylcyclines, lipopeptides, cyclic lipopeptides, pleuromutilins, and gramicidins, daptomycins, linezolids, ansamycins, carbacephems, carbapenems, monobactams, platensimycins, streptogramins and tinidazoles.

In some embodiments, the antimicrobial agent is ineffective for treating the antimicrobial resistant biological contaminate in the absence of the therapeutic light. In some embodiments, the resistant biological contaminate includes MRSA or MSSA.

In some embodiments, the biological contaminate includes an aberrant microbial colonization, and where the instructions include instruction to use the antimicrobial agent in conjunction with the therapeutic light to potentiate the antimicrobial agent to reduce the level of colonization at the treatment site. In some embodiments, the an aberrant microbial colonization, prior to application of the treatment light, has a drug resistant phenotype with respect to the antimicrobial agent.

In some embodiments, the diffuser tip is sterilized.

In another aspect, q therapeutic system for treatment of a biological contaminant at a treatment site is disclosed including: an optical radiation generation device configured and arranged to generate near infrared therapeutic light; a controller operatively connected to the optical radiation generation device for controlling dosage of the therapeutic light transmitted to the treatment site at a dosimetry sufficient to produce photodamage in the biological contaminant without causing substantial photothermal or photomechanical damage to biological tissue at the treatment site; a delivery assembly including an optical fiber which directs the therapeutic light to be transmitted to the treatment site; and a diffuser tip adapted to receive the therapeutic light from the delivery assembly and diffuse the therapeutic light to illuminate at least a portion of the treatment site with a prescribed illumination pattern.

In some embodiments, the diffuser tip is the diffuser tip of any of the types described herein.

In some embodiments, where the therapeutic light includes optical radiation substantially in a first wavelength range from about 865 nm to about 875 nm or a second wavelength range having a wavelength from about 925 nm to about 935 nm, or both wavelength ranges.

In some embodiments, the diffuser tip assembly is adapted to provide substantially uniform illumination of at least a portion of the illuminated portion of the treatment site. In some embodiments, the diffuser tip assembly is adapted to illuminate the portion of the treatment site at a power density and an energy density which potentiates an antimicrobial application at the treatment site.

In some embodiments, the diffuser tip assembly is adapted to illuminate the portion of the treatment site at a power density of about 0.3 W/cm² to about 0.7 W/cm² and an energy density from about 100 J/cm² to about 400 J/cm² at the illuminated portion of the treatment site. In some embodiments, the diffuser tip is adapted to operate for about 30 seconds or more at an operating temperature of 110° F. or less.

In some embodiments, the diffuser tip assembly is adapted for detachable connection to a distal end of the optical fiber.

In another aspect, a method treatment of a biological contaminant at a treatment site is disclosed which includes: generating near infrared therapeutic light; controlling dosage of the therapeutic light transmitted to the treatment site at a dosimetry sufficient to produce photodamage in the biological contaminant without causing substantial photothermal or photomechanical damage to biological tissue at the treatment site; directing the therapeutic light to be transmitted to the treatment site; and using a diffuser tip, diffusing the therapeutic light to illuminate at least a portion of the treatment site with a prescribed illumination pattern.

In some embodiments, the diffuser tip is a diffuser tip assembly of any of the types described herein.

In some embodiments, the therapeutic light includes optical radiation substantially in a first wavelength range from about 865 nm to about 875 nm or a second wavelength range having a wavelength from about 925 nm to about 935 nm, or both wavelength ranges.

In some embodiments, the diffusing the therapeutic light includes providing substantially uniform illumination of at least a portion of the illuminated portion of the treatment site.

Some embodiment further include applying a quantity of antimicrobial agent the treatment site; and illuminating the portion of the treatment site at a power density and an energy density which potentiates the antimicrobial application.

In some embodiments, the antimicrobial agent is ineffective for treating the antimicrobial resistant biological contaminate in the absence of the therapeutic light. In some embodiments, the antimicrobial agent is ineffective for treating the biological contaminate in the absence of the therapeutic light. In some embodiments, the biological contaminate includes an aberrant microbial colonization, and further including includes using the antimicrobial agent in conjunction with the therapeutic light to potentiate the antimicrobial agent to reduce the level of colonization at the treatment site. In some embodiments, the aberrant microbial colonization, prior to application of the treatment light, has a drug resistant phenotype with respect to the antimicrobial agent.

In some embodiments, controlling the dosage of the therapeutic light includes controlling the illumination of the portion of the treatment site at a power density of about 0.2 W/cm² to about 1 W/cm² and an energy density from about 100 J/cm² to about 400 J/cm² at the illuminated region.

Exemplary antimicrobial agents that are appropriate for use in conjunction with optical photodamage to reduce bacterial counts include common antibiotics and pharmacologically acceptable salt thereof, including β-lactams, glycopeptides, cyclic polypeptides, macrolides, ketolides, anilinouracils, lincosamides, chloramphenicols, tetracyclines, aminoglycosides, bacitracins, cefazolins, cephalosporins, mupirocins, nitroimidazoles, quinolones and fluoroquinolones, novobiocins, polymixins, cationic detergent antibiotics, oxazolidinones or other heterocyclic organic compounds, glycylcyclines, lipopeptides, cyclic lipopeptides, pleuromutilins, and gramicidins, daptomycins, linezolids, ansamycins, carbacephems, carbapenems, monobactams, platensimycins, streptogramins and tinidazoles.

In another aspect, an optical delivery apparatus is disclosed including: an optical fiber extending between a distal end having a distal end face and a proximal end having a proximal end face, the fiber configured to receive light from at least one source at the proximal end face, transmit the light from the proximal end to the distal end, and emit the light from the distal end face; an optical element positioned to receive the light emitted from the distal end face and direct the light to an illumination region; and a non-metallic housing containing the optical fiber and the optical element and maintaining the relative position of the optical fiber and the optical element.

In some embodiments, the non-metallic housing is an elastic housing. In some embodiments, the elastic housing is an elastic cuff stretched over the optical fiber and optical element. The compressive force from the elastic cuff maintains the relative position of the optical fiber and the optical element. In some embodiments, the elastic cuff is tubular elastic member having a resting inner diameter lass that that of the optical fiber and optical element. In some embodiments, the non-metallic housing includes non-metallic clamp member maintaining the relative position of the optical fiber and the optical element.

The apparatus of any preceding claim, where the non-metallic housing is substantially composed of a polymer material having a low index of refraction. In some embodiments, the index of refraction is less than an index of refraction of the optical element. In some embodiments, the index of refraction is less than 1.7, less than 1.6, less than 1.5, less than 1.4, less than 1.3, less than 1.2, less than 1.1, less than 1, or even less.

In some embodiments the optical fiber includes a outer buffer layer, a cladding and a core, the buffer layer is disposed about a cladding, and the cladding is disposed about the core; the coefficient of thermal expansion of the buffer layer is substantially matched to the coefficient of thermal expansion of the elastic housing.

In some embodiments, the buffer layer includes a polymer, e.g., a perflourinated polymer.

In some embodiments, the cladding and core extend beyond the buffer layer at the distal end of the optical fiber.

In some embodiments, the optical element is proximal to the distal end of the fiber. In some embodiments, the optical element is spaced apart from the distal end of the fiber, and the housing maintains the spacing of the optical element from the distal end of the fiber. In some embodiments, the optical element abuts the distal end of the fiber.

In some embodiments, the optical element includes at least one selected from the list consisting of: a lens, a GRIN lens, a diffractive element, a diffusive element, a hologram, a concentrating element, and a collimator.

In some embodiments, the optical element directs the light to illuminate the illumination region with substantially uniform illumination.

In some embodiments, the optical element forms a beam of light from the light from the distal end of the fiber, where the beam has a substantially non-gaussian beam profile. In some embodiments, the beam has a substantially uniform beam profile. In some embodiments, beam profile varies by less than 5%, less than 1%, or even less across the beam profile.

In some embodiments, the at least one source includes at a first source and a second source, and where In some embodiments, the fiber is configured to receive light from the first and the second source at the proximal end face, transmit the light from the proximal end to the distal end, and emit the light from the distal end face. In some embodiments, the optical element directs the light from the first and second to illuminate the illumination region such that light from the first and second source overlaps at at least a portion of the illumination region.

In some embodiments, the first and second light sources produce light having differing wavelengths.

Some embodiments include a first source fiber and a second source each having a proximal end located proximal a respective on of the first source and the second source, and each having a distal end located proximal to the proximal end of the optical fiber. In some embodiments, the first source fiber transmits light from the first source to the proximal end of the optical fiber and the second source fiber transmits light from the second source to the proximal end of the optical fiber.

In some embodiments, the first and second source fibers have a combined diameter 9 e.g. a combined packed cross sectional diameter) at their respective distal ends less than that of the optical fiber at its proximal end.

In some embodiments, the first and second source fibers have a combined diameter at their respective distal ends less than that of the optical fiber at its proximal end.

In some embodiments, the at least one source includes at least one selected from the list consisting of: a laser, a diode laser, a solid state laser, a dye laser, an LED, an OLED, and a lamp.

In some embodiments, the optical element images the core of the optical fiber at the distal end face to the illumination region.

In some embodiments, the optical element has a focal plane, and the non-metallic housing maintains the relative position of the optical fiber and the optical element such that the core of the optical fiber at the distal end face is positioned near the focal plane.

In another aspect, a therapeutic system for treatment of a biological contaminant at a treatment site is disclosed including: an optical radiation generation device configured and arranged to generate near infrared therapeutic light; a controller operatively connected to the optical radiation generation device for controlling dosage of the therapeutic light transmitted to the treatment site at a dosimetry sufficient to produce photodamage in the biological contaminant without causing substantial photothermal or photomechanical damage to biological tissue at the treatment site; and a delivery assembly including any of the optical delivery devices described herein and configured to deliver the therapeutic light to the treatment site to illuminate at least a portion of the treatment site with a prescribed illumination pattern. In some embodiments, the optical radiation generation device includes the at least one source. In some embodiments, the therapeutic light includes optical radiation substantially in a first wavelength range from about 865 nm to about 875 nm or a second wavelength range having a wavelength from about 925 nm to about 935 nm, or both wavelength ranges. In some embodiments, the treatment light includes optical radiation at both wavelength ranges.

In some embodiments, the delivery assembly is adapted to provide substantially uniform illumination of at least a portion of the illuminated portion of the treatment site. In some embodiments, the delivery assembly is adapted to illuminate the portion of the treatment site at a power density and an energy density which potentiates an antimicrobial application at the treatment site. In some embodiments, the delivery assembly is adapted to illuminate the portion of the treatment site at a power density of about 0.3 W/cm$^2$ to about 0.7 W/cm$^2$ and an energy density from about 100 J/cm$^2$ to about 400 J/cm$^2$ at the illuminated portion of the treatment site. In some embodiments, the delivery assembly is adapted to operate for about 30 seconds or more at an operating temperature of 110° F. or less. In some embodiments, the delivery assembly is adapted for detachable coupling to the optical radiation generation device.

In another aspect, a method treatment of a biological contaminant at a treatment site is disclosed including: generating near infrared therapeutic light; controlling dosage of the therapeutic light transmitted to the treatment site at a dosimetry sufficient to produce photodamage in the biological contaminant without causing substantial photothermal or photomechanical damage to biological tissue at the treatment site; and using a delivery assembly including the optical deliver apparatus of any of the claims, directing the therapeutic light to be transmitted to the treatment site to illuminate at least a portion of the treatment site with a prescribed illumination pattern.

In some embodiments, generating near infrared therapeutic light includes generating light from the at least one source. In some embodiments, the therapeutic light includes optical radiation substantially in a first wavelength range from about 865 nm to about 875 nm or a second wavelength range having a wavelength from about 925 nm to about 935 nm, or both wavelength ranges. In some embodiments, the treatment light includes optical radiation at both wavelength ranges.

In some embodiments, directing the therapeutic light to be transmitted to the treatment site to illuminate at least a portion of the treatment site with a prescribed illumination pattern includes providing substantially uniform illumination of at least a portion of the illuminated portion of the treatment site.

Some embodiments include, applying a quantity of antimicrobial agent the treatment site; and illuminating the portion of the treatment site at a power density and an energy density which potentiates the antimicrobial application. In some embodiments, the antimicrobial agent is ineffective for treating the antimicrobial resistant biological contaminate in the absence of the therapeutic light.

In some embodiments, the biological contaminate includes an aberrant microbial colonization, and further including includes using the antimicrobial agent in conjunction with the therapeutic light to potentiate the antimicrobial agent to reduce the level of colonization at the treatment site.

In some embodiments, the aberrant microbial colonization, prior to application of the treatment light, has a drug resistant phenotype with respect to the antimicrobial agent.

In some embodiments, controlling the dosage of the therapeutic light includes controlling the illumination of the portion of the treatment site at a power density of about 0.2 $W/cm^2$ to about 1 $W/cm^2$ and an energy density from about 100 $J/cm^2$ to about 400 $J/cm^2$ at the illuminated region.

In another aspect, a system is disclosed including a source of therapeutic light optically coupled to an optical delivery assembly including the optical delivery apparatus of any of the types described herein.

In another aspect, a method is disclosed including using the optical delivery apparatus of any the types described herein to deliver therapeutic light to illuminate a treatment site.

In another aspect, a method of constructing an optical delivery device is disclosed including: obtaining an optical fiber extending between a distal end having a distal end face and a proximal end having a proximal end face; obtaining an optical element; obtaining a non-metallic housing; and fitting the optical fiber and optical element within the housing such that the housing maintains the relative position of the optical fiber and the optical element.

of the types described herein the fitting the optical fiber and optical element within the housing includes press fitting an elastic cuff about the optical fiber and optical element.

In some embodiments, the fitting the optical fiber and optical element within the housing is performed at temperatures less than 500 degrees C., less than 250 degrees C., less than 100 degrees C, less than 50 degrees C. or even less.

In some embodiments, the fitting the optical fiber and optical element within the housing includes using a removable template to position the optical fiber and optical element.

In some embodiments, the fitting the optical fiber and optical element within the housing includes fitting the optical fiber and optical element within the housing without applying heat to shrink any portion of the housing.

In some embodiments, the non-metallic housing is an elastic housing. In some embodiments, the elastic housing is an elastic cuff, and where the fitting the optical fiber and optical element within the housing includes stretching the cuff over the optical fiber and optical element such that compressive force from the elastic cuff maintains the relative position of the optical fiber and the optical element.

Various embodiments may include any of the features of techniques described above, either alone, or in any combination.

BRIEF DESCRIPTION OF THE DRAWINGS

Aspects of the invention may more fully be understood from the following description when read together with the accompanying drawings, which are to be regarded as illustrative in nature, and not limiting. The drawings are not necessarily to scale, emphasis instead being placed on the principles of the invention. In the drawings.

DETAILED DESCRIPTION OF THE INVENTION

Figure 1:
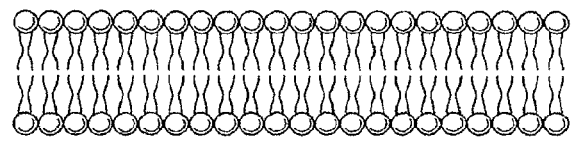
FIG. 1 shows a typical phospholipid bilayer.

As used in this specification, the singular forms "a", "an" and "the" also encompass the plural forms of the terms to which they refer, unless the content clearly dictates otherwise. For example, reference to "a NIMELS wavelength" includes any wavelength within the ranges of the NIMELS wavelengths described, as well as combinations of such wavelengths.

The present invention is directed to methods and systems for enhancing bacterial susceptibility to antimicrobial agents thereby reducing the minimum inhibitory concentration (MIC) of the antimicrobial agent necessary to attenuate or eliminate microbial related pathology and/or enabling therapeutic use of antimicrobial agents that would otherwise be ineffective due to bacterial resistance. According to methods and systems of the present invention, near infrared optical radiation in selected energies and dosimetries (herein known as NIMELS, standing for "near infrared microbial elimination system") are used to cause a depolarization of membranes within the irradiated field, that will alter the absolute value of the membrane potential ($\Delta\Psi$) of the irradiated cells.

This altered $\Delta\Psi$ will cause an affiliated weakening of the proton motive force $\Delta p$, and the bioenergetics of all affected membranes. Accordingly, the effects of NIMELS irradiation (NIMELS effect) can potentiate existing antimicrobial agents against microbes infecting and causing harm to human or animal hosts. These NIMELS effects will affect many cellular anabolic reactions (e.g., cell wall formation) and drug-resistance mechanisms (e.g., efflux pumps) that require chemiosmotic electrochemical energy to function. Hence, any membrane bound cellular resistance mechanisms or anabolic reactions that makes use of the membrane potential $\Delta\Psi$, proton motive force $\Delta p$, or the phosphorylation potential $\Delta Gp$ for their functional energy needs, will be affected by the NIMELS effects, and accordingly provide therapeutic targets for the methods and systems of the present invention.

The methods and systems of the present invention utilize optical radiation to sensitize undesirable microbial cells (e.g., MRSA infection in skin) without substantial thermal or chemical damage to host tissues.

In exemplary embodiments, the applied optical radiation used in accordance with methods and systems of the present invention includes one or more, and preferably two independent wavelengths ranging from about 850 nm to about 900 nm, at a NIMELS dosimetry, as described herein. In one aspect, wavelengths from about 865 nm to about 875 nm are utilized. In another aspect, such applied radiation has a wavelength from about 905 nm to about 945 nm at a NIMELS dosimetry. In one aspect, such applied optical radiation has a wavelength from about 925 nm to about 935 nm. In a particular aspect, a wavelength of (or narrow wavelength range including) 930 nm can be employed. In some aspects of the present invention, multiple wavelength ranges include 870 and 930 nm, respectively.

In one embodiment, the methods and systems of the present invention are used in treating, reducing and/or eliminating the infectious entities known to cause cutaneous or wound infections such as *staphyloccocci* and *enterococci*.

Staphyloccoccal and enterococcal infections can involve almost any skin surface on the body, and is known to cause numerous skin conditions such as boils, carbuncles, bullous impetigo and scalded skin syndrome. Accordingly, one objective of the invention is to prevent or treat staphyloccoccal and enterococcal infections of the host skin, thereby treating the aforementioned conditions. *S. aureus* is also the cause of staphylococcal food poisoning, enteritis, osteomilitis, toxic shock syndrome, endocarditis, meningitis, pneumonia, cystitis, septicemia and post-operative wound infections. Accordingly, another objective of the invention is to prevent or treat such infections. *S. aureus* can be acquired while a patient is in a hospital or long-term care facility, and yet another object of the invention is to prevent or treat nosocomial infections in the host.

The widespread use of antibiotics have led to the development of antibiotic-resistant strains of *S. aureus*. These strains are called methicillin resistant *staphylococcus aureus* (MRSA). Infections caused by MRSA are frequently resistant to a wide variety of antibiotics (especially β-lactams) and are associated with significantly higher rates of morbidity and mortality, higher costs, and longer hospital stays than infections caused by non-MRSA microorganisms. Risk factors for MRSA infection in the hospital include colonization of the nares, surgery, prior antibiotic therapy, admission to intensive care, exposure to a MRSA-colonized patient or health care worker, being in the hospital more than 48 hours, and having an indwelling catheter or other medical device that goes through the skin. Thus, a further object of the invention is to prevent or treat drug resistant bacterial infections of the host, preferably but not limited to MRSA infections of the host.

The term "NIMELS dosimetry" denotes the power density (W/cm$^2$) and the energy density (J/cm$^2$) (where 1 Watt=1 Joule per second) values at which a subject wavelength according to the invention is capable of generating a reactive oxygen species ("ROS") and thereby reduce the level of a biological contaminant in a target site. The term also includes irradiating a cell to increase the sensitivity of the biological contaminant through the lowering of $\Delta\Psi$ with the concomitant generation of ROS of an antimicrobial or antineoplastic agent, wherein the contaminant is resistant to the agent otherwise. This method can be effected without intolerable risks and/or intolerable side effects on the host subject's tissue other than the biological contaminant.

By "potentiation" of an antibacterial agent, it is meant that the methods and systems of this invention counteract the resistance mechanisms in the microbe sufficiently for the agent to inhibit the growth and/or proliferation of said microbe at a lower concentration than in the absence of the present methods and systems. In cases where resistance is essentially complete, i.e., the agent has no apparent bacteriostatic or bacteriocidal effect on the microbial cells, potentiation means that the agent will inhibit the growth and/or proliferation of pathogenic cells at a therapeutically acceptable dosage, thereby treating the disease state.

As used herein, the term "Membrane Dipole Potential Ψd" (in contrast to the Transmembrane Potential $\Delta\Psi$) refers to the potential formed between the highly hydrated lipid heads (hydrophilic) at the membrane surface and the low polar interior of the bilayer (hydrophobic). Lipid bilayers intrinsically possess a substantial Membrane Dipole Potential Ψd arising from the structural organization of dipolar groups and molecules, primarily the ester linkages of the phospholipids and water.

Ψd does not depend upon the ions at the membrane surface and will be used herein to describe five different dipole potentials:

1) Mammalian Plasma Membrane Dipole Potential Ψd-plas-mam;
2) Mammalian Mitochondrial Membrane Dipole Potential Ψd-mito-mam;
3) Fungal Plasma Membrane Dipole Potential Ψd-plas-fungi;
4) Fungal Mitochondrial Membrane Dipole Potential Ψd-mito-fungi; and
5) Bacterial Plasma Membrane Dipole Potential Ψd-plas-bact.

As used herein, the term "Trans-Membrane Potential" refers to the electrical potential difference between the aqueous phases separated by a membrane (dimensions mV) and will be given by the symbol ($\Delta\Psi$). $\Delta\Psi$ does depend upon the ions at the membrane surface and will be used herein to describe three different plasma trans-membrane potentials.

1) Mammalian Plasma Trans-Membrane Potential $\Delta\Psi$-plas-mam
2) Fungal Plasma Trans-Membrane Potential $\Delta\Psi$-plas-fungi
3) Bacterial Plasma Trans-Membrane Potential $\Delta\Psi$-plas-bact As used herein, the term "Mitochondrial Trans-Membrane Potential" refers to the electrical potential difference between the compartments separated by the mitochondrial inner membrane (dimensions mV) and will be used herein to describe two different mitochondrial trans-membrane potentials.

1) Mammalian Mitochondrial Trans-Membrane Potential $\Delta\Psi$-mito-mam
2) Fungal Mitochondrial Trans-Membrane Potential $\Delta\Psi$-mito-fungi As used herein, the term "bacterial plasma trans-membrane potential ($\Delta\Psi$-plas-bact)" refers to the electrical potential difference in the bacterial cell plasma membrane. The bacterial plasma membrane potential is generated by the steady-state flow (translocation) of electrons and protons (H$^+$) across the bacterial plasma membrane that occurs with normal electron transport and oxidative phosphorylation, within the bacterial plasma membrane. A common feature of all electron transport chains is the presence of a proton pump to create a transmembrane proton gradient. Although bacteria lack mitochondria, aerobic bacteria carry out oxidative phosphorylation (ATP production) by essentially the same process that occurs in eukaryotic mitochondria.

As used herein, the term "P-class ion pump" refers to a trans-membrane active transport protein assembly which contains an ATP-binding site (i.e., it needs ATP to function). During the transport process, one of the protein subunits is phosphorylated, and the transported ions are thought to move through the phosphorylated subunit. This class of ion pumps includes the Na$^+$/K$^+$-ATPase pump in the mammalian plasma membrane, which maintains the Na$^+$ and K$^+$ electrochemical potential ($\Delta$Na$^+$/K$^+$) and the pH gradients typical of animal cells. Another important member of the P-class ion pumps, transports protons (H$^+$ ions) out of and K$^+$ ions in to the cell.

As used herein, the term "steady-state plasma trans-membrane potential ($\Delta\Psi$-steady)" refers to the quantitative Plasma Membrane Potential of a mammalian, fungal or bacterial cell before irradiation in accordance with the methods and systems of the present invention that would continue into the future in the absence of such irradiation. For example, the steady-state flow of electrons and protons across a bacterial cell membrane that occurs during normal electron transport and oxidative phosphorylation would be in a steady-state due to a constant flow of conventional redox reactions occurring across the membrane. Conversely any modification of this redox state would cause a transient-state membrane potential. $\Delta\Psi$-steady will be used herein to describe three (3) different steady-state plasma trans-membrane potentials, based on species.

1) Steady-state mammalian plasma trans-membrane potential $\Delta\Psi$-steady-mam
2) Steady-state fungal plasma trans-membrane potential $\Delta\Psi$-steady-fungi
3) Steady-state bacterial plasma trans-membrane potential $\Delta\Psi$-steady-bact As used herein, the term "Transient-state plasma membrane potential ($\Delta\Psi$-tran)" refers to the Plasma Membrane Potential of a mammalian, fungal or bacterial cell after irradiation in accordance with the methods and systems of the present invention whereby the irradiation has changed the bioenergetics of the plasma membrane. In a bacteria, $\Delta\Psi$-tran will also change the redox state of the cell, as the plasma membrane is where the ETS and cytochromes reside. $\Delta\Psi$-tran is a state that would not occur without irradiation using methods of the present invention. $\Delta\Psi$-tran will be used herein to describe three (3) different Transient-state plasma trans-membrane potentials based on species.
1) Transient-state mammalian plasma trans-membrane potential $\Delta\Psi$-tran-mam
2) Transient-state fungal plasma trans-membrane potential $\Delta\Psi$-tran-fungi
3) Transient-state bacterial plasma trans-membrane potential $\Delta\Psi$-tran-bact As used herein, the term "steady-state mitochondrial membrane potential ($\Delta\Psi$-steady-mito)" refers to the quantitative Mitochondrial Membrane Potential of mammalian or fungal mitochondria before irradiation in accordance with the methods and systems of the present invention that would continue into the future, in the absence of such irradiation. For example, the steady-state flow of electrons and protons across mitochondrial inner membrane that occurs during normal electron transport and oxidative phosphorylation would be in a steady-state because of a constant flow of conventional redox reactions occurring across the membrane. Any modification of this redox state would cause a transient-state mitochondrial membrane potential. $\Delta\Psi$-steady-mito will be used herein to describe two (2) different steady-state mitochondrial membrane potentials based on species.
1) Steady-state mitochondrial mammalian potential $\Delta\Psi$-steady-mito-mam
2) Steady-state mitochondrial fungal potential $\Delta\Psi$-steady-mito-fungi As used herein, the term "transient-state mitochondrial membrane potential ($\Delta\Psi$-tran-mito-mam or $\Delta\Psi$-tran-mito-fungi)" refers to the membrane potential of a mammalian or fungal cell after irradiation in accordance with the methods and systems of the present invention whereby the irradiation has changed the bioenergetics of the mitochondrial inner membrane. In mammalian and fungal cells, $\Delta\Psi$-tran-mito will also change the redox state of the cell, as the inner mitochondrial membrane is where the electron transport system (ETS) and cytochromes reside. $\Delta\Psi$-tran-mito could also drastically affect (the Proton-motive force) $\Delta p$-mito-mam and $\Delta p$-mito-fungi, as these mitochondrial ($H^+$) gradients are generated in the mitochondria, to produce adequate ATP for a myriad of cellular functions. $\Delta\Psi$-tran-mito is a state that would not occur without irradiation in accordance with methods and systems of the present invention. $\Delta\Psi$-tran-mito will be used herein to describe two (2) different transient-state mitochondrial membrane potentials based on species.
1) Transient-state mitochondrial mammalian potential $\Delta\Psi$-tran-mito-mam
2) Transient-state mitochondrial fungal potential $\Delta\Psi$-tran-mito-fungi As used herein, the term "proton electrochemical gradient" ($\Delta\mu H^+$) (dimensions kJ mol-1) refers to the electrical and chemical properties across a membrane, particularly proton gradients, and represents a type of cellular potential energy available for work in a cell. This proton electrochemical potential difference between the two sides of a membrane that engage in active transport involving proton pumps, is at times also called a chemiosmotic potential or proton motive force. When $\Delta\mu H^+$ is reduced by any means, it is a given that cellular anabolic pathways and resistance mechanisms in the affected cells are inhibited. This can be accomplished by combining $\lambda n$ and Tn to irradiate a target site alone, or can be further enhanced with the simultaneous or sequential administration of a pharmacological agent configured and arranged for delivery to the target site (i.e., the co-targeting of an anabolic pathway with ($\lambda n$ and Tn)+(pharmacological molecule or molecules)).

As used herein, the term "Ion Electrochemical Gradient ($\Delta\mu x+$)" refers to the electrical and chemical properties across a membrane caused by the concentration gradient of an ion (other than $H^+$) and represents a type of cellular potential energy available for work in a cell. In mammalian cells, the $Na^+$ ion electrochemical gradient is maintained across the plasma membrane by active transport of $Na^+$ out of the cell. This is a different gradient than the proton electrochemical potential, yet is generated from an ATP coupled pump, said ATP produced during oxidative phosphorylation from the mammalian mitochondrial proton-motive force ($\Delta p$-mito-mam). When $\Delta\mu x^+$ is reduced by any means, it is a given that cellular anabolic pathways and resistance mechanisms in the affected cells are inhibited. This can be accomplished by combining $\lambda n$ and Tn to irradiate a target site alone, or can be further enhanced with the simultaneous or sequential administration of a pharmacological agent configured and arranged for delivery to the target site (i.e., the co-targeting of an anabolic pathway with ($\lambda n$ and Tn)+(pharmacological molecule or molecules)).

As used herein, the term "co-targeting of a bacterial anabolic pathway" refers to (the $\lambda n$ and Tn lowering of ($\Delta\mu H^+$) and/or ($\Delta\mu x^+$) of cells at the target site to affect an anabolic pathway)+(a pharmacological molecule or molecules to affect the same bacterial anabolic pathway) and can refer to any of the following bacterial anabolic pathways that are capable of being inhibited with pharmacological molecules: wherein the targeted anabolic pathway is peptidoglycan biosynthesis that is co-targeted by a pharmacological agent that binds at the active site of the bacterial transpeptidase enzymes (penicillin binding proteins) which cross-links peptidoglycan in the bacterial cell wall. Inhibition of these enzymes ultimately cause cell lysis and death; wherein the targeted bacterial anabolic pathway is peptidoglycan biosynthesis that is co-targeted by a pharmacological agent that binds to acyl-D-alanyl-D-alanine groups in cell wall intermediates and hence prevents incorporation of N-acetylmuramic acid (NAM)- and N-acetylglucosamine (NAG)-peptide subunits into the peptidoglycan matrix (effectively inhibiting peptidoglycan biosynthesis by acting on transglycosylation and/or transpeptidation) thereby preventing the proper formation of peptidoglycan, in gram-positive bacteria; wherein the targeted bacterial anabolic pathway is peptidoglycan biosynthesis that is co-targeted by a pharmacological agent that binds with $C_{55}$-isoprenyl pyrophosphate and prevents pyrophosphatase from interacting with $C_{55}$-isoprenyl pyrophosphate thus reducing the amount of $C_{55}$-isoprenyl pyrophosphate that is available for carrying the building blocks peptidoglycan outside of the inner membrane; wherein the targeted anabolic pathway is bacterial protein biosynthesis that is co-targeted by a pharmacological agent that binds to the 23S rRNA molecule in the subunit 50S subunit of the bacterial ribosome, causing the accumulation of peptidyl-tRNA in the cell, hence depleting the free tRNA necessary for activation of α-amino acids, and inhibiting transpeptidation by causing premature dissociation of peptidyl tRNA from the ribosome; wherein the co-targeted pharmacological agent binds simultaneously to two domains of 23S RNA of the 50 S bacterial ribosomal subunit, and can thereby inhibit the formation of the bacterial ribosomal subunits 50 S and 30S (ribosomal subunit assembly); wherein the co-targeted pharmacological agent is chlorinated to increases its lipophilicity to penetrate into bacterial cells, and binds to the 23S portion of the 50S subunit of bacterial ribosomes and prevents the translocation of the peptidyl-tRNA from the Aminoacyl site (A-site) to the Peptidyl site (P-site) thereby inhibiting the transpeptidase reaction, which results in an incomplete peptide being released from the ribosome; wherein the targeted anabolic pathway is bacterial protein biosynthesis that is co-targeted by pharmacological agent that binds to the 30S bacterial ribosomal subunit and blocks the attachment of the aminoacyl tRNA from binding to the acceptor site (A-site) of the ribosome, thereby inhibiting the codon-anticodon interaction and the elongation phase of protein synthesis; wherein the co-targeted pharmacological agent binds more avidly to the bacterial ribosomes, and in a different orientation from the classical subclass of polyketide antimicrobials having an octahydrotetracene-2-carboxamide skeleton, so that they are active against strains of S. aureus with a tet(M) ribosome and tet(K) efflux genetic determinant; wherein the targeted anabolic pathway is bacterial protein biosynthesis that is co-targeted by a pharmacological agent that binds to a specific aminoacyl-tRNA synthetase to prevent the esterification of a specific amino acid or its precursor to one of its compatible tRNA's, thus preventing formation of an aminoacyl-tRNA and hence halting the incorporation of a necessary amino acid into bacterial proteins; wherein the targeted anabolic pathway is bacterial protein biosynthesis that is co-targeted by a pharmacological agent that inhibits bacterial protein synthesis before the initiation phase, by binding the 50S rRNA through domain V of the 23S rRNA, along with interacting with the 16S rRNA of the 30S ribosomal subunit, thus preventing binding of the initiator of protein synthesis formyl-methionine (f-Met-tRNA), and the 30S ribosomal subunit; wherein the targeted anabolic pathway is bacterial protein biosynthesis that is co-targeted by a pharmacological agent that interacts with the 50S subunit of bacterial ribosomes at protein L3 in the region of the 23S rRNA P site near the peptidyl transferase center and hence inhibits peptidyl transferase activity and peptidyl transfer, blocks P-site interactions, and prevents the normal formation of active 50S ribosomal subunits; wherein the targeted anabolic pathway is DNA replication and transcription that is co-targeted by a pharmacological agent that inhibits Topoisomerase II (DNA gyrase) and/or Topoisomerase IV; wherein the targeted anabolic pathway is DNA replication and translation that is co-targeted by a pharmacological agent that inhibits DNA polymerase IIIC, the enzyme required for the replication of chromosomal DNA in gram-positive bacteria, but not present in gram-negative bacteria; wherein the targeted anabolic pathway is DNA replication and transcription that is co-targeted by a pharmacological hybird compound that inhibits Topoisomerase II (DNA gyrase) and/or Topoisomerase IV and/or DNA polymerase IIIC; wherein the targeted anabolic pathway is bacterial phospholipid biosynthesis that is co-targeted by a topical pharmacological agent that acts on phosphatidylethanolamine-rich cytoplasmic membranes and works well in combination with other topical synergistic agents; wherein the targeted anabolic pathway is bacterial fatty acid biosynthesis that is co-targeted by a pharmacological agent that inhibits bacterial fatty acid biosynthesis through the selective targeting of β-ketoacyl-(acyl-carrier-protein (ACP)) synthase I/II (FabF/B), an essential enzymes in type II fatty acid synthesis; wherein the targeted anabolic pathway is maintenance of bacterial plasma trans-membrane potential $\Delta\Psi$-plas-bact and the co-targeting pharmacological agent disrupts multiple aspects of bacterial cell membrane function on its own, by binding primarily to gram positive cytoplasmic membranes, not penetrating into the cells, and causing depolarization and loss of membrane potential that leads to inhibition of protein, DNA and RNA synthesis; wherein the co-targeting pharmacological agent increases the permeability of the bacterial cell wall, and hence allows inorganic cations to travel through the wall in an unrestricted manner thereby destroying the ion gradient between the cytoplasm and extracellular environment; wherein the targeted anabolic pathway is maintenance of bacterial membrane selective permeability and bacterial plasma trans-membrane potential $\Delta\Psi$-plas-bact, and the co-targeting pharmacological agent is a cationic antibacterial peptide that is selective for the negatively charged surface of bacterial membranes relative to the neutral membrane surface of eukaryotic cells and leads to prokaryotic membrane permeablization and ultimate perforation and/or disintegration of bacterial cell membranes, thereby promoting leakage of bacterial cell contents and a breakdown of the transmembrane potential; wherein the co-targeting pharmacological agent inhibits bacteria protease Peptide Deformylase, that catalyzes the removal of formyl groups from the N-termini of newly synthesized bacterial polypeptides; and wherein the co-targeting pharmacological agent inhibits two-component regulatory systems in bacteria, such as the ability to respond to their environment through signal transduction across bacterial plasma membranes, these signal transduction processes being absent in mammalian membranes.

As used herein, the term "proton-motive force ($\Delta p$)" refers to the storing of energy (acting like a kind of battery), as a combination of a proton and voltage gradient across a membrane. The two components of $\Delta p$ are $\Delta\Psi$ (the transmembrane potential) and $\Delta pH$ (the chemical gradient of $H^+$). Stated another way, $\Delta p$ consists of the $H^+$ transmembrane potential $\Delta\Psi$ (negative (acidic) outside) and a transmembrane pH gradient $\Delta pH$ (alkaline inside). This potential energy stored in the form of an electrochemical gradient, is generated by the pumping of hydrogen ions across biological membranes (mitochondrial inner membranes or bacterial and fungal plasma membranes) during chemiosmosis. The $\Delta p$ can be used for chemical, osmotic, or mechanical work in the cells. The proton gradient is generally used in oxidative phosphorylation to drive ATP synthesis and can be used to drive efflux pumps in bacteria, fungi, or mammalian cells including cancerous cells. $\Delta p$ will be used herein to describe four (4) different proton motive forces in membranes, based on species, and is mathematically defined as ($\Delta P = \Delta\Psi + \Delta pH$).

1) Mammalian Mitochondrial Proton-motive force ($\Delta p$-mito-mam)
2) Fungal Mitochondrial Proton-motive force ($\Delta p$-mito-Fungi)
3) Fungal Plasma Membrane Proton-motive force ($\Delta p$-plas-Fungi)
4) Bacterial Plasma Membrane Proton-motive force ($\Delta p$-plas-Bact)

As used herein, the term "Bacterial Plasma Membrane Proton-motive force ($\Delta p$-plas-Bact)" refers to the potential energy stored in the form of an electrochemical gradient ($H^+$), across a bacterial plasma membrane, and is generated by the pumping of hydrogen ions across the plasma membrane during chemiosmosis. Δp-plas-Bact is used in oxidative phosphorylation to drive ATP synthesis in the bacterial plasma membrane and can be used to drive efflux pumps in bacterial cells.

As used herein, the term "phosphorylation potential (ΔGp)" refers to the AG for ATP synthesis at any given ATP, ADP and Pi concentrations (dimensions: kJ mol$^{-1}$).

As used herein the term "CCCP" refers to carbonyl cyanide m-chlorophenylhydrazone, a highly toxic ionophore and uncoupler of the respiratory chain. CCCP increases the conductance of protons through membranes and acts as a classical uncoupler by uncoupling ATP synthesis from the ΔμH$^+$ and dissipating both the ΔΨ and ΔpH.

As used herein, the term "Reactive Oxygen Species", includes one of the following categories:
a) The Superoxide ion radical ($O_2^-$)
b) Hydrogen Peroxide (non-radical) ($H_2O_2$)
c) Hydroxyl radical (*OH)
d) Hydroxy ion (OH$^-$)
These ROS generally occur through the reaction chain:

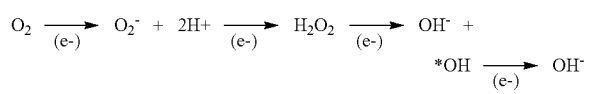

As used herein, the term "singlet oxygen" refers to ("$1O_2$") and is formed via an interaction with triplet-excited molecules. Singlet oxygen is a non-radical species with its electrons in anti-parallel spins. Because singlet oxygen $1O_2$ does not have spin restriction of its electrons, it has a very high oxidizing power and is easily able to attack membranes (e.g., via polyunsaturated fatty acids, or PUFAs) amino acid residues, protein and DNA.

As used herein, the term "NIMELS effect" refers to the modification of the bioenergetic "state" of irradiated cells at the level of the cell's plasma and mitochondrial membranes from ΔΨ-steady to ΔΨ-trans with the present invention. Specifically, the NIMELS effect can weaken cellular anabolic pathways or antimicrobial and/or cancer resistance mechanisms that make use of the proton motive force or the chemiosmotic potential for their energy needs.

As used herein, the term "periplasmic space or periplasm" refers to the space between the plasma membrane and the outer membrane in gram-negative bacteria and the space between the plasma membrane and the cell wall in gram-positive bacteria and fungi such as the *Candida* and *Trichophyton* species. This periplasmic space is involved in various biochemical pathways including nutrient acquisition, synthesis of peptidoglycan, electron transport, and alteration of substances toxic to the cell. In gram-positive bacteria like MRSA, the periplasmic space is of significant clinical importance as it is where β-lactamase enzymes inactivate penicillin based antibiotics.

As used herein, the term "efflux pump" refers to an active transport protein assembly which exports molecules from the cytoplasm or periplasm of a cell (such as antibiotics, antifungals, or poisons) for their removal from the cells to the external environment in an energy dependent fashion.

As used herein, the term "efflux pump inhibitor" refers to a compound or electromagnetic radiation delivery system and method which interferes with the ability of an efflux pump to export molecules from a cell. In particular, the efflux pump inhibitor of this invention is a form of electromagnetic radiation that will interfere with a pump's ability to excrete therapeutic antibiotics, anti-fungal agents, antineoplastic agents and poisons from cells via a modification of the ΔΨ-steady-mam, ΔΨ-steady-fungi or, ΔΨ-steady-bact.

By a cell that "utilizes an efflux pump resistance mechanism," it is meant that the bacterial cell exports anti-bacterial agents from their cytoplasm or periplasm to the external environment of the cell and thereby reduce the concentration of these agents in the cell to a concentration below what is necessary to inhibit the growth and/or proliferation of the bacterial cells.

As used herein, the term "anti-bacterial molecule (or agent)" refers to a chemical or compound that is bacteriacidal or bacteriastatic. Another principal efficacy resides in the present invention's ability to potentiate anti-bacterial molecules by inhibiting efflux pump activity in resistant bacterial strains, or inhibiting anabolic reactions and/or resistance mechanisms that require the proton motive force or chemiosmotic potential for energy.

As used herein, a "sub-inhibitory concentration" of an antibacterial agent refers to a concentration that is less than that required to inhibit a majority of the target cells in the population. Generally, a sub-inhibitory concentration refers to a concentration that is less than the Minimum Inhibitory Concentration (MIC).

As used herein, the term "Minimal Inhibitory Concentration" or MIC is defined as the lowest effective or therapeutic concentration that results in inhibition of growth of the microorganism. The minimum inhibitory concentration (MIC) of an antibacterial agent is therefore the maximum dilution of the agent that will still inhibit the growth of a test microorganism. The minimum bactericidal concentration (MBCs) of an antibacterial agent is the lowest concentration of the antimicrobial agent that will prevent the growth of an organism after subculture on to antibiotic-free media. The minimum lethal concentration (MLC) of an antibacterial agent is the maximum dilution of the product that will kill the test organism. MIC/MLC values can be determined by a number of standard test procedures. The most commonly employed methods are the tube dilution method and agar dilution methods. Serial dilutions are made of the products in bacterial growth media. The test organisms are then added to the dilutions of the products, incubated, and scored for growth. This procedure is a standard assay for antimicrobials. The procedure incorporates the content and intent of the American Society for Microbiology (ASM) recommended methodology.

As used herein, the term "therapeutically effective amount" of an antibacterial agent refers to a concentration of an agent that will partially or completely relieve one or more of the symptoms caused by the target (pathogenic) cells. In particular, a therapeutically effective amount refers to the amount of an agent that: (1) reduces, if not eliminates, the population of target microbial cells in the patient's body, (2) inhibits (i.e., slows, if not stops) proliferation of the target microbial cells in the patients body, (3) inhibits (i.e., slows, if not stops) spread of the infection (4) relieves (if not, eliminates) symptoms associated with the infection. The NIMELS effect lowers the therapeutic threshold by sensitizing the microbial targets to the antibiotic agent.

As used herein, the term "Interaction coefficient" is defined as a numerical representation of the magnitude of the bacteriastatic/bacteriacidal interaction between the NIMELS laser and/or the antimicrobial molecule, with the target cells.

Thermodynamics of Energy Transduction in Biological Membranes

The present invention is directed to perturbing cell membrane biological thermodynamics (bioenergetics) and the consequent diminished capacity of the irradiated cells to adequately undergo normal energy transduction and energy transformation.

The methods and systems of the present invention optically alter and modify $\Psi$d-plas-mam, $\Psi$d-mito-mam, $\Psi$d-plas-fungi, $\Psi$d-mito-fungi and $\Psi$d-plas-bact to set in motion further alterations of $\Delta\Psi$ and $\Delta$p in the same membranes. This is caused by the targeted near infrared irradiation of the C—H covalent bonds in the long chain fatty acids of lipid bilayers, causing a variation in the dipole potential $\Psi$d.

Figure 2:
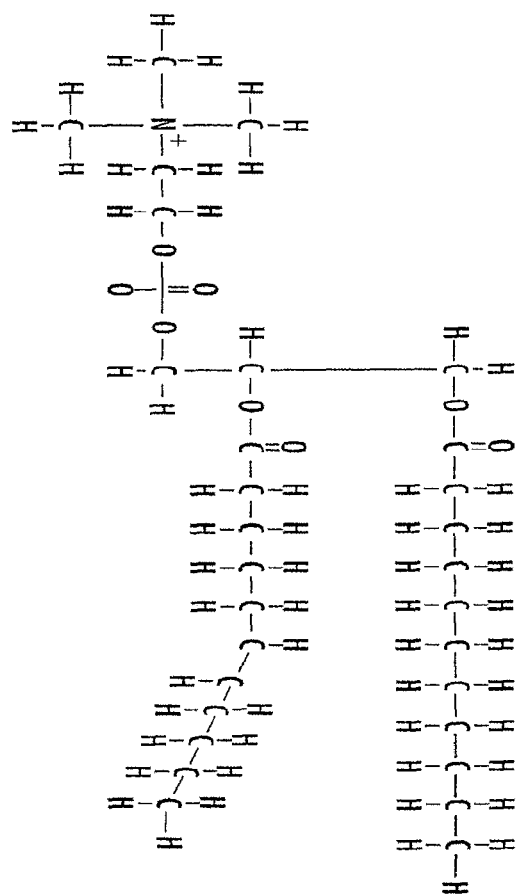
FIG. 2 shows the chemical structure of a phospholipid.
Figure 3:
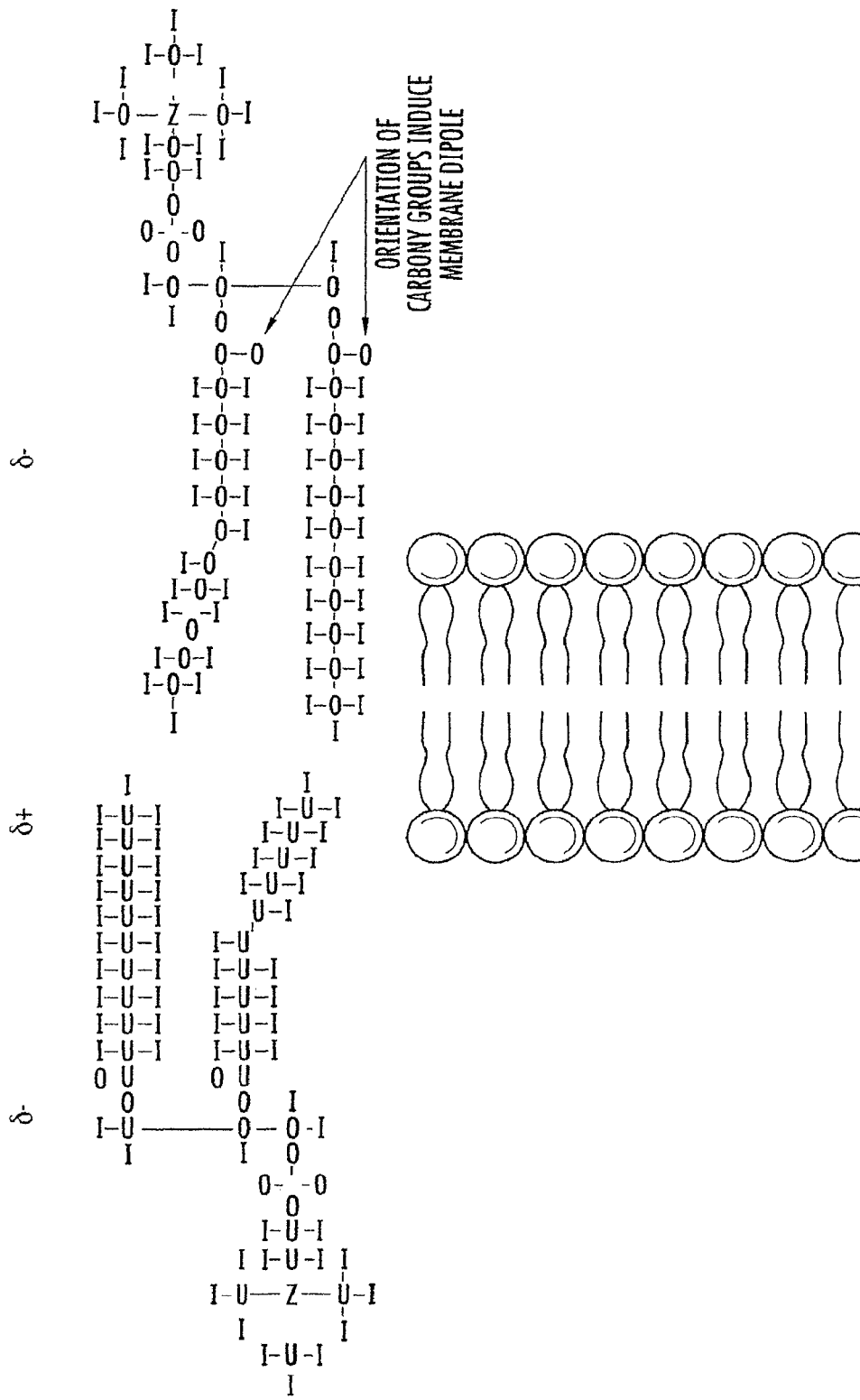
FIG. 3 shows dipole effects in phospholipid bilayer membranes ($\Psi d$)
Figure 4A:
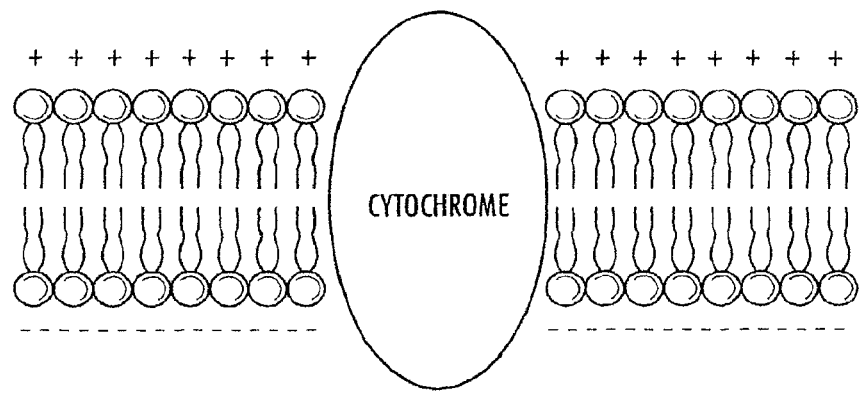
FIG. 4A shows a phospholipid bilayer in bacterial plasma membrane, mammalian mitochondrial membrane, or fugal mitochondrial membrane with a steady-state trans-membrane potential prior to NIMELS irradiation.

To aid with an understanding of the process of this bioenergetic modification, the following description of the application of thermodynamics to membrane bioenergetics and energy transduction in biological membranes is presented. To begin, membranes (lipid bilayers, see, FIG. 1) possess a significant dipole potential $\Psi$d arising from the structural association of dipolar groups and molecules, primarily the ester linkages of the phospholipids (FIG. 2) and water. These dipolar groups are oriented such that the hydrocarbon phase is positive with respect to the outer membrane regions (FIG. 3). The degree of the dipole potential is usually large, typically several hundreds of millivolts. The second major potential, a separation of charge across the membrane, gives rise to the trans-membrane potential $\Delta\Psi$. The trans-membrane potential is defined as the electric potential difference between the bulk aqueous phases at the two sides of the membrane and results from the selective transport of charged molecules across the membrane. As a rule, the potential at the cytoplasm side of cell membranes is negative relative to the extracellular physiological solution (FIG. 4A).

The dipole potential $\Psi$d constitutes a large and functionally important part of the electrostatic potential of all plasma and mitochondrial membranes. $\Psi$d modifies the electric field inside the membrane, producing a virtual positive charge in the apolar bilayer center. As a result of this "positive charge", lipid membranes exhibit a substantial (e.g., up to six orders of magnitude) difference in the penetration rates between positively and negatively charged hydrophobic ions. $\Psi$d also plays an important role in the membrane permeability for lipophilic ions.

Figure 4B:
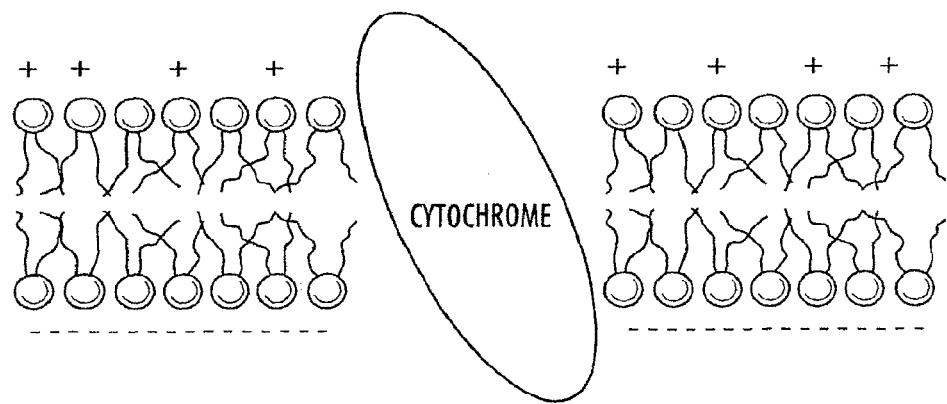
FIG. 4B shows a transient-state plasma membrane potential in bacterial plasma membrane, mammalian mitochondrial membrane, or fugal mitochondrial membrane after NIMELS irradiation.
Figure 5:
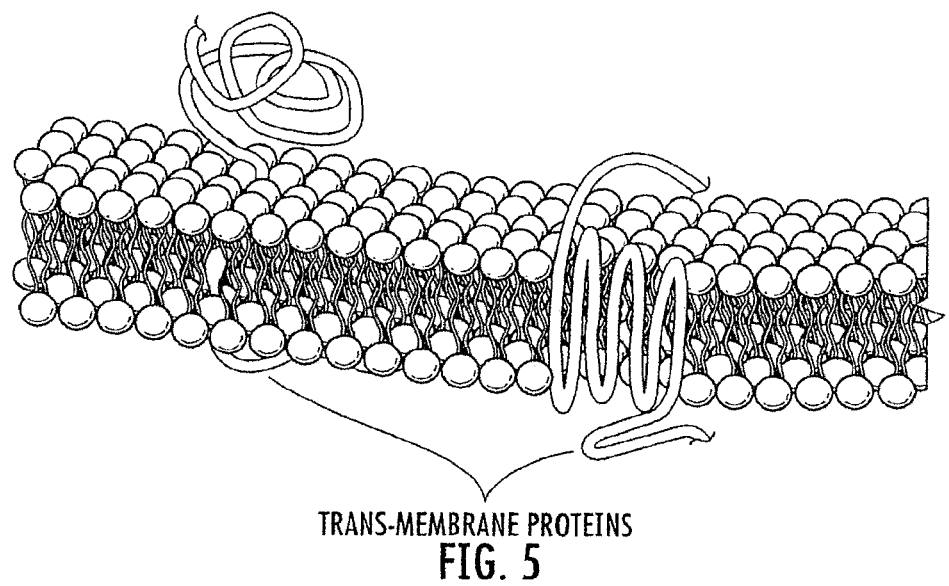
FIG. 5 shows a phospholipid bilayer with trans-membrane proteins embedded therein.

Numerous cellular processes, such as binding and insertion of proteins (enzymes), lateral diffusion of proteins, ligand-receptor recognition, and certain steps in membrane fusion to endogenous and exogenous molecules, critically depend on the physical properties $\Psi$d of the membrane bilayer. Studies in model membrane systems have illustrated the ability of mono- and multivalent ions to cause isothermal phase transitions in pure lipids, different phase separations, and a distinct clustering of individual components in mixtures. In membranes, changes such as these can exert physical influences on the conformational dynamics of membrane-embedded proteins (FIGS. 4B and 5), and more specifically, on proteins that go through large conformational rearrangements in their transmembrane domains during their operating cycles. Most importantly, changes in $\Psi$d is believed to modulate membrane enzyme activities.

Energy Transduction

The energy transduction in biological membranes generally involves three interrelated mechanisms:

1) The transduction of redox energy to "free energy" stored in a trans-membrane ionic electrochemical potential also called the membrane proton electrochemical gradient $\Delta\mu H^+$. This proton electrochemical potential difference between the two sides of a membrane that engage in active transport involving proton pumps is at times also called a chemiosmotic potential or proton motive force.

2) In mammalian cells, the ($Na^+$) ion electrochemical gradient $\Delta\mu x^+$ is maintained across the plasma membrane by active transport of ($Na^+$) out of the cell. This is a different gradient than the proton electrochemical potential, yet is generated from a (pump) via the ATP produced during oxidative phosphorylation from the Mammalian Mitochondrial Proton-motive force $\Delta$p-mito-mam.

3) The use of this "free energy" to create ATP (energy transformation) to impel active transport across membranes with the concomitant buildup of required solutes and metabolites in the cell is termed the phosphorylation potential $\Delta$Gp. In other words, $\Delta$Gp is the $\Delta$G for ATP synthesis at any given set of ATP, ADP and $P_i$ concentrations.

Steady-State Trans-Membrane Potential ($\Delta\Psi$-Steady)

The state of a membrane "system" is in equilibrium when the values of its chemical potential gradient $\Delta\mu H^+$ and E (energy) are temporally independent and there is no flux of energy across the margins of the system. If the membrane system variables of $\Delta\mu H+$ and E are constant, but there is a net flux of energy moving across the system, then this membrane system is in a steady-state and is temporally dependent.

It is this temporally dependent steady-state trans-membrane and/or mitochondrial potential ($\Delta\Psi$-steady) of a cell (a respiring, growing and dividing cell) that is of focus. This "steady-state" of the flow of electrons and protons, or $Na^+/K^+$ ions across a mitochondrial or plasma membrane during normal electron transport and oxidative phosphorylation, would most likely continue into the future, if unimpeded by an endogenous or exogenous event. Any exogenous modification of the membrane thermodynamics, would bring about a transient-state trans-membrane and/or mitochondrial potential $\Delta\Psi$-trans, and this change from $\Delta\Psi$-steady to $\Delta\Psi$-trans is an object of the present invention.

Mathematical relationships between the state variables $\Delta\Psi$-steady and $\Delta\Psi$-trans are called equations of state. In thermodynamics, a state function (state quantity), is a property or a system that depends only on the current state of the system. It does not depend on the way in which the system attained its particular state. The present invention facilitates a transition of state in a trans-membrane and/or mitochondrial potential $\Delta\Psi$, in a temporally dependent manner, to move the bioenergetics of a membrane from a thermodynamic steady-state condition $\Delta\Psi$-steady to one of energy stress and/or redox stress in a transition state $\Delta\Psi$-trans.

This can occur in $\Delta\Psi$-steady-mam, $\Delta\Psi$-steady-fungi, $\Delta\Psi$-steady-Bact-$\Delta\Psi$-steady-mito-mam and $\Delta\Psi$-steady-mito-fungi. Not wishing to be bound by theory, it is believed that this transition is caused by the targeted near infrared irradiation of the C—H covalent bonds in the long chain fatty acids of lipid bilayers (with 930 nm wavelength), causing a variation in the dipole potential $\Psi$d, and the targeted near infrared irradiation of cytochrome chains (with $\lambda$ of 870 nm), that will concurrently alter $\Delta\Psi$-steady and the redox potential of the membranes.

The First Law of Thermodynamics and Membranes

An elemental aspect of the First Law of Thermodynamics (which holds true for membrane systems) is that the energy of an insulated system is conserved and that heat and work are both considered as equivalent forms of energy. Hence, the energy level of a membrane system ($\Psi$d and $\Delta\Psi$) can be altered by an increase or decrease of mechanical work exerted by a force or pressure acting, respectively, over a given distance or within an element of volume; and/or non-destructive heat transmitted through a temperature gradient in the membrane.

This law (the law of conservation of energy), posits that the total energy of a system insulated from its surroundings does not change. Thus, addition of any amounts of (energy) heat and work to a system must be reflected in a change of the energy of the system.

Absorption of Infrared Radiation

The individual photons of infrared radiation do not contain sufficient energy (e.g., as measured in electron-volts) to induce electronic transitions (in molecules) as is seen with photons of ultraviolet radiation. Because of this, absorption of infrared radiation is limited to compounds with small energy differences in the possible vibrational and rotational states of the molecular bonds.

By definition, for a membrane bilayer to absorb infrared radiation, the vibrations or rotations within the lipid bilayer's molecular bonds that absorb the infrared photons, must cause a net change in the dipole potential of the membrane. If the frequency (wavelength) of the infrared radiation matches the vibrational frequency of the absorbing molecule (i.e., C—H covalent bonds in long chain fatty acids) then radiation will be absorbed causing a change in $\Psi d$. This can happen in $\Psi d$-plas-mam, $\Psi d$-mito-mam, $\Psi d$-plas-fungi, $\Psi d$-mito-fungi and $\Psi d$-plas-bact. In other words, there can be a direct and targeted change in the enthalpy and entropy ($\Delta H$ and $\Delta S$) of all cellular lipid bilayers with the methods and systems described herein.

The present invention is based upon a combination of insights that have been introduced above and are derived in part from empirical data, which include the following:

It has been appreciated that unique, single infrared wavelengths (about 870 nm and about 930 nm) are each capable of killing bacterial cells (prokaryotes) such as E. coli and (eukaryotes) such as Chinese Hampster Ovary (CHO) cells, as a result of the generation and interaction of ROS and/or toxic singlet oxygen reactions. The present invention employs these infrared wavelengths, preferably in combination, but at 5 log less power density than is typically found in a confocal laser microscope such as that used in optical traps (~ to 500,000 w/cm$^2$ less power) to advantageously exploit the use of such wavelengths for therapeutic laser systems, to cause a bacteriostatic or bacteriocidal effect at an infection site, without causing thermal damage to the hosts tissues.

This is done for the expressed purpose of alteration, manipulation and depolarization of the $\Delta\Psi$-steady-mam, $\Delta\Psi$-steady-fungi, $\Delta\Psi$-steady-Bact, $\Delta\Psi$-steady-mito-mam and $\Delta\Psi$-steady-mito-fungi of all cells within the irradiation field. This is accomplished in the present invention by the targeted near infrared irradiation of the C—H covalent bonds in the long chain fatty acids of lipid bilayers (with 930 nm energy), resulting in a variation in the dipole potentials $\Psi d$-plas-mam, $\Psi d$-mito-mam, $\Psi d$-plas-fungi, $\Psi d$-mito-fungi and $\Psi d$-plas-bact of all biological membranes within the irradiation field. Secondly, the near infrared irradiation of cytochrome chains (with 870 nm), will additionally alter $\Delta\Psi$-steady and the redox potential of the membranes that have cytochromes (i.e., bacterial plasma membranes, and fungal and mammalian mitochondria).

Serving as direct chromophores (cytochromes and C—H bonds in long chain fatty acids), there will be a direct enthalpy and entropy change in the molecular dynamics of membrane lipids and cytochromes for all cellular lipid bilayers in the irradiation path of the present invention. This will alter each membrane dipole potential $\Psi d$, and concurrently alter the absolute value of the membrane potential $\Delta\Psi$, of all membranes in the irradiated cells.

These changes occur through significantly increased molecular motions (viz. $\Delta S$) of the lipids and metallo-protein reaction centers of the cytochromes, as they absorb energy from the NIMELS system in a linear one-photon process. As even a small thermodynamic shift in either the lipid bilayer and/or the cytochromes would be enough to change the dipole potential $\Psi d$, the molecular shape (and hence the enzymatic reactivity) of an attached electron transport protein, or transmembrane protein would be rendered less functional. This will directly affect and modify the $\Delta\Psi$ in all membranes in the irradiated cells.

The NIMELS effect occurs in accordance with methods and systems described herein, importantly, without thermal or ablative mechanical damage to the cell membranes. This combined and targeted low dose irradiation approach is a distinct variation and improvement from existing methods that would otherwise cause actual thermal or mechanical damage to all membranes within the path of a beam of energy.

Membrane Entropy and the Second Law of Thermodynamics

The conversion of heat into other forms of energy is never perfect, and (according to the Second Law of Thermodynamics) must always be accompanied by an increase in entropy. Entropy (in a membrane) is a state function whose change in a reaction describes the direction of a reaction due to changes in (energy) heat input or output and the associated molecular rearrangements.

Even though heat and mechanical energy are equivalent in their fundamental nature (as forms of energy), there are limitations on the ability to convert heat energy into work. i.e., too much heat can permanently damage the membrane architecture and prevent work or beneficial energy changes in either direction.

Figure 6:
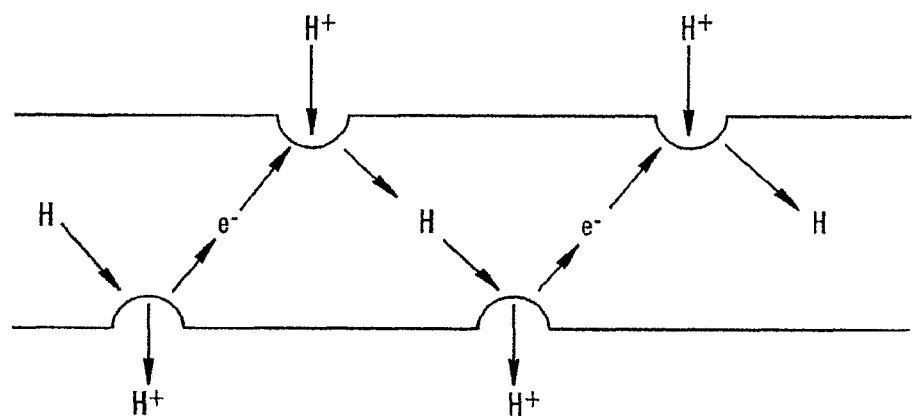
FIG. 6 shows a general depiction of electron transport and proton pump.
Figure 7:
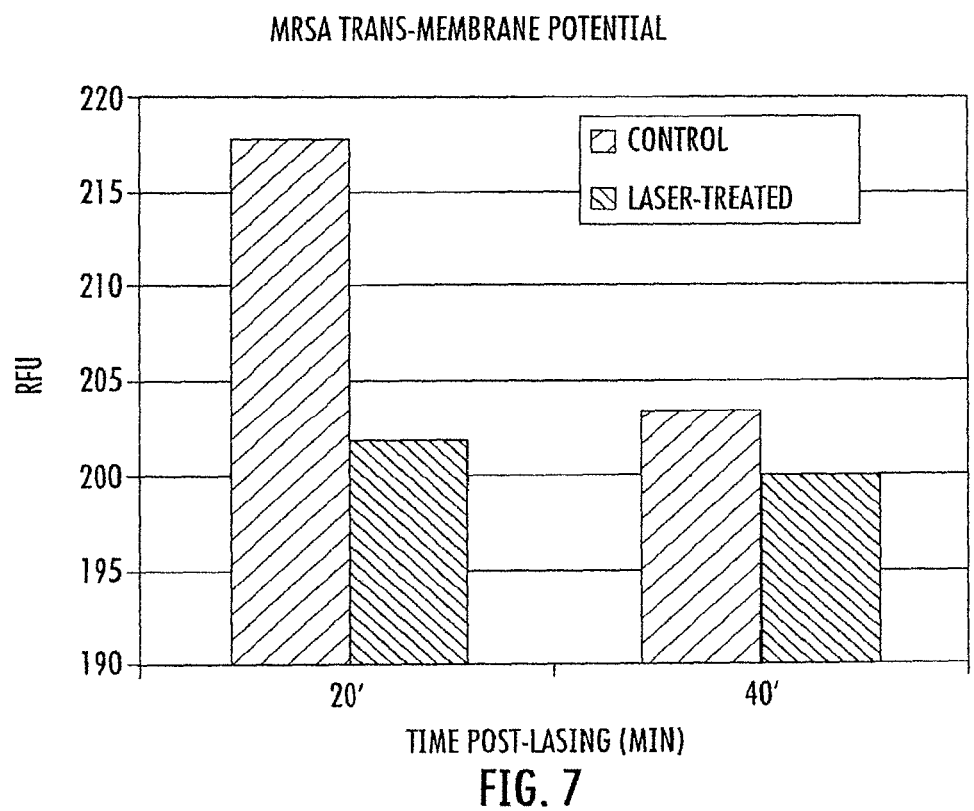
FIG. 7 shows the effects of NIMELS irradiation (at a single dosimetry) on MRSA trans-membrane potential which is measured by green fluorescence emission intensities in control and lased samples as a function of time in minutes post-lasing.

The NIMELS effect will modify the entropy "state" of irradiated cells at the level of the lipid bilayer in a temporally dependent manner. This increase in entropy will alter the Yd of all irradiated membranes (mitochondrial and plasma) and hence, thermodynamically alter the "steady-state" flow of electrons and protons across a cell membrane (FIGS. 6 and 7). This will in turn change the steady-state trans-membrane potential $\Delta\Psi$-steady to a transient-state membrane potential ($\Delta\Psi$-tran). This phenomenon will occur in:

1) Mammalian Plasma Trans-membrane Potential $\Delta\Psi$-plas-mam;
2) Fungal Plasma Trans-membrane Potential $\Delta\Psi$-plas-fungi;
3) Bacterial Plasma Trans-membrane Potential $\Delta\Psi$-plas-bact;
4) Mammalian Mitochondrial Trans-membrane Potential $\Delta\Psi$-mito-mam; and
5) Fungal Mitochondrial Trans-membrane Potential $\Delta\Psi$-mito-fungi.

This is a direct result of the targeted enthalpy change at the level of the C—H bonds of the long chain fatty acids in the fluid mosaic membrane, causing a measure of dynamic disorder (in the membrane) which can alter the membranes corporeal properties. This fluid mosaic increases in entropy and can disrupt the tertiary and quaternary properties of electron transport proteins, cause redox stress, energy stress and subsequent generation of ROS, that will further damage membranes and additionally alter the bioenergetics.

Since a prime function of the electron transport system of respiring cells is to transduce energy under steady-state conditions, techniques according to the present invention are utilized to temporarily, mechano-optically uncouple many of the relevant thermodynamic interactions on that transduction process. This can be done with the express intent of altering the absolute quantitative value of the proton electrochemical gradient $\Delta\mu H^+$ and proton-motive force and $\Delta p$ of the membranes. This phenomenon can occur, inter alia, in:

1) Mammalian Mitochondrial Proton-motive force (Δp-mito-mam);
2) Fungal Mitochondrial Proton-motive force (Δp-mito-Fungi);
3) Fungal Plasma Membrane Proton-motive force (Δp-plas-Fungi); and
4) Bacterial Plasma Membrane Proton-motive force (Δp-plas-Bact).

Such phenomena can in turn decrease the Gibbs free energy value ΔG available for the phosphorylation and synthesis of ATP (ΔGp). The present invention carries out these phenomena in order to inhibit the necessary energy dependent anabolic reactions, potentiating pharmacological therapies, and/or lowering cellular resistance mechanisms (to antimicrobial, antifungal and antineoplastic molecules) as many of these resistance mechanisms make use of the proton motive force or the chemiosmotic potential for their energy needs, to resist and/or efflux these molecules.

Free Radical Generation in Consequence of Modifications of ΔΨ-Steady

The action of chemical uncouplers for oxidative phosphorylation and other bioenergetic work is believed to depend on the energized state of the membrane (plasma or mitochondrial). Further, it is believed that the energized state of the bacterial membrane or eukaryotic mitochondrial inner membrane, is an electrochemical proton gradient $\Delta\mu H^+$ that is established by primary proton translocation events occurring during cellular respiration and electron transport.

Agents that directly dissipate (depolarize) the $\Delta\mu H^+$, (e.g., by permeabilizing the coupling membrane to the movement of protons or compensatory ions) short-circuits energy coupling, and inhibit bioenergetic work, by inducing a reduction in the membrane potential ΔΨ-steady. This will occur while respiration (primary proton translocation) continues apace.

For example, the classic uncoupler of oxidative phosphorylation, carbonyl cyanide m-chlorophenylhydrazone (CCCP), induces a reduction in membrane potential ΔΨ-steady and induces a concomitant generation of ROS, as respiration continues. These agents (uncouplers) generally cannot be used as antimicrobials, antifungals, or antineoplastics, because their effects are correspondingly toxic to all bacterial, fungal and mammalian cells.

However, it has been shown that in many target cells that are resistant to antimicrobials a Δp uncoupler (like CCCP) will collapse the energy gradient required for an efflux pump and hence induce a strong increase in the intracellular accumulation of these drugs. These results clearly indicate that some resistance mechanisms (such as drug efflux pumps) are driven by the proton motive force.

The scientific findings and experimental data of the present invention show that as a membrane is depolarized optically, the generation of ROS further potentiates the depolarization of affected cells, and further potentiate the antibacterial effects of the present invention.

Free Radical and ROS Generation by Irradiation with the NIMELS Laser

By mechano-optically modifying many of the relevant thermodynamic interactions of the membrane energy transduction process, along with altering ΔΨ-steady, the present invention can act as an optical uncoupler by lowering the $\Delta\mu H^+$ and Δp of the following irradiated membranes:
1) Mammalian Mitochondrial Proton-motive force (Δp-mito-mam)
2) Fungal Mitochondrial Proton-motive force (Δp-mito-Fungi)
3) Fungal Plasma Membrane Proton-motive force (Δp-plas-Fungi)
4) Bacterial Plasma Membrane Proton-motive force (Δp-plas-Bact)

This lowered Δp will cause a series of free radicals and radical oxygen species to be generated because of the altered redox state. The generation of free radicals and reactive oxygen species has been proven experimentally and described herein with the alteration of ΔΨ-steady to ΔΨ-trans in the following:
1) ΔΨ-steady-mam+(NIMELS Treatment)→→ΔΨ-trans-mam
2) ΔΨ-steady-fungi+(NIMELS Treatment)→→ΔΨ-trans-fungi
3) ΔΨ-steady-bact+(NIMELS Treatment)→→ΔΨ-trans-bact
4) ΔΨ-mito-fungi+(NIMELS Treatment)→→ΔΨ-trans-mito-fungi
5) ΔΨ-mito-mam+(NIMELS Treatment)→→ΔΨ-trans-mito-mam The altered redox state and generation of free radicals and ROS because of the ΔΨ-steady+(NIMELS Treatment) →→ΔΨ-trans phenomenon, can cause serious further damage to biological membranes such as lipid peroxidation.

Lipid Peroxidation

Lipid peroxidation is a prevalent cause of biological cell injury and death in both the microbial and mammalian world. In this process, strong oxidants cause the breakdown of membrane phospholipids that contain polyunsaturated fatty acids (PUFA's). The severity of the membrane damage can cause local reductions in membrane fluidity and full disruption of bilayer integrity.

Peroxidation of mitochondrial membranes (mammalian cells and fungi) will have detrimental consequences on the respiratory chains resulting in inadequate production of ATP and collapse of the cellular energy cycle. Peroxidation of the plasma membrane (bacteria) can affect membrane permeability, disfunction of membrane proteins such as porins and efflux pumps, inhibition of signal transduction and improper cellular respiration and ATP formation (i.e., the respiratory chains in prokaryotes are housed in the plasma membranes as prokaryotes do not have mitochondria).

Free Radical

A free radical is defined as an atom or molecule that contains an unpaired electron. An example of the damage that a free radical can do in a biological environment is the one-electron (via an existing or generated free radical) removal from bis-allylic C—H bonds of polyunsaturated fatty acids (PUFAs) that will yield a carbon centered free radical. R*+ (PUFA)-CH(bis-allylic C—H bond)→(PUFA)-C*+RH This reaction can initiate lipid peroxidation damage of biological membranes. A free radical can also add to a nonradical molecule, producing a free radical product. (A*+ B→A-B*) or a nonradical product (A*+B→A-B)

An example of this would be the hydroxylation of an aromatic compound by *OH.

Reactive Oxygen Species (ROS)

Oxygen gas is actually a free radical species. However, because it contains two unpaired electrons in different π-antibonding orbitals that have parallel spin in the ground state, the (spin restriction) rule generally prevents $O_2$ from receiving a pair of electrons with parallel spins without a catalyst. Consequently $O_2$ must receive one electron at a time.

There are many significant donors in a cell (prokaryotic and eukaryotic) that are able to stimulate the one-electron reduction of oxygen, that will create an additional radical species.

These are generally categorized as:
The Superoxide ion radical ($O_2^-$)
Hydrogen Peroxide (non-radical) ($H_2O_2$)
Hydroxyl radical (*OH)
Hydroxy ion ($OH^-$)
The Reaction Chain is:

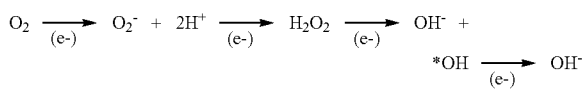

Superoxide

The danger of these molecules to cells is well categorized in the literature. Superoxide, for example, can either act as an oxidizing or a reducing agent. $NADH \rightarrow NAD^+$ Of higher importance to an organism's metabolism, superoxide can reduce cytochrome C. It is generally believed that the reaction rates of superoxide ($O_2^-$) with lipids (i.e., membranes) proteins, and DNA are too slow to have biological significance. The protonated form of superoxide hydroperoxyl radical (HOO*) has a lower reduction potential than ($O_2^-$), yet is able to remove hydrogen atoms from PUFA's. Also of note, the pKa value of (HOO*) is 4.8 and the (acid) microenvironment near biological membranes will favor the formation of hydroperoxyl radicals. Furthermore, the reaction of superoxide ($O_2^-$) with any free $F_e^{+3}$ will produce a "perferryl" intermediate which can also react with PUFA's and induce lipid (membrane) peroxidation.

Hydrogen Peroxide

Hydrogen peroxide ($H_2O_2$) is not a good oxidizing agent (by itself) and cannot remove hydrogen from PUFA's. It can, however, cross biological membranes (rather easily) to exert dangerous and harmful effects in other areas of cells. For example, ($H_2O_2$) is highly reactive with transition metals inside microcellular environments, (such as $Fe^{+2}$ and $Cu^+$) that can then create hydroxyl radicals (*OH) (known as the Fenton Reaction). An hydroxyl radical is one of the most reactive species known in biology.

Hydroxyl Radical

Hydroxyl radicals (*OH) will react with almost all kinds of biological molecules. It has a very fast reaction rate that is essentially controlled by the hydroxyl radical (*OH) diffusion rate and the presence (or absence) of a molecule to react near the site of (*OH) creation. In fact, the standard reduction potential (E0') for hydroxyl radical (*OH) is (+2.31 V) a value that is $7_x$ greater than ($H_2O_2$), and is categorized as the most reactive among the biologically relevant free radicals. Hydroxyl radicals will initiate lipid peroxidation in biological membranes, in addition to damaging proteins and DNA.

Reactive Oxygen Species Created from the Peroxidation of PUFAs

Furthermore, the development of lipid peroxidation (from any source) will result in the genesis of three other reactive oxygen intermediate molecules from PUFA's.
(a) alkyl hydroperoxides (ROOH);
Like $H_2O_2$, alkyl hydroperoxides are not technically radical species but are unstable in the presence of transition metals such as such as $Fe^{+2}$ and $Cu^+$.
(b) alkyl peroxyl radicals (ROO*); and
(c) alkoxyl radicals (RO*).

Alkyl peroxyl radicals and alkoxyl radicles are extremely reactive oxygen species and also contribute to the process of propagation of further lipid peroxidation. The altered redox state of irradiated cells and generation of free radicals and ROS because of the $\Delta\Psi$-steady+(NIMELS Treatment) $\rightarrow\rightarrow\Delta\Psi$-trans phenomenon is another object of the present invention. This is an additive effect to further alter cellular bioenergetics and inhibit necessary energy dependent anabolic reactions, potentiate pharmacological therapies, and/or lower cellular resistance mechanisms to antimicrobial, antifungal and antineoplastic molecules.

ROS overproduction can damage cellular macromolecules, above all lipids. Lipid oxidation has been shown to modify both the small-scale structural dynamics of biological membranes as well as their more macroscopic lateral organization and altered a packing density dependent reorientation of the component of the dipole moment $\Psi$d. Oxidative damage of the acyl chains (in lipids) causes loss of double bonds, chain shortening, and the introduction of hydroperoxy groups. Hence, these changes are believed to affect the structural characteristics and dynamics of lipid bilayers and the dipole potential $\Psi$d.

Antimicrobial Resistance

Antimicrobial resistance is defined as the ability of a microorganism to survive the effects of an antimicrobial drug or molecule. Antimicrobial resistance can evolve naturally via natural selection, through a random mutation, or through genetic engineering. Also, microbes can transfer resistance genes between one another via mechanisms such as plasmid exchange. If a microorganism carries several resistance genes, it is called multi-drug resistant or, colloquially, a "superbug."

Multi-drug resistance in pathogenic bacteria and fungi are a serious problem in the treatment of patients infected with such organisms. At present, it is tremendously expensive and difficult to create or discover new antimicrobial drugs that are safe for human use. Also, there have been resistant mutant organisms that have evolved challenging all known antimicrobial classes and mechanisms. Hence, few antimicrobials have been able to maintain their long-term effectiveness. Most of the mechanisms of antimicrobial drug resistance are known.

The four main mechanisms by which micro-organisms exhibit resistance to antimicrobials are:
a) Drug inactivation or modification;
b) Alteration of target site;
c) Alteration of metabolic pathway; and
d) Reduced drug accumulation: by decreasing drug permeability and/or increasing active efflux on the cell surface.

Resistant Microbes

Staphylococcus aureus (S. aureus) is a good example of one of the major resistant bacterial pathogens currently plaguing humanity. This gram positive bacterium is primarily found on the mucous membranes and skin of close to half of the adult world-wide population. S. aureus is extremely adaptable to pressure from all known classes of antibiotics. S. aureus was the first bacterium in which resistance to penicillin was found in 1947. Since then, almost complete resistance has been found to methicillin and oxacillin. The "superbug" MRSA (methicillin resistant Staphylococcus aureus) was first detected in 1961, and is now ubiquitous in hospitals and communities worldwide. Today, more than half of all S. aureus infections in the United States are resistant to penicillin, methicillin, tetracycline and erythromycin. Recently, in what were the new classes of antibiotics (antimicrobials of last resort) glycopeptides and oxazolidinones, there have been reports of significant resistance (Vancomycin since 1996 and Zyvox since 2003).

A new variant CA-MRSA, (community acquired MRSA) has also recently emerged as an epidemic, and is responsible for a group of rapidly progressive, fatal diseases including necrotizing pneumonia, severe sepsis and necrotizing fasciitis. Outbreaks of community-associated (CA)-MRSA infections are reported daily in correctional facilities, athletic teams, military recruits, in newborn nurseries, and among active homosexual men. CA-MRSA infections now appear to be almost endemic in many urban regions and cause most CA-*S. aureus* infections.

The scientific and medical community has been attempting to find potentiators of existing antimicrobial drugs and inhibitors of drug resistance systems in bacteria and fungi. Such potentiators and/or inhibitors, if not toxic to humans, would be very valuable for the treatment of patients infected with pathogenic and drug-resistant microbes. In the United States, as many as 80% of individuals are colonized with *S. aureus* at some point. Most are colonized only intermittently; 20-30% are persistently colonized. Healthcare workers, persons with diabetes, and patients on dialysis all have higher rates of colonization. The anterior nares are the predominant site of colonization in adults; other potential sites of colonization include the axilla, rectum, and perineum.

Selective Pharmacological Alteration of $\Delta\Psi$-Steady State in Bacteria

There is a relatively new class of bactericidal antibiotics called the lipopeptides of which daptomycin is the first FDA approved member. This antibiotic has demonstrated (in vitro and in vivo) that it can rapidly kill virtually all clinically relevant gram-positive bacteria (such as MRSA) via a mechanism of action distinct from those of other antibiotics on the market at present.

Daptomycin's mechanism of action involves a calcium-dependent incorporation of the lipopeptide compound into the cytoplasmic membrane of bacteria. On a molecular level, it is calcium binding between two aspartate residues (in the daptomycin molecule) that decreases its net negative charge and permits it to act better with the negatively charged phospholipids that are typically found in the cytoplasmic membrane of gram-positive bacteria. There is generally no interaction with fungi or mammalian cells at therapeutic levels, so it is a very selective molecule.

The effects of daptomycin have been proposed to result from this calcium-dependent action on the bacterial cytoplasmic membrane that dissipates the transmembrane membrane electrical potential gradient $\Delta\mu H^+$. This is in effect, a selective chemical depolarization of only bacterial membranes. It is well known that the maintenance of a correctly energized cytoplasmic membrane is essential to the survival and growth of bacterial cells, nevertheless depolarization (in this manner) is not in and of itself a bacterially lethal action. For example, the antibiotic valinomycin, which causes depolarization in the presence of potassium ions, is bacteriostatic but not bactericidal as would be the case with CCCP.

Conversely, in the absence of a proton motive force $\Delta p$, the main component of which is the transmembrane electrical potential gradient $\Delta\mu H^+$, cells cannot make ATP or take up necessary nutrients needed for growth and reproduction. The collapse of $\Delta\mu H^+$ explains the dissimilar (detrimental) effects produced by daptomycin (e.g., inhibition of protein, RNA, DNA, peptidoglycan, lipoteichoic acid, and lipid biosynthesis).

Further research into the medical literature concerning the drug daptomycin, suggests that the addition of gentamicin or minocycline (to daptomycin) results in the enhancement of its bactericidal activity against MRSA. As both gentamicin and minocycline can be effluxed out of MRSA cells through energy dependent pumps, and are inhibitors of protein synthesis (an anabolic function) at the level of the 30S bacterial ribosome, this indicates that dissipation of the transmembrane electrical potential gradient $\Delta\mu H^+$ by daptomycin can potentiate certain antimicrobial drugs. This should occur as a result of resistance mechanisms that are rendered less useful by a reduction in the membrane potential $\Delta\Psi$ and the fact that ATP is not available (i.e., the concomitant lowered $\Delta Gp$) for the anabolic function of protein synthesis.

Based on the above, it would be possible to optically inhibit the activity of drug efflux pumps and/or anabolic reactions in target cells by safely reducing the membrane potential $\Delta\Psi$ ($\Delta\Psi$-steady+(NIMELS Treatment)→→$\Delta\Psi$-trans) of the cells in a given target area. Methods according to the present invention accomplish this and other tasks with the use of selected infrared wavelengths, e.g., about 870 nm and about 930 nm, independent of any exogenous chemical membrane-acting agents such as daptomycin.

Multidrug Resistance Efflux Pumps

Multidrug resistance efflux pumps are now known to be present in gram-positive bacteria, gram-negative bacteria, and other eukaryotic cells. Efflux pumps generally have a poly-specificity of transporters that confers a broad-spectrum of resistance mechanisms. These can strengthen the effects of other mechanisms of antimicrobial resistance such as mutations of the antimicrobial targets or enzymatic modification of the antimicrobial molecules. Active efflux for antimicrobials can be clinically relevant for β-lactam antimicrobials, macrolides, fluoroquinolones, tetracyclines and other important antibiotic families.

With efflux pump-based resistance, a microbe has the capacity to seize an antimicrobial agent or toxic compound and expel it to the exterior (environment) of the cell, thereby reducing the intracellular accumulation of the agent. It is generally considered that the over-expression of one or more of these efflux pumps prevents the intracellular accumulation of the agent to thresholds necessary for their biological activity. Universally in microbes, the efflux of drugs is coupled to the proton motive force that creates electrochemical potentials and/or the energy necessary (ATP) for the needs of these protein pumps. This includes:

1) Mammalian mitochondrial proton-motive force ($\Delta p$-mito-mam);
2) Fungal mitochondrial proton-motive force ($\Delta p$-mito-fungi);
3) Fungal plasma membrane proton-motive force ($\Delta p$-plas-fungi); and
4) Bacterial plasma membrane proton-motive force ($\Delta p$-plas-bact).

Phylogenetically, bacterial antibiotic efflux pumps belong to five superfamilies:

(i) ABC ($\Delta\Psi$-binding cassette), which are primary active transporters energized by ATP hydrolysis;
(ii) SMR [small multidrug resistance subfamily of the DMT (drug/metabolite transporters) superfamily];
(iii) MATE [multi-antimicrobial extrusion subfamily of the MOP (multidrug/oligosaccharidyl-lipid/polysaccharide flippases) superfamily];
(iv) MFS (major facilitator superfamily); and
(v) RND (resistance/nodulation/division superfamily), which are all secondary active transporters driven by ion gradients.

The approach of the current invention to inhibit efflux pumps is a general modification (optical depolarization) of the membranes $\Delta\Psi$ within the irradiated area, leading to lower electrochemical gradients that will lower the phosphorylation potential $\Delta Gp$ and energy available for the pumps functional energy needs. It is also the object of the present invention to have the same photobiological mechanism inhibit the many different anabolic and energy driven mechanisms of the target cells, including absorption of nutrients for normal growth.

Reduction of Efflux Pump Energy: Targeting the Driving Force of the Mechanism Today, there are no drugs that belong to the "energy-blocker" family of molecules that have been developed for clinical use as efflux pump inhibitors. There are a couple of molecules that have been found to be "general" inhibitors of efflux pumps. Two such molecules are reserpine and verapamil. These molecules were originally recognized as inhibitors of vesicular monoamine transporters and blockers of transmembrane calcium entry (or calcium ion antagonists), respectively. Verapamil is known as an inhibitor of MDR pumps in cancer cells and certain parasites and also improves the activity of tobramycin.

Reserpine inhibits the activity of Bmr and NorA, two gram-positive efflux pumps, by altering the generation of the membrane proton-motive force $\Delta p$ required for the function of MDR efflux pumps. Although these molecules are able to inhibit the ABC transporters involved in the extrusion of antibiotics (i.e., tetracycline), the concentrations necessary to block bacterial efflux are neurotoxic in humans.

Bacterial Plasma Trans-Membrane Potential $\Delta\Psi$-Plas-Bact and Cell Wall Synthesis During normal cellular metabolism, protons are extruded through the cytoplasmic membrane to form $\Delta\Psi$-plas-bact. This function also acidifies (lower pH) the narrow region near the bacterial plasma membrane. It has been shown in the gram positive bacterium *Bacillus subtilis*, that the activities of peptidoglycan autolysins are increased (i.e., no longer inhibited) when the electron transport system was blocked by adding proton conductors. This suggests that $\Delta\Psi$-plas-bact and $\Delta\mu H^+$ (independent of storing energy for cellular enzymatic functions) potentially has a profound and exploitable influence on cell wall anabolic functions and physiology.

In addition, it has been shown that $\Delta\Psi$-plas-bact uncouplers inhibit peptidoglycan formation with the accumulation of the nucleotide precursors involved in peptidoglycan synthesis, and the inhibition of transport of N-acetylglucosamine (GlcNAc), one of the major biopolymers in peptidoglycan.

Also, there is reference to an antimicrobial compound called tachyplesin that decreases $\Delta\Psi$-plas-bact in gram positive and gram negative pathogens. (Antimicrobial compositions and pharmaceutical preparations thereof. U.S. Pat. No. 5,610,139, the entire teaching of which is incorporated herein by reference.) This compound was shown at sub-lethal concentrations to have the ability to potentiate the cell wall synthesis inhibitor β-lactam antibiotic ampicillin in MRSA. It is desirable to couple the multiple influences of an optically lowered $\Delta\Psi$-plas-bact (i.e., increased cell wall autolysis, inhibited cell wall synthesis, and cell wall antimicrobial potentiation) to any other relevant antimicrobial therapy that targets bacterial cell walls. This is especially relevant in gram positive bacteria such as MRSA that do not have efflux pumps as resistance mechanisms for cell wall inhibitory antimicrobial compounds.

Cell wall inhibitory compounds do not need to gain entry through a membrane in gram positive bacteria, as is necessary with gram negative bacteria, to exhibit effects against the cell wall. Experimental evidence has proven that the NIMELS laser and its concomitant optical $\Delta\Psi$-plas-bact lowering phenomenon is synergistic with cell wall inhibitory antimicrobials in MRSA. This must function via the inhibition of anabolic (periplasmic) ATP coupled functions, as MRSA does not have efflux pumps that function on peptidoglycan inhibitory antimicrobials, as they do not need to enter the cell to be effective.

In one aspect, the invention provides a method of modifying the dipole potential $\Psi d$ of all membranes within the path of a NIMELS beam ($\Psi$d-plas-mam, $\Psi$d-mito-mam, $\Delta$d-plas-fungi, $\Psi$d-mito-fungi, and $\Psi$d-plas-bact) to set in motion the cascade of further alterations of $\Delta\Psi$ and $\Delta p$ in the same membranes.

The bioenergetic steady-state membrane potentials $\Delta\Psi$-steady of all irradiated cells ($\Delta\Psi$-steady-mam, $\Delta\Psi$-steady-fungi, $\Delta\Psi$-steady-Bact, $\Delta\Psi$-steady-mito-mam and $\Delta\Psi$-steady-mito-fungi) are altered to $\Delta\Psi$-trans values ($\Delta\Psi$-trans-mam, $\Delta\Psi$-trans-fungi, $\Delta\Psi$-trans-Bact, $\Delta\Psi$-trans-mito-mam and $\Delta\Psi$-trans-mito-fungi). This results in a concomitant depolarization and quantifiable alteration in the absolute value of the $\Delta p$ for all irradiated cells ($\Delta p$-mito-mam, $\Delta p$-mito-Fungi, $\Delta p$-plas-Fungi and $\Delta p$-plas-Bact).

These phenomena occur without intolerable risks and/or intolerable adverse effects to biological subjects (e.g., a mammalian tissue, cell or certain biochemical preparations such as a protein preparation) in/at the given target site other than the targeted biological contaminants (bacteria and fungi), by irradiating the target site with optical radiation of desired wavelength(s), power density level(s), and/or energy density level(s).

In certain embodiments, such applied optical radiation may have a wavelength from about 850 nm to about 900 nm, at a NIMELS dosimetry, as described herein. In exemplary embodiments, wavelengths from about 865 nm to about 875 nm are utilized. In further embodiments, such applied radiation may have a wavelength from about 905 nm to about 945 nm at a NIMELS dosimetry. In certain embodiments, such applied optical radiation may have a wavelength from about 925 nm to about 935 nm. In representative non-limiting embodiments exemplified hereinafter, the wavelength employed is 930 nm.

Bioenergetic steady-state membrane potentials may be modified, in exemplary embodiments, as noted below, and may employ multiple wavelength ranges including ranges bracketing 870 and 930 nm, respectively.

The NIMELS Potentiation Magnitude Scale (NPMS)

As discussed in more detail supra, NIMELS parameters include the average single or additive output power of the laser diodes and the wavelengths (870 nm and 930 nm) of the diodes. This information, combined with the area of the laser beam or beams (cm$^2$) at the target site, the power output of the laser system and the time of irradiation, provide the set of information which may be used to calculate effective and safe irradiation protocols according to the invention.

Based on these novel resistance reversal and antimicrobial potentiation interactions available with the NIMELS laser, there needs to be a quantitative value for the "potentiation effect" that will hold true for each unique antimicrobial and laser dosimetry.

A new set of parameters are defined that will take into account the implementation of any different dosimetric value for the NIMELS laser and any MIC value for a given antimicrobial being examined. This can be simply tailored to the NIMELS laser system and methods by creating only a set of variables that quantify CFU's of pathogenic organisms within any given experimental or treatment parameter with the NIMELS system.

These parameters create a scale called the NIMELS Potentiation Magnitude Scale (NPMS) and exploits the NIMELS lasers inherent phenomenon of reversing resistance and/or potentiating the MIC of antimicrobial drugs, while also producing a measure of safety against burning and injuring adjacent tissues, with power, and/or treatment time. The NPMS scale measures the NIMELS effect number (Ne) between 1 to 10, where the goal is to gain a Ne of ≥24 in reduction of CFU count of a pathogen, at any safe combination of antimicrobial concentration and NIMELS dosimetry. Although CFU count is used here for quantifying pathogenic organism, other means of quantification such as, for example, dye detection methods or polymerase chain reaction (PCR) methods can also be used to obtain values for A, B, and Np parameters.

The NIMELS effect number Ne is an interaction coefficient indicating to what extent the combined inhibitory/bacteriostatic effect of an antimicrobial drug is synergistic with the NIMELS laser against a pathogen target without significant harm to healthy tissue at the site of pathogen infection.

The NIMELS potentiation number (Np) is a value indicating whether the antimicrobial at a given concentration is synergistic, or antagonistic, to the pathogen target without harm to healthy tissue. Hence, within any given set of standard experimental or treatment parameters:
 A=CFU Count of pathogen with NIMELS alone;
 B=CFU Count of pathogen with antimicrobial alone;
 Np=CFU Count of pathogen with (NIMELS+Antimicrobial); and
 Ne=(A+B)/2Np;
Interpretation of NIMELS effect number Ne:
where:
If 2Np<A+B then the (given) antimicrobial has been successfully potentiated with the NIMELS laser at the employed concentrations and dosimetries.
then.
If Ne=1 then there is no potentiation effect. If Ne>1 then there is a potentiation effect. If Ne≥2 then there is at least a 50% potentiation effect on the antimicrobial. If Ne≥4 then there is at least a 75% potentiation effect on the antimicrobial. If Ne≥10 then there is at least a 90% potentiation effect on the antimicrobial.
Sample Calculation 1:
 A=110 CFU
 B=120 CFU
 Np=75 CFU
 Ne=(110 CFU+120 CFU)/2(75)=1.5
Sample Calculation 2:
 A=150 CFU
 B=90 CFU
 Np=30 CFU
 Ne=(150 CFU+90 CFU)/2(30)=4

In general, it can be advantageous to use a lower dose of antimicrobials when treating microbial infections, as the antimicrobials are expensive and by and large associated with undesirable side effects that can include systemic kidney and/or liver damage. Therefore, it is desirable to devise methods to lower and or potentiate the MIC of antimicrobials. The present invention provides systems and methods to reduce the MIC of antimicrobial molecules when the area being treated is concomitantly treated with the NIMELS laser system.

If the MIC of an antimicrobial is reduced for a localized and resistant local infection (e.g., skin, diabetic foot, bedsore), the therapeutic efficacy of many of the older, cheaper and safer antimicrobials to treat these infections will be restored. Therefore, decreasing the MIC of an antimicrobial, by the addition of the NIMELS laser (e.g., generating a value of Ne that is in one aspect>1 and in another aspect≥4 and yet in another aspect≥10), represents a positive step forward in restoring the once lost therapeutic efficacy of antibiotics.

Therefore, in one aspect, this invention provides methods and systems that will reduced the MIC of antimicrobial molecules necessary to eradicate or at least attenuate microbial pathogens via a depolarization of membranes within the irradiated field which will decrease the membrane potential $\Delta\Psi$ of the irradiated cells. This weakened $\Delta\Psi$ will cause an affiliated weakening of the proton motive force $\Delta p$, and the associated bioenergetics of all affected membranes. It is a further object of the present invention that this "NIMELS effect" potentiate existing antimicrobial molecules against microbes infecting and causing harm to human hosts.

In certain embodiments, such applied optical radiation has a wavelength from about 850 nm to about 900 nm, at a NIMELS dosimetry, as described herein. In exemplary embodiments, wavelengths from about 865 nm to about 875 nm are utilized. In further embodiments, such applied radiation has a wavelength from about 905 nm to about 945 nm at a NIMELS dosimetry. In certain embodiments, such applied optical radiation has a wavelength from about 925 nm to about 935 nm. In one aspect, the wavelength employed is 930 nm.

Microbial pathogens that have their bioenergetic systems affected by the NIMELS laser system according to the present invention include microorganisms such as, for example, bacteria, fungi, molds, mycoplasmas, protozoa, and parasites. Exemplary embodiments, as noted below may employ multiple wavelength ranges including ranges bracketing 870 and 930 nm, respectively.

In the methods according to one aspect of the invention, irradiation by the wavelength ranges contemplated are performed independently, in sequence, in a blended ratio, or essentially concurrently (all of which can utilize pulsed and/or continuous-wave, CW, operation).

Irradiation with NIMELS energy at NIMELS dosimetry to the biological contaminant is applied prior to, subsequent to, or concomitant with the administration of an antimicrobial agent. However, said NIMELS energy at NIMELS dosimetry can be administered after antimicrobial agent has reached a "peak plasma level" in the infected individual or other mammal. It should be noted that the co-administered antimicrobial agent ought to have antimicrobial activity against any naturally sensitive variants of the resistant target contaminant.

The wavelengths irradiated according to the present methods and systems increase the sensitivity of a contaminant to the level of a similar non-resistant contaminant strain at a concentration of the antimicrobial agent of about 0.5 M or less, about 0.1 M or less, or about 0.01 M or less, about 0.005 M or less or about 0.005 M or less.

The methods of the invention slow or eliminate the progression of microbial contaminants in a target site, improve at least some symptoms or asymptomatic pathologic conditions associated with the contaminants, and/or increase the sensitivity of the contaminants to an antimicrobial agent. For example, the methods of the invention result in a reduction in the levels of microbial contaminants in a target site and/or potentiate the activity of antimicrobial compounds by increasing the sensitivity of a biological contaminant to an antimicrobial agent to which the biological contaminant has evolved or acquired resistance, without an adverse effect on a biological subject. The reduction in the levels of microbial contaminants can be, for example, at least 10%, 20%, 30%, 50%, 70%, 100% or more as compared to pretreatment levels. It is preferred that the bacterial reduction be approximately a 2 or 3 log reduction. With regard to sensitivity of a biological contaminant to an antimicrobial agent, the sensitivity is potentiated by at least 10% and preferably by several orders of magnitude.

In another aspect, the invention provides a system to implement the methods according to other aspects of the invention. Such a system includes a laser oscillator for generating the radiation, a controller for calculating and controlling the dosage of the radiation, and a delivery assembly (system) for transmitting the radiation to the treatment site through an application region. Suitable delivery assemblies/systems include hollow waveguides, fiber optics, and/or free space/beam optical transmission components. Suitable free space/beam optical transmission components include collimating lenses and/or aperture stops.

In one form, the system utilizes two or more solid state diode lasers to function as a dual wavelength near-infrared optical source. The two or more diode lasers may be located in a single housing with a unified control. The two wavelengths can include emission in two ranges from about 850 nm to about 900 nm and from about 905 nm to about 945 nm. The laser oscillator of the present invention is used to emit a single wavelength (or a peak value, e.g., central wavelength) in one of the ranges disclosed herein. In certain embodiments, such a laser is used to emit radiation substantially within the about 865-875 nm and the about 925-935 nm ranges.

Systems according to the present invention can include a suitable optical source for each individual wavelength range desired to be produced. For example, a suitable solid stated laser diode, a variable ultra-short pulse laser oscillator, or an ion-doped (e.g., with a suitable rare earth element) optical fiber or fiber laser is used. In one form, a suitable near infrared laser includes titanium-doped sapphire. Other suitable laser sources including those with other types of solid state, liquid, or gas gain (active) media may be used within the scope of the present invention.

According to one embodiment of the present invention, a therapeutic system includes an optical radiation generation system adapted to generate optical radiation substantially in a first wavelength range from about 850 nm to about 900 nm, a delivery assembly for causing the optical radiation to be transmitted through an application region, and a controller operatively connected to the optical radiation generation device for controlling the dosage of the radiation transmitted through the application region, such that the time integral of the power density and energy density of the transmitted radiation per unit area is below a predetermined threshold. Also within this embodiment, are therapeutic systems especially adapted to generate optical radiation substantially in a first wavelength range from about 865 nm to about 875 nm.

According to further embodiments, a therapeutic system includes an optical radiation generation device that is configured to generate optical radiation substantially in a second wavelength range from about 905 nm to about 945 nm; in certain embodiments the noted first wavelength range is simultaneously or concurrently/sequentially produced by the optical radiation generation device. Also within the scope of this embodiment, are therapeutic systems especially adapted to generate optical radiation substantially in a first wavelength range from about 925 nm to about 935 nm.

The therapeutic system can further include a delivery assembly (system) for transmitting the optical radiation in the second wavelength range (and where applicable, the first wavelength range) through an application region, and a controller operatively for controlling the optical radiation generation device to selectively generate radiation substantially in the first wavelength range or substantially in the second wavelength range or any combinations thereof.

According to one embodiment, the delivery assembly comprises one or more optical fibers having an end configured and arranged for insertion in patient tissue at a location within an optical transmission range of the medical device, wherein the radiation is delivered at a NIMELS dosimetry to the tissue surrounding the medical device. The delivery assembly may further comprise a free beam optical system.

According to a further embodiment, the controller of the therapeutic system includes a power limiter to control the dosage of the radiation. The controller may further include memory for storing a patient's profile and dosimetry calculator for calculating the dosage needed for a particular target site based on the information input by an operator. In one aspect, the memory may also be used to store information about different types of diseases and the treatment profile, for example, the pattern of the radiation and the dosage of the radiation, associated with a particular application.

The optical radiation can be delivered from the therapeutic system to the application site in different patterns. The radiation can be produced and delivered as a continuous wave (CW), or pulsed, or a combination of each. For example, in a single wavelength pattern or in a multi-wavelength (e.g., dual-wavelength) pattern. For example, two wavelengths of radiation can be multiplexed (optically combined) or transmitted simultaneously to the same treatment site. Suitable optical combination techniques can be used, including, but not limited to, the use of polarizing beam splitters (combiners), and/or overlapping of focused outputs from suitable mirrors and/or lenses, or other suitable multiplexing/combining techniques. Alternatively, the radiation can be delivered in an alternating pattern, in which the radiation in two wavelengths are alternatively delivered to the same treatment site. An interval between two or more pulses may be selected as desired according to NIMELS techniques of the present invention. Each treatment may combine any of these modes of transmission. The intensity distributions of the delivered optical radiation can be selected as desired. Exemplary embodiments include top-hat or substantially top-hat (e.g., trapezoidal, etc.) intensity distributions. Other intensity distributions, such as Gaussian may be used.

One of skill in the art will appreciate that the methods and systems of the invention may be used in conjunction with a variety of biological contaminants generally known to those skilled in the art. The following lists are provided solely for the purpose of illustrating the broad scope of microorganisms which may be targeted according to the methods and devices of the present invention and are not intended to limit the scope of the invention.

Accordingly, illustrative non-limiting examples of biological contaminants (pathogens) include, but are not limited to, any bacteria, such as, for example, *Escherichia, Enterobacter, Bacillus, Campylobacter, Corynebacterium, Klebsiella, Listeria, Mycobacterium, Neiseria, Pseudomonas, Salmonella, Streptococcus, Staphylococcus, Treponema, Vibrio* and *Yersinia*.

It will be understood that the target site to be irradiated need not be already infected with a biological contaminant. Indeed, the methods of the present invention may be used "prophylactically," prior to infection. Further embodiments include use on medical devices such as catheters, (e.g., IV catheter, central venous line, arterial catheter, peripheral catheter, dialysis catheter, peritoneal dialysis catheter, epidural catheter), artificial joints, stents, external fixator pins, chest tubes, gastronomy feeding tubes, etc.

In certain instances, irradiation may be palliative as well as prophylactic. Hence, the methods of the invention are used to irradiate a tissue or tissues for a therapeutically effective amount of time for treating or alleviating the symptoms of an infection. The expression "treating or alleviating" means reducing, preventing, and/or reversing the symptoms of the individual treated according to the invention, as compared to the symptoms of an individual receiving no such treatment.

One of skill in the art will appreciate that the invention is useful in conjunction with a variety of diseases caused by or otherwise associated with any microbial, fungal, and viral infection (see, Harrison's, *Principles of Internal Medicine*, 13$^{th}$ Ed., McGraw Hill, N.Y. (1994), the entire teaching of which is incorporated herein by reference). In certain embodiments, the methods and the systems according to the invention are used in concomitance with traditional therapeutic approaches available in the art (see, e.g., Goodman and Gilman's, The Pharmacological Basis of Therapeutics, 8th ed, 1990, Pergmon Press, the entire teaching of which is incorporated herein by reference.) to treat an infection by the administration of known antimicrobial agent compositions. The terms "antimicrobial composition", "antimicrobial agent" refer to compounds and combinations thereof that are administered to an animal, including human, and which inhibit the proliferation of a microbial infection (e.g., antibacterial, antifungal, and antiviral).

The wide breath of applications contemplated include, for example, a variety of dermatological, podiatric, pediatric, and general medicine to mention but a few. The interaction between a target site being treated and the energy imparted is defined by a number of parameters including: the wavelength(s); the chemical and physical properties of the target site; the power density or irradiance of beam; whether a continuous wave (CW) or pulsed irradiation is being used; the laser beam spot size; the exposure time, energy density, and any change in the physical properties of the target site as a result of laser irradiation with any of these parameters. In addition, the physical properties (e.g., absorption and scattering coefficients, scattering anisotropy, thermal conductivity, heat capacity, and mechanical strength) of the target site may also affect the overall effects and outcomes.

The NIMELS dosimetry denotes the power density ($W/cm^2$) and the energy density ($J/cm^2$; where 1 Watt=1 Joule/second) values at which a subject wavelength is capable of generating ROS and thereby reducing the level of a biological contaminant in a target site, and/or irradiating the contaminant to increase the sensitivity of the biological contaminant through the lowering of $\Delta\Psi$ with concomitant generation of ROS to an antimicrobial agent that said contaminant is resistant to without intolerable risks and/or intolerable side effects on a biological moiety (e.g., a mammalian cell, tissue, or organ) other than the biological contaminant.

As discussed in Boulnois 1986, (Lasers Med. Sci. 1:47-66 (1986), the entire teaching of which is incorporated herein by reference), at low power densities (also referred to as irradiances) and/or energies, the laser-tissue interactions can be described as purely optical (photochemical), whereas at higher power densities photo-thermal interactions ensue. In certain embodiments, exemplified hereinafter, NIMELS dosimetry parameters lie between known photochemical and photo-thermal parameters in an area traditionally used for photodynamic therapy in conjunction with exogenous drugs, dyes, and/or chromophores, yet can function in the realm of photodynamic therapy without the need of exogenous drugs, dyes, and/or chromophores.

The energy density—also expressible as fluence, or the product (or integral) of particle or radiation flux and time—for medical laser applications in the art typically varies between about 1 $J/cm^2$ to about 10,000 $J/cm^2$ (five orders of magnitude), whereas the power density (irradiance) varies from about $1 \times 10^3$ $W/cm^2$ to over about $10^{12}$ $W/cm^2$ (15 orders of magnitude). Upon taking the reciprocal correlation between the power density and the irradiation exposure time, it can be observed that approximately the same energy density is required for any intended specific laser-tissue interaction. As a result, laser exposure duration (irradiation time) is the primary parameter that determines the nature and safety of laser-tissue interactions. For example, if one were mathematically looking for thermal vaporization of tissue in vivo (non-ablative) (based on Boulnois 1986), it can be seen that to produce an energy density of 1000 $J/cm^2$ (see, Table 1) one could use any of the following dosimetry parameters:

TABLE 1

Example of Values Derived on the Basis of the Boulnois Table

| POWER DENSITY | TIME | ENERGY DENSITY |
| --- | --- | --- |
| $1 \times 10^5$ $W/cm^2$ | 0.01 sec. | 1000 $J/cm^2$ |
| $1 \times 10^4$ $W/cm^2$ | 0.10 sec. | 1000 $J/cm^2$ |
| $1 \times 10^3$ $W/cm^2$ | 1.00 sec. | 1000 $J/cm^2$ |

This progression describes a suitable method or basic algorithm that can be used for a NIMELS interaction against a biological contaminant in a tissue. In other words, this mathematical relation is a reciprocal correlation to achieve a laser-tissue interaction phenomena. This rationale can be used as a basis for dosimetry calculations for the observed antimicrobial phenomenon imparted by NIMELS energies with insertion of NIMELS experimental data in the energy density and time and power parameters.

On the basis of the particular interactions at the target site being irradiated (such as the chemical and physical properties of the target site; whether continuous wave (CW) or pulsed irradiation is being used; the laser beam spot size; and any change in the physical properties of the target site, e.g., absorption and scattering coefficients, scattering anisotropy, thermal conductivity, heat capacity, and mechanical strength, as a result of laser irradiation with any of these parameters), a practitioner is able to adjust the power density and time to obtain the desired energy density.

The examples provided herein show such relationships in the context of both in vitro and in vivo treatments. Hence, in the context of treating subjects, for spot sizes having a diameter of 1-4 cm, power density values were varied from about 0.2 $W/cm^2$ to about 5 $W/cm^2$ and preferably 0.3 $W/cm^2$ to about 0.7 $W/cm^2$ to stay within safe and non-damaging/minimally damaging thermal laser-tissue interactions well below the level of "denaturization" and "tissue overheating". Other suitable spot sizes may be used. With this reciprocal correlation, the threshold energy density needed for a NIMELS interaction with these wavelengths can be maintained independent of the spot-size so long as the desired energies are delivered. In exemplary embodiments, the optical energy is delivered through a uniform geometric distribution to the tissues (e.g., a flat-top, or top-hat progression). With such a technique, a suitable NIMELS dosimetry sufficient to generate ROS (a NIMELS effect) can be calculated to reach the threshold energy densities required to reduce the level of a biological contaminant and/or to increase the sensitivity of the biological contaminant to an antimicrobial agent that said contaminant is resistant to, but below the level of "denaturization" and "tissue overheating".

NIMELS dosimetries exemplified herein to target microbes in vivo, were from about 125 $J/cm^2$ to about 700 $J/cm^2$ and preferably 150 $J/cm^2$ to about 400 $J/cm^2$ for approximately 100 to 700 seconds. These power values do not approach power values associated with photoablative or photothermal (laser/tissue) interactions.

The intensity distribution of a collimated laser beam is given by the power density of the beam, and is defined as the ratio of laser output power to the area of the circle in ($cm^2$) and the spatial distribution pattern of the energy. Hence, the illumination pattern of a 1.5 cm irradiation spot with an incident Gaussian beam pattern of the area 1.77 $cm^2$ can produce at least six different power density values within the 1.77 $cm^2$ irradiation area. These varying power densities increase in intensity (or concentration of power) over the surface area of the spot from 1 (on the outer periphery) to 6 at the center point. In certain embodiments of the invention, a beam pattern is provided which overcomes this inherent error associated with traditional laser beam emissions. NIMELS parameters may be calculated as a function of treatment time (Tn) as follows: Tn=Energy Density/Power Density.

In certain embodiments (see, e.g., the in vitro experiments hereinbelow), Tn is from about 50 to about 300 seconds; in other embodiments, Tn is from about 75 to about 200 seconds; in yet other embodiments, Tn is from about 100 to about 150 seconds. In in vivo embodiments, Tn is from about 100 to about 1200 seconds.

Utilizing the above relationships and desired optical intensity distributions, e.g., flat-top illumination geometries as described herein, a series of in vivo energy parameters have been experimentally proven as effective for NIMELS microbial decontamination therapy in vitro. A key parameter for a given target site has thus been shown to be the energy density required for NIMELS therapy at a variety of different spot sizes and power densities.

"NIMELS dosimetry" encompasses ranges of power density and/or energy density from a first threshold point at which a subject wavelength according to the invention is capable of optically reducing $\Delta\Psi$ in a target site to a second end-point and/or to increase the sensitivity of the biological contaminant to an antimicrobial agent that said contaminant is resistant to via generation of ROS, immediately before those values at which an intolerable adverse risk or effect is detected (e.g., thermal damage such as poration) on a biological moiety. One of skill in the art will appreciate that under certain circumstances adverse effects and/or risks at a target site (e.g., a mammalian cell, tissues, or organ) may be tolerated in view of the inherent benefits accruing from the methods of the invention. Accordingly, the stopping point contemplated are those at which the adverse effects are considerable and, thus, undesired (e.g., cell death, protein denaturation, DNA damage, morbidity, or mortality).

In certain embodiments, e.g., for in vivo applications, the power density range contemplated herein is from about 0.25 to about 40 W/cm². In other embodiments, the power density range is from about 0.5 W/cm² to about 25 W/cm². Currently preferred embodiments for decolonizing a microbial site on a subject utilize a power density range from about 0.3 W/cm² to about 0.7 W/cm² when antibacterial compounds are coadministered. Currently preferred embodiments for decolonizing a microbial site on a subject utilize an energy density range from about 125 J/cm² to about 400 J/cm² when antibacterial compounds are coadministered.

In further embodiments, power density ranges can encompass values from about 0.5 W/cm² to about 10 W/cm². Power densities exemplified herein are from about 0.5 W/cm² to about 5 W/cm². Power densities in vivo from about 1.5 to about 2.5 W/cm² have been shown to be effective for various microbes with or without coadministration of antibiotics.

Empirical data appears to indicate that higher power density values are generally used when targeting a biological contaminant in an in vitro setting (e.g., plates) rather than in vivo (e.g., toe nail).

In certain embodiments (see, in vitro examples below), the energy density range contemplated herein is greater than 50 J/cm² but less than about 25,000 J/cm². In other embodiments, the energy density range is from about 750 J/cm² to about 7,000 J/cm². In yet other embodiments, the energy density range is from about 1,500 J/cm² to about 6,000 J/cm² depending on whether the biological contaminant is to be targeted in an in vitro setting (e.g., plates) or in vivo (e.g., toe nail or surrounding a medical device). In certain embodiments (see, in vivo examples below), the energy density is from about 100 J/cm² to about 500 J/cm². In yet other in vivo embodiments, the energy density is from about 175 J/cm² to about 300 J/cm². In yet other embodiments, the energy density is from about 200 J/cm² to about 250 J/cm². In some embodiments, the energy density is from about 300 J/cm² to about 700 J/cm². In some other embodiments, the energy density is from about 300 J/cm² to about 500 J/cm². In yet others, the energy density is from about 300 J/cm² to about 450 J/cm².

Power densities empirically tested for various in vitro treatment of microbial species were from about 1 W/cm² to about 10 W/cm².

One of skill in the art will appreciate that the identification of particularly suitable NIMELS dosimetry values within the power density and energy density ranges contemplated herein for a given circumstance may be empirically done via routine experimentation. Practitioners (e.g., dentists) using near infrared energies in conjunction with periodontal treatment routinely adjust power density and energy density based on the exigencies associated with each given patient (e.g., adjust the parameters as a function of tissue color, tissue architecture, and depth of pathogen invasion). As an example, laser treatment of a periodontal infection in a light-colored tissue (e.g., a melanine deficient patient) will have greater thermal safety parameters than darker tissue, because the darker tissue will absorb near-infrared energy more efficiently, and hence transform these near-infrared energies to heat in the tissues faster. Hence, the obvious need for the ability of a practitioner to identify multiple different NIMELS dosimetry values for different therapy protocols.

As illustrated infra, it has been found that antibiotic resistant bacteria may be effectively treated according to the methods of the present invention. In addition, it has been found that the methods of this invention may be used to augment traditional approaches, to be used in combination with, in lieu of tradition therapy, or even serially as an effective therapeutic approach. Accordingly, the invention may be combined with antibiotic treatment. The term "antibiotic" includes, but is not limited to β-lactams, penicillins, and cephalosporins, vancomycins, bacitracins, macrolides (erythromycins), ketolides (telithromycin), lincosamides (clindamycin), chloramphenicols, tetracyclines, aminoglycosides (gentamicins), amphotericns, anilinouracils, cefazolins, clindamycins, mupirocins, sulfonamides and trimethoprim, rifampicins, metronidazoles, quinolones, novobiocins, polymixins, oxazolidinone class (e.g., linezolid), glycylcyclines (e.g., tigecycline), cyclic lipopeptides (e.g., daptomycin), pleuromutilins (e.g., retapamulin) and gramicidins and the like and any salts or variants thereof. It also understood that it is within the scope of the present invention that the tetracyclines include, but are not limited to, immunocycline, chlortetracycline, oxytetracycline, demeclocycline, methacycline, doxycycline and minocycline and the like. It is also further understood that it is within the scope of the present invention that aminoglycoside antibiotics include, but are not limited to, gentamicin, amikacin and neomycin, and the like.

A common tenet in the search for inhibitors of drug resistance systems in bacteria, or a potentiator of antimicrobial agents has always been that such agents are preferably non-toxic to the mammalian tissues that are infected, in order to have any intrinsic value. To accomplish this, most antimicrobials affect bacterial cellular processes that are not common to the mammalian host, and, hence, are less disruptive to host metabolic processes. If antimicrobials, potentiators, and/or resistance reversal entities were to also affect the mammalian cells in the same manner as they damage the pathogens, over similar concentrations, they could not be used safely as therapeutic agents.

In the current invention, the experimental data provided herein supports a universal alteration of $\Delta\Psi$ and $\Delta p$ among all cell types, and hence leads to the notion that not only the electro-mechanical, but also the electro-dynamical aspects of all cell membranes, have no differing properties that can adequately be separated. This indicates that all cells in the path of the beam are affected with depolarization, not only the pathogenic (non-desired) cells.

By reaffirming what the photobiology and cellular energetics data of the NIMELS system has already illuminated (i.e., that all of membrane energetics are affected in the same way across prokaryotic and eukaryotic species), techniques according to the present invention utilize this universal optical depolarizing effect to be independently exploited in non-desired cells, by adding antimicrobial agents to a therapeutic regimen, and potentiating such molecules in (only) non-desired cells. Such a targeted therapeutic outcome can exploit the NIMELS laser's effect of universal depolarization, with the targeted toxicity of microbial antibiotics, the combination being somewhat transient to the metabolism of the host cells but highly disruptive and preferably lethal to the bacteria.

The examples below provide experimental evidence proving the concept of universal optical membrane depolarization coupled to our current understanding of photobiology and cellular energetics and the conservation of thermodynamics as applied to cellular processes.

EXAMPLES

The following examples are included to demonstrate exemplary embodiments of the present invention and are not intended to limit the scope of the invention. Those of skill in the art, will appreciate that many changes can be made in the specific embodiments and still obtain a like or similar result without departing from the spirit and scope of the present invention.

Example I

TABLE 2

MIC values for Susceptible, Intermediate and Resistant *S. aureus* Minimum Inhibitory Concentration (MIC) Interpretive Standards (μg/ml) for *Staphylococcus* sp.

| Antimicrobial Agent | Susceptible | Intermediate | Resistant |
|---|---|---|---|
| Penicillin | ≤0.12 | — | ≥0.25 |
| Methicillin | ≤8 | — | ≥16 |
| Aminoglycosides | | | |
| Gentamicin | ≤4 | 8 | ≥16 |
| Kanamycin | ≤16 | 32 | ≥64 |
| Macrolides | | | |
| Erythromycin | ≤0.5 | 1-4 | ≥8 |
| Tetracycline | | | |
| Tetracycline | ≤4 | 8 | ≥16 |
| Fluoroquinolone | | | |
| Ciprofloxacin | ≤1 | 2 | ≥4 |

TABLE 2-continued

MIC values for Susceptible, Intermediate and Resistant *S. aureus* Minimum Inhibitory Concentration (MIC) Interpretive Standards (μg/ml) for *Staphylococcus* sp.

| Antimicrobial Agent | Susceptible | Intermediate | Resistant |
|---|---|---|---|
| Folate Pathway Inhibitors | | | |
| Trimethoprim | ≤8 | — | ≥16 |
| Ansamycins | | | |
| Rifampin | ≤1 | 2 | ≥4 |

Example II

Bacterial Methods: NIMELS Treatment Parameters for In Vitro MRSA Experiments

The following illustrates the general antibacterial methods according to the invention, using a MRSA model for the in vitro Experiments V and VIII-XII.

A. Experiment Materials and Methods for MRSA:

TABLE 3

Method: for CFU counts

| Time (hrs) | Task | FTE (hrs) |
|---|---|---|
| T −18 | Inoculate overnight culture 50 ml directly from glycerol stock | 1 |
| T −4 | Set up starter cultures Three dilutions 1:50, 1:125, 1:250 LB Media Monitor $OD_{600}$ of starter cultures | 1 4 |
| T 0 | Preparation of plating culture At 10:00 am, the culture which is at $OD_{600}$ = 1.0 is diluted 1:300 in PBS (50 mls final volume) and stored at RT for 1 hour. (Room temp should be ~25° C.) | 1 |
| T +1 | Seeding of 24-well plates 2 ml aliquots are dispensed into pre-designated wells in 24-well plates. | 1 |
| T +2 to +8 | Dilution of treated samples After laser treatment, 100 μl from each well is diluted serially to a final dilution of 1:1000 in PBS. Plating of treated samples 100 μl of final dilution is plated in quintuplicate (5X) on TSB agar with and without antibiotics. (10 TSB plates per well) Plates are incubated at 37° C. 18-24 hrs. | 4 2 |
| T +24 | Colonies are counted on each plate | 6 |

Similar cell culture and kinetic protocols were performed with *E. coli* for all NIMELS irradiation experiments. A standardized suspension was aliquoted into selected wells in a 24-well tissue culture plate. Following laser treatments, 100 μL was removed from each well and serially diluted to 1:1000 resulting in a final dilution of $1:5\times10^6$ of initial culture. An aliquot of each final dilution were spread onto separate plates. The plates were then incubated at 37° C. for approximately 16-20 hours. Manual colony counts were performed and recorded.

TABLE 4

Method: for ΔΨ and ROS Assays

| Time (hrs) | Task | FTE (hrs) |
|---|---|---|
| T −18 | Inoculate overnight culture 50 ml directly from glycerol stock | 1 |
| T −4 | Set up starter cultures Three dilutions 1:50, 1:125, 1:250 LB Media | 1 |
|  | Monitor $OD_{600}$ of starter cultures | 4 |
| T 0 | Preparation of plating culture At 10:00 am, the culture which is at $OD_{600}$ = 1.0 is diluted 1:300 in PBS (50 mls final volume) and stored at RT for 1 hour. (Room temp should be ~25° C.) | 1 |
| T +1 | Seeding of 24-well plates for Assays 2 ml aliquots are dispensed into pre-designated wells in 24-well plates. | 1 |
| T +2 to +8 | Dilution of treated samples After laser treatment each control and lased sample were treated as per directions of individual assay. | 4 |

Again, similar cell culture and kinetic protocols were performed for all NIMELS irradiation with *E. coli*. A standardized suspension was aliquoted into selected wells in a 24-well tissue culture plate. Following laser treatments each lased and control sample were treated as per directions of individual assay.

Example III

Mammalian Cell Methods: NIMELS Treatment Parameters for In Vitro HEK293 Experiments The following parameters illustrate the general methods according to the invention as applied to HEK293 cells for the in vitro experiments.

A. Experiment Materials and Methods for HEK293 Cells.

HEK293 cells were seeded into appropriate wells of a 24-well plate at a density of $1 \times 10^5$ cells/ml (0.7 ml total volume) in Freestyle medium (Invitrogen). Cells were incubated in a humidified incubator at 37° C. in 8% $CO_2$ for approximately 48 hours prior to the experiment. Cells were approximately 90% confluent at the time of the experiment equating to roughly $3 \times 10^5$ total cells. Immediately prior to treatment, cells were washed in pre-warmed phosphate buffer saline (PBS) and overlaid with 2 ml of PBS during treatment. After laser treatment, cells were mechanically dislodged from the wells and transferred to 1.5 ml centrifuge tubes. Mitochondrial membrane potential and total glutathione was determined.

Example IV

NIMELS In Vitro Tests for CRT+ (Yellow) and CRT− (White) *S. Aureus* Experiments We conducted experiments with crt− (white) mutants of *S. aureus* that were genetically engineered with the crt gene (yellow carotenoid pigment) removed, and these mutants were subjected to previously determined non-lethal doses of NIMELS laser against wild type (yellow) *S. aureus*. The purpose of this experiment was to test for the phenomenon of Radical Oxygen Species (ROS) generation and/or singlet oxygen generation with the NIMELS laser. In the scientific literature, Liu et al. had previously used a similar model, to test the antioxidant protection activity of the yellow *S. aureus*\*caratenoid) pigment against neutrophils. (Liu et al., *Staphylococcus aureus* golden pigment impairs neutrophil killing and promotes virulence through its antioxidant activity, Vol. 202, No. 2, Jul. 18, 2005 209-215, the entire teaching of which is incorporated herein by reference.)

It has previously been determined that the golden color in *S. aureus* is imparted by carotenoid (antioxidant) pigments capable of protecting the organism from oxygen damage, and when a mutant is isolated (crt) that does not produce such carotenoid pigments, the mutant colonies are "white" in appearance and more susceptible to oxidative killing, and have impaired neutrophil survival.

It was found that non-lethal dosimetries of the NIMELS laser (to wild type *S. aureus*) consistently killed up to 90% of the mutant "white" cells and did not kill the normal *S. aureus*. The only genetic difference in the two strains of *S. aureus* is the lack of an antioxidant pigment in the mutant. This experimental data strongly suggests that it is the endogenous generation of radical oxygen species and/or singlet oxygen that are killing the "white" *S. aureus*.

TABLE 5

Data: D1-D4 Yellow Wild Type *S. aureus*. D5-D6 White "crt−" Mutant *S. Aureus*.

| Plate No | Output Power (W) | Beam Spot (cm) | Time (sec) | Total Energy Joules | Energy Density ($J/cm^2$) | Power Density ($W/cm^2$) |
|---|---|---|---|---|---|---|
| D1 | 11 | 1.5 | 720 | 7920 | 4481.793 | 6.224712 |
| D2 | 11.5 | 1.5 | 720 | 8280 | 4685.511 | 6.507654 |
| D3 | 12 | 1.5 | 720 | 8640 | 4889.228 | 6.790595 |
| D4 | 12.5 | 1.5 | 720 | 9000 | 5092.946 | 7.073536 |
| D5 | 11 | 1.5 | 720 | 7920 | 4481.793 | 6.224712 |
| D6 | 11.5 | 1.5 | 720 | 8280 | 4685.511 | 6.507654 |
| D7 | 12 | 1.5 | 720 | 8640 | 4889.228 | 6.790595 |
| D8 | 12.5 | 1.5 | 720 | 9000 | 5092.946 | 7.073536 |

TABLE 6

Samples D1-D4 Yellow Wild Type *S. aureus*. Samples D5-D6 White "crt-" Mutant *S. aureus*. *S. aureus* study (ATCC 12600 WT & CRTM-)

| Sample | Control CFU's | Laser-treated CFU' | Percent of Control |
|---|---|---|---|
| D1 | 203 | 44 | 18.48 |
|  | 274 | 55 |  |
|  | 291 | 35 |  |
|  | 241 | 46 |  |
|  | 268 | 56 |  |
| D2 | 270 | 155 | 46.76 |
|  | 303 | 133 |  |
|  | 266 | 110 |  |
|  | 245 | 111 |  |
|  | 321 | 148 |  |
| D3 | 315 | 87 | 25.32 |
|  | 344 | 101 |  |
|  | 310 | 100 |  |
|  | 350 | 71 |  |
|  | 395 | 75 |  |
| D4 | 405 | 23 | 7.21 |
|  | 472 | 31 |  |
|  | 401 | 30 |  |
|  | 403 | 32 |  |
|  | 359 | 31 |  |
| D5 | 530 | 163 | 35.05 |
|  | 534 | 194 |  |
|  | 520 | 192 |  |
|  | 552 | 194 |  |
|  | 520 | 188 |  |
| D6 | 252 | 54 | 20.00 |
|  | 262 | 46 |  |

TABLE 6-continued

Samples D1-D4 Yellow Wild Type *S. aureus*.
Samples D5-D6 White "crt-" Mutant *S. aureus*.
*S. aureus* study (ATCC 12600 WT & CRTM-)

| Sample | Control CFU's | Laser-treated CFU' | Percent of Control |
|---|---|---|---|
|    | 248 | 50 |        |
|    | 273 | 70 |        |
|    | 270 | 41 |        |
| D7 | 276 | 40 | 14.68  |
|    | 169 | 30 |        |
|    | 260 | 38 |        |
|    | 259 | 35 |        |
|    | 296 | 42 |        |
| D8 | 323 | 6  | 1.68   |
|    | 348 | 3  |        |
|    | 423 | 9  |        |
|    | 408 | 6  |        |
|    | 340 | 7  |        |

Example V

NIMELS In Vitro Tests for ΔΨ Alteration in MRSA, and *E. Coli*

There are selected fluorescent dyes that can be taken up by intact cells and accumulate within the intact cells within 15 to 30 minutes without appreciable staining of other protoplasmic constituents. These dye indicators of membrane potential have been available for many years and have been employed to study cell physiology. The fluorescence intensity of these dyes can be easily monitored, as their spectral fluorescent properties are responsive to changes in the value of the transmembrane potentials ΔΨ-steady.

These dyes generally operate by a potential-dependent partitioning between the extracellular medium and either the membrane or the cytoplasm of membranes. This occurs by redistribution of the dye via interaction of the voltage potential with an ionic charge on the dye. This fluorescence can be eliminated in about 5 minutes by the protonophore carbonyl cyanide m-chlorophenylhydrazone (CCCP), indicating that maintenance of dye concentration is dependent on the inside-negative transmembrane potential maintained by functional ETS and Δp.

Hypothesis Testing:
The null hypothesis is $\mu_1-\mu_2=0$:
$\mu_1$ is fluorescence intensity in a control cell culture (no laser) subjected to carbocyanine dye
$\mu_2$ is fluorescence intensity in the same cell culture pre-irradiated with sub-lethal dosimetry from the NIMELS laser The data indicates that the fluorescence of cells is dissipated (less than control of unirradiated or "unlased" cells) by pre-treatment (of the cells) with the NIMELS laser system, indicating that the NIMELS laser interacted with respiratory processes and oxidative phosphorylation of the cells via the plasma membranes.

$$\mu_1-\mu_2=0$$

Will uphold that the addition sub-lethal NIMEL irradiation on the cell culture has no effect on ΔΨ-steady.

$$\mu_1-\mu_2>0$$

Will uphold that the addition sub-lethal NIMEL irradiation on the cell culture has a dissipation or depolarization effect on ΔΨ-steady.

Materials and Methods:
BacLight™ Bacterial Membrane Potential Kit (B34950, Invitrogen U.S.). The BacLight™ Bacterial Membrane Potential Kit provides of carbocyanine dye DiOC2(3) (3,3'-diethyloxacarbocyanine iodide, Component A) and CCCP (carbonyl cyanide 3-chlorophenylhydrazone, Component B), both in DMSO, and a 1×PBS solution (Component C).

DiOC2(3) exhibits green fluorescence in all bacterial cells, but the fluorescence shifts toward red emission as the dye molecules self associate at the higher cytosolic concentrations caused by larger membrane potentials. Proton ionophores such as CCCP destroy membrane potential by eliminating the proton gradient, hence causing higher green fluorescence.

Detection of Membrane Potential ΔΨ in MRSA
Green fluorescence emission was calculated using population mean fluorescence intensities for control and lased samples at sub-lethal dosimetry:

TABLE 7

MRSA Dosimetry Progression
First lasing procedure: Both 870 and 930
Second lasing procedure 930 alone

| Parameters | Output Power (W) | Beam Spot (cm) | Area of Spot (cm2) | Time (sec) |
|---|---|---|---|---|
| 870 at 4.25 W and 930 at 4.25 W for 16 min followed by | 8.5 | 1.5 | 1.77 | 960 |
| 930 at 8.5 W for 7 min | 8.5 | 1.5 | 1.77 | 420 |

Figure 8A:
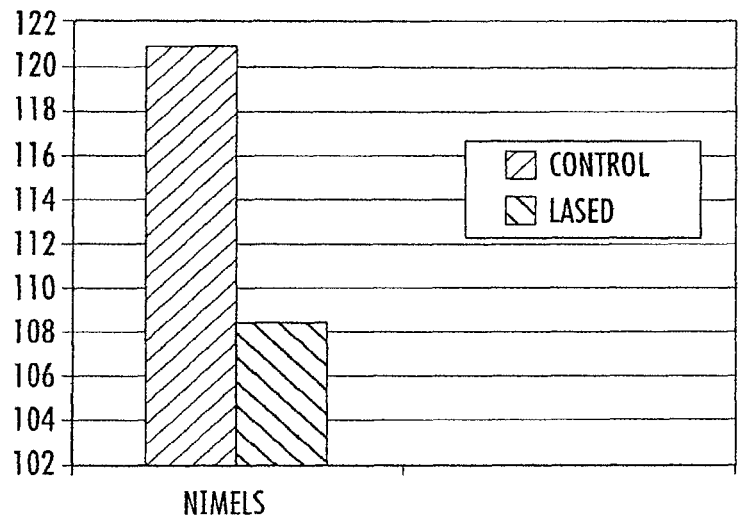
FIG. 8 shows the effects of NIMELS irradiation (at a single dosimetry) on mitochondrial membrane potential of human embryonic kidney cells, which is measured by red fluorescence emission intensities in control and lased samples; and the effects of NIMELS irradiation (at a single dosimetry) on mitochondrial membrane potential of human embryonic kidney cells, which is measured as ratio of red to green fluorescence in control and lased samples.
Figure 8B:
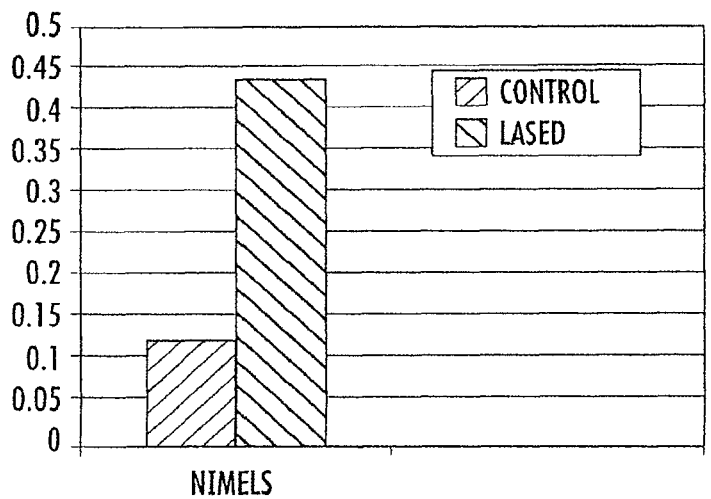
Figure 9:
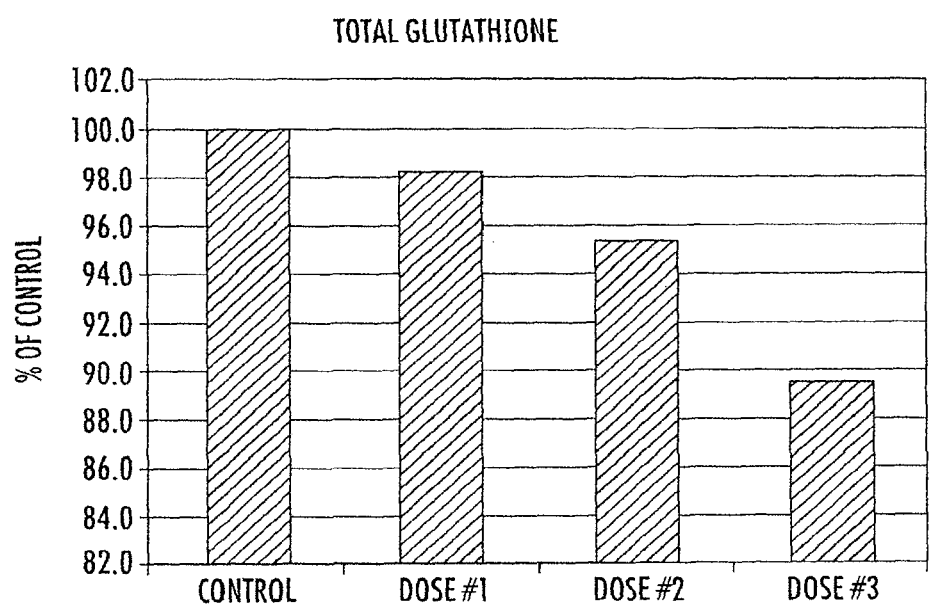
FIG. 9 shows the reduction in total glutathione concentration in MRSA as it correlates with reactive oxygen species (ROS) generation in these cells as the result of NIMELS irradiation (at several dosimetries); the decrease in glutathione concentration in lased samples is shown as percentage relative to the control.
Figure 10:
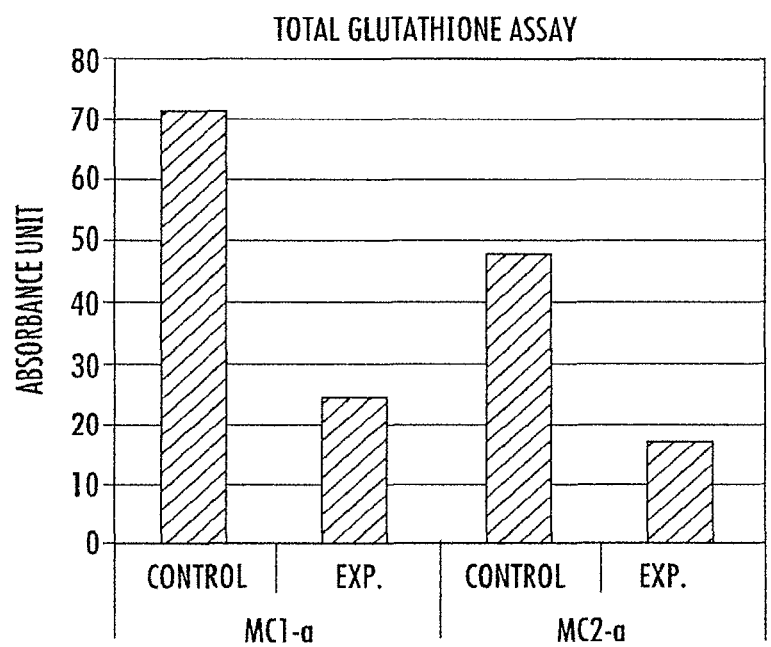
FIG. 10 shows the reduction in total glutathione concentration in human embryonic kidney cells as it correlates with reactive oxygen species (ROS) generation in these cells as the result of NIMELS irradiation (at two different dosimetries); the decrease in glutathione concentration in lased samples is shown as percentage relative to the control.
Figure 11:
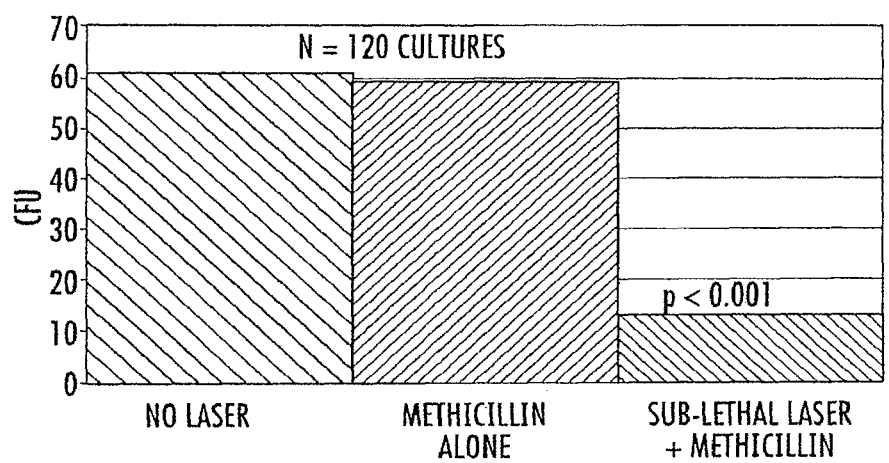
FIG. 11 shows the synergistic effects of NIMELS and methicillin in growth inhibition of MRSA colonies; data show methicillin is being potentiated by sub-lethal NIMELS dosimetry.
Figure 12:
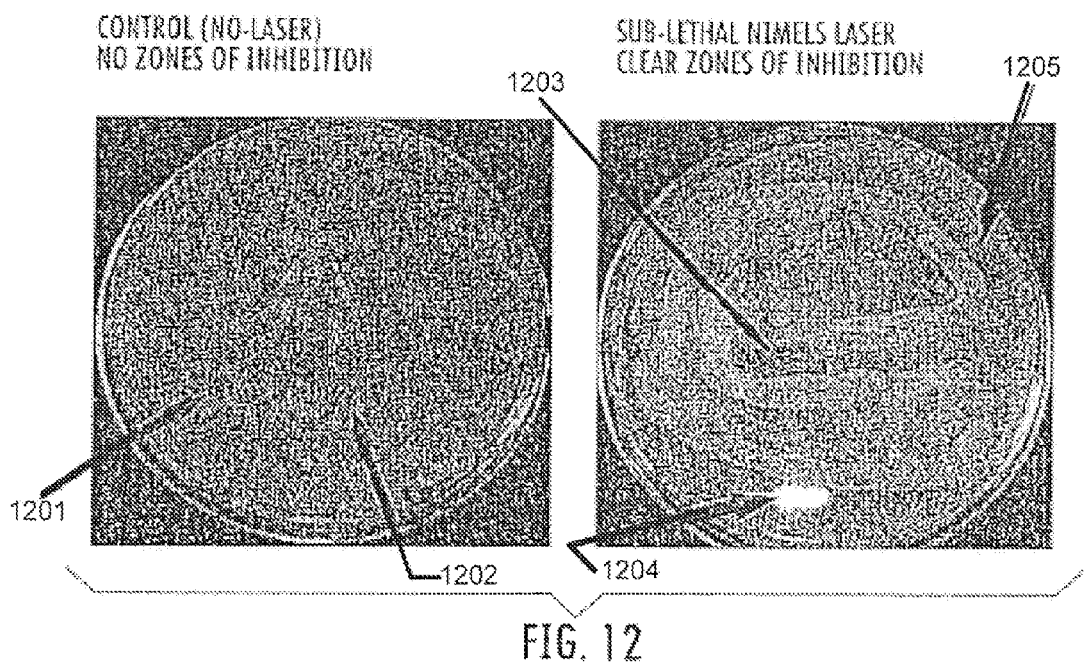
FIG. 12 shows the synergistic effects of NIMELS and bacitracin in growth inhibition of MRSA colonies; arrows indicate the growth (arrows 1201, 1202) or a lack thereof (arrows 1203, 1204, 1205) of MRSA colonies in the two samples shown; images show that bacitracin is being potentiated by sub-lethal NIMELS dosimetry.
Figure 13:
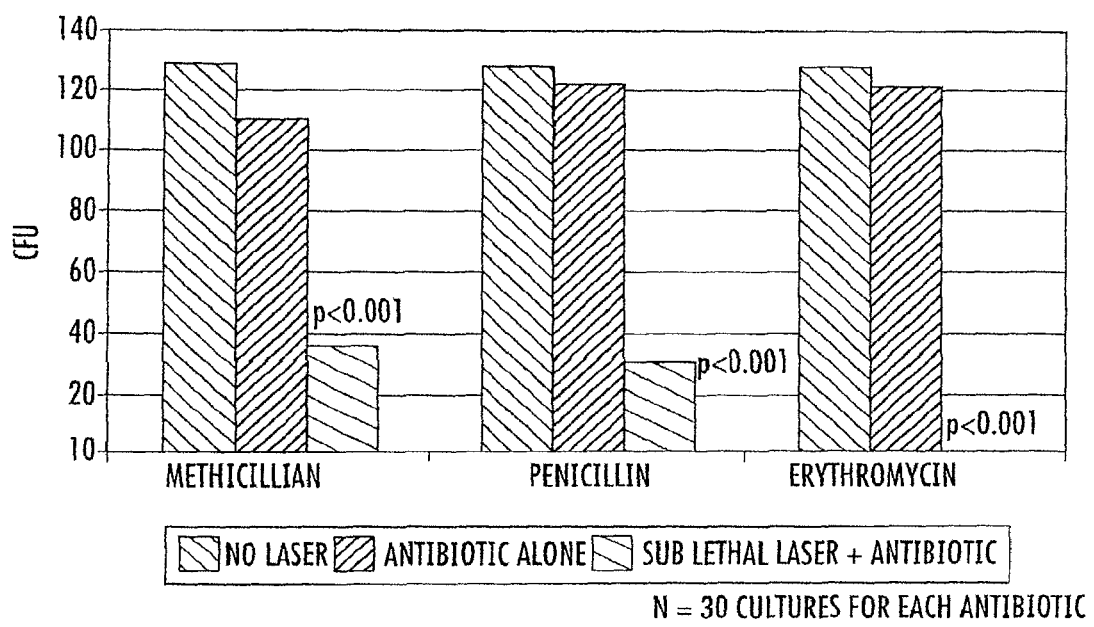
FIG. 13 shows a bar chart depicting the synergistic effects, as indicated by experimental data, of NIMELS with methicillin, penicillin and erythromycin in growth inhibition of MRSA colonies.
Figure 14:
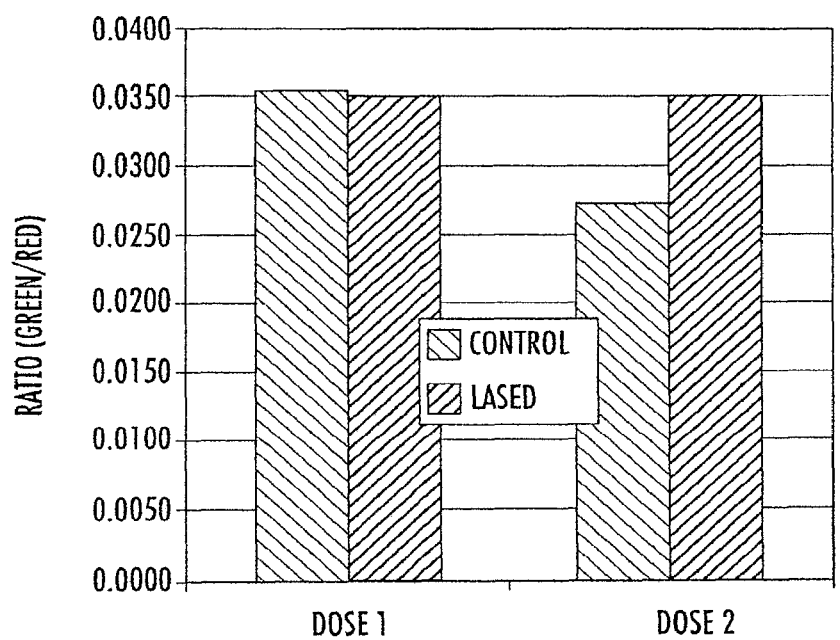
FIG. 14 illustrates the detection of decreased membrane potential in *E. coli* with sub-lethal NIMELS irradiation.

The data shows that $\mu_1-\mu_2>0$ as the lased cells had less "Green fluorescence" as seen in FIG. 8. These MRSA samples showed clear alteration and lowering of ΔΨ-steady-bact to one of ΔΨ-trans-bact with sub-lethal NIMELS dosimetry.

Figure 19:
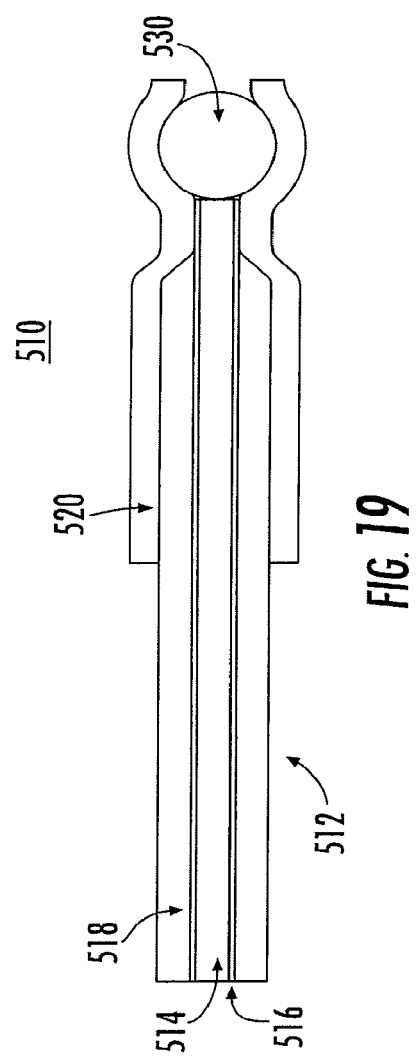
FIG. 19 shows the principal optical fiber, cladding, buffer, housing and optical element.

Detection of Membrane Potential ΔΨ in *E. coli*
Red/green ratios were calculated using population mean fluorescence intensities for control and lased samples at sub-lethal dosimetry:

The data shows that $\mu_1-\mu_2>0$ as the lased cells had less "Green fluorescence" as seen in FIG. 19. These *E. coli* samples showed clear alteration and lowering of ΔΨ-steady-bact to one of ΔΨ-trans-bact with sublethal NIMELS dosimetry.

Example VI

NIMELS In Vitro Tests for ΔΨ-Mito Human Embryonic Kidney Cells with Sub-Lethal Laser Dosimetry Hypothesis Testing:
The null hypothesis is $\beta_1-\mu_2=0$:
a) $\mu_1$ is fluorescence intensity in a mammalian control cell culture mitochondria (no laser) subjected to a Mitochondrial Membrane Potential Detection Kit
b) $\mu_2$ is fluorescence intensity in the same mammalian cell culture pre-irradiated with sub-lethal dosimetry from the NIMELS laser and subjected to a Mitochondrial Membrane Potential Detection Kit The data shows that the fluorescence of mitochondria is dissipated (less than control unlased cells) by pre-treatment (of the cells) with the NIMELS laser system, the results indicate that the NIMELS laser interacted with respiratory processes and oxidative phosphorylation of the cells in mitochondria of mammalian cells.

$$\mu_1 - \mu_2 = 0$$

Will uphold that the addition sub-lethal NIMEL irradiation on the mammalian cell culture mitochondria has no effect on $\Delta\Psi$-steady-mito-mam.

$$\mu_1 - \mu_2 > 0$$

Will uphold that the addition sub-lethal NIMEL irradiation on the mammalian cell culture has a dissipation or depolarization effect on $\Delta\Psi$-steady-mito-mam.

Materials and Methods:

Mitochondrial Membrane Potential Detection Kit (APO LOGIX JC-1) (Cell Technology Inc., 950 Rengstorff Ave, Suite D; Mountain View Calif. 94043). The loss of mitochondrial membrane potential ($\Delta\Psi$) is a hallmark for apoptosis. The APO LOGIX JC-1 Assay Kit measures the mitochondrial membrane potential in cells.

In non-apoptotic cells, JC-1 (5,5',6,6'-tetrachloro-1,1',3,3'-tetraethylbenz-imidazolylcarbocyanine iodide) exists as a monomer in the cytosol (green) and also accumulates as aggregates in the mitochondria which stain red. Whereas, in apoptotic and necrotic cells, JC-1 exists in monomeric form and stains the cytosol green.

TABLE 8

Mamallian Cell Dosimetries
First lasing procedure: Both 870 and 930
Second lasing procedure 930 alone

| Parameters | Output Power (W) | Beam Spot (cm) | Area of Spot (cm2) | Time (sec) |
|---|---|---|---|---|
| Test (H-2) 870 at 4.25 W and 930 at 4.25 W for 18 min followed by | 8.5 | 1.5 | 1.77 | 1080 |
| Test (H-2) 930 at 8.5 W for 10 min | 8.5 | 1.5 | 1.77 | 600 |

HEK-293 (Human Embryonic Kidney Cells) $\Delta\Psi$-Mito Tests:

The (APO LOGIX JC-1) kit measures membrane potential by conversion of green fluorescence to red fluorescence. The appearance of red color has been measured and plotted, which should only occur in cells with intact membranes, and the ratio of green to red is calculated for both control and lased samples.

Clearly in this test, the red fluorescence is reduced in the lased sample while the ratio of green to red increases, indicating depolarization. These results show that $\mu_1 - \mu_2 > 0$ and that sub-lethal NIMELS irradiation on the mammalian cell mitochondria has a dissipation or depolarization effect on $\Delta\Psi$-steady-mito-mam, indicating a clear reduction in mammalian $\Delta\Psi$-steady-mito-mam to $\Delta\Psi$-trans-mito-mam.

Example VII

NIMELS In Vitro Tests for Reactive Oxygen Species (ROS)

These in vitro tests for generation of reactive oxygen species (ROS) were carried on after laser alteration of bacterial trans-membrane $\Delta\Psi$-steady-bact to $\Delta\Psi$-trans-bact, $\Delta\Psi$-steady-mito-fungi to $\Delta\Psi$-trans-mito-fungi, and $\Delta\Psi$-steady-mito-mam to $\Delta\Psi$-trans-mito-mam with sub-lethal laser dosimetry comparable to those used in $\Delta\Psi$ tests above in previous examples.

Materials and Methods:

Total Glutathione Quantification Kit (Dojindo Laboratories; Kumamoto Techno Research Park, 2025-5 Tabaru, Mashiki-machi, Kamimashiki-gun; Kumamoto 861-2202, JAPAN)

Glutathione (GSH) is the most abundant thiol (SH) compound in animal tissues, plant tissues, bacteria and yeast. GSH plays many different roles such as protection against reactive oxygen species and maintenance of protein SH groups. During these reactions, GSH is converted into glutathione disulfide (GSSG: oxidized form of GSH). Since GSSG is enzymatically reduced by glutathione reductase, GSH is the dominant form in organisms. DTNB (5,5'-Dithiobis(2-nitrobenzoic acid)), known as Ellman's Reagent, was developed for the detection of thiol compounds. In 1985, it was suggested that the glutathione recycling system by DTNB and glutathione reductase created a highly sensitive glutathione detection method. DTNB and glutathione (GSH) react to generate 2-nitro-5-thiobenzoic acid and glutathione disulfide (GSSG). Since 2-nitro-5-thiobenzoic acid is a yellow colored product, GSH concentration in a sample solution can be determined by the measurement at 412 nm absorbance. GSH is generated from GSSG by glutathione reductase, and reacts with DTNB again to produce 2-nitro-5-thiobenzoic acid. Therefore, this recycling reaction improves the sensitivity of total glutathione detection.

At significant concentrations ROS will react rapidly and specifically with the target at a rate exceeding the rate of its reduction by the components of the glutathione antioxidant system (catalases, peroxidases, GSH).

Detection of Glutathione in MRSA at Sub-Lethal NIMELS Dosimetry that Alters $\Delta\Psi$-Steady-Bact to One of $\Delta\Psi$-Trans-Bact A reduction in total glutathione in MRSA at sub-lethal NIMELS dosimetry that alters that alters $\Delta\Psi$-steady-bact to one of $\Delta\Psi$-trans-bact, is proof of generation of ROS with sub-lethal alteration of Trans-membrane $\Delta\Psi$-steady-bact to one of $\Delta\Psi$-trans-bact.

Detection of Glutathione in E. coli at Sub-Lethal NIMELS Dosimetry that Alters Trans-Membrane $\Delta\Psi$-Steady to One of $\Delta\Psi$-Trans A reduction in total glutathione in E. coli at sub-lethal NIMELS dosimetry that alters $\Delta\Psi$-steady-bact to one of $\Delta\Psi$-trans-bact, is evidence of generation of ROS with sub-lethal alteration of Trans-membrane $\Delta\Psi$-steady-bact to one of $\Delta\Psi$-trans-bact.

Detection of glutathione in C. albicans at sub-lethal NIMELS that alters $\Delta\Psi$-steady-mito-fungi to $\Delta\Psi$-trans-mito-fungi and subsequently $\Delta\Psi$-steady-fungi to one of $\Delta\Psi$-trans-fungi.

Detection of Glutathione in C. albicans at Sub-Lethal NIMELS Dosimetry that Alters $\Delta\Psi$-Steady-Mito-Fungi to $\Delta\Psi$-Trans-Mito-Fungi and Subsequently $\Delta\Psi$-Steady-Fungi to One of $\Delta\Psi$-Trans-Fungi A reduction in total glutathione in C. albicans at sub-lethal NIMELS dosimetry that alters $\Delta\Psi$-steady-mito-fungi to $\Delta\Psi$-trans-mito-fungi and subsequently $\Delta\Psi$-steady-fungi to one of $\Delta\Psi$-trans-fungi, is proof of generation of ROS with sub-lethal alteration of Trans-membrane $\Delta\Psi$-steady-mito-fungi to $\Delta\Psi$-trans-mito-fungi and subsequently $\Delta\Psi$-steady-fungi to one of $\Delta\Psi$-trans-fungi.

Detection of Glutathione in HEK-293 (Human Embryonic Kidney Cells) at Sub-Lethal NIMELS Dosimetry that Alters $\Delta\Psi$-Steady-Mito-Mam to $\Delta\Psi$-Trans-Mito-Mam A reduction in total Glutathione in HEK-293 (Human Embryonic Kidney Cells) with sub-lethal NIMELS dosimetry that alters $\Delta\Psi$-steady-mito-mam to $\Delta\Psi$-trans-mito-mam, is proof of generation of ROS with NIMELS-mediated sub-lethal alteration of Trans-membrane ΔΨ-steady-mito-mam to ΔΨ-trans-mito-mam.

Example VIII

Assessment of the Impact of Sub-Lethal Doses of NIMELS Laser on MRSA with Erythromycin and Trimethoprim In this example, it was determined whether a sub-lethal dose of the NIMEL laser will potentiate the effect of the antibiotic erythromycin more than the antibiotic trimethoprim in MRSA. Efflux pumps play a major factor in erythromycin resistance. There are no reported trimethoprim efflux pump resistance mechanisms in the gram positive *S. aureus*.

Background: Erythromycin is a macrolide antibiotic that has an antibacterial spectrum of action very similar to that of the β-lactam penicillin. In the past, it has been effective in the treatment of a wide range of gram-positive bacterial infections effecting the skin and respiratory tract, and has been considered one of the safest antibiotics to use. In the past, erythromycin has been used for people with allergies to penicillins.

Erythromycin's mechanism of action is to prevent growth and replication of bacteria by obstructing bacterial protein synthesis. This is accomplished because erythromycin binds to the 23S rRNA molecule in the 50S of the bacterial ribosome, thereby blocking the exit of the growing peptide chain thus inhibiting the translocation of peptides. Erythromycin resistance (as with other marcolides) is rampant, wide spread, and is accomplished via two significant resistance systems:
A) modification of the 23S rRNA in the 50S ribosomal subunit to insensitivity
B) efflux of the drug out of cells Trimethoprim is an antibiotic that has historically been used in the treatment of urinary tract infections. It is a member of the class of antimicrobials known as dihydrofolate reductase inhibitors. Trimethoprim's mechanism of action is to interfere with the system of bacterial dihydrofolate reductase (DHFR), because it is an analog of dihydrofolic acid. This causes competitive inhibition of DHFR due to a 1000 fold higher affinity for the enzyme than the natural substrate.

Thus, trimethoprim inhibits synthesis of the molecule tetrahydrofolic acid. Tetrahydrofolic acid is an essential precursor in the de novo synthesis of the DNA nucleotide thymidylate. Bacteria are incapable of taking up folic acid from the environment (i.e., the infection host) and are thus dependent on their own de novo synthesis of tetrahydrofolic acid. Inhibition of the enzyme ultimately prevents DNA replication.

Trimethoprim resistance generally results from the overproduction of the normal chromosomal DHFR, or drug resistant DHFR enzymes. Reports of trimethoprim resistance *S. aureus* have indicated that the resistance is chromosomally of the mediated type or is encoded on large plasmids. Some strains have been reported to exhibit both chromosomal and plasmid-mediated trimethoprim resistance.
In the gram positive pathogen *S. aureus*, resistance to trimethoprim is due to genetic mutation, and there have been no reports that trimethoprim is actively effluxed out of cells.
Efflux Pumps in Bacteria A major route of drug resistance in bacteria and fungi is the active export (efflux) of antibiotics out of the cells such that a therapeutic concentration in not obtained in the cytoplasm of the cell.

Active efflux of antibiotics (and other deleterious molecules) is mediated by a series of transmembrane proteins in the cytoplasmic membrane of gram positive bacteria and the outer membranes of gram negative bacteria.

Clinically, antibiotic resistance that is mediated via efflux pumps, is most relevant in gram positive bacteria for marcolides, tetracyclines and fluoroquinolones. In gram negative bacteria, β-lactam efflux mediated resistance is also of high clinical relevance.
Hypothesis Testing The null hypothesis is $\mu_1-\mu_2=0$ and $\mu_1-\mu_3=0$ where:
a) $\mu_1$ is sub-lethal dosimetry from the NIMEL laser system on MRSA as a control and;
b) $\mu_2$ is the same sub-lethal dosimetry from the NIMEL laser system on MRSA with the addition of trimethoprim at resistant MIC just below effectiveness level and;
c) $\mu_3$ is the same sub-lethal dosimetry from the NIMEL laser system on MRSA with the addition of erythromycin at resistant MIC just below effectiveness level.

The data shows that the addition of the antibiotic trimethoprim or erythromycin, after sub-lethal irradiation, results in the reduction in growth of these MRSA colonies, as follows:

$$\mu_1-\mu_2=0$$

Will uphold that the addition of trimethoprim produces no deleterious effect after sub-lethal NIMEL irradiation, on normal growth of MRSA colonies.

$$\mu_1-\mu_2>0$$

Will uphold that the addition of trimethoprim produces a deleterious effect after sub-lethal NIMEL irradiation, on normal growth of MRSA colonies.

$$\mu_1-\mu_3=0$$

Will uphold that the addition of erythromycin produces no deleterious effect after sub-lethal NIMEL irradiation, on normal growth of MRSA colonies.

$$\mu_1-\mu_3>0$$

Will uphold that the addition of erythromycin produces a deleterious effect after sub-lethal NIMEL irradiation, on normal growth of MRSA colonies.

TABLE 9

| | EXPERIMENTAL | | | CONTROL (no laser) | | |
|---|---|---|---|---|---|---|
| | AGAR | trimeth 2 ug/ml | erythro 4 ug/ml | AGAR | trimeth 2 ug/ml | erythro 4 ug/ml |
| B-4 1 | 84 | 110 | 39 | B-4 1 | 180 | 213 | 196 |
| B-4 2 | 88 | 125 | 35 | B-4 2 | 230 | 198 | 168 |
| B-4 3 | 120 | 138 | 39 | B-4 3 | 241 | 240 | 175 |
| B-4 4 | 114 | 115 | 28 | B-4 4 | 220 | 220 | 177 |
| B-4 5 | 117 | 100 | 27 | B-4 5 | smeared | 145 | 195 |

Results:
This experiment clearly showed that under sub-lethal laser parameters with the NIMELS system, $\mu_1-_2=0$ and $\mu_1-\mu_3>=0$. This indicates that an efflux pump is being inhibited, and resistance to erythromycin being reversed by the NIMELS effect on ΔΨ-steady-bact of the MRSA.

Example IX

Assessment of the Impact of Sub-Lethal Doses of NIMELS Laser on MRSA with Tetracycline and Rifampin The purpose of this experiment was to observe if a sub-lethal dose of the NIMEL laser will potentiate the effect of the antibiotic tetracycline more than the antibiotic rifampin in MRSA. Efflux pumps are well researched, and play a major factor in tetracycline resistance. However, there are no reported rifampin efflux pump resistance mechanisms in the gram positive *S. aureus*.

This experiment was also previously run with erythromycin and trimethoprim, with data indicating that the NIMELS effect is able to damage efflux pump resistance mechanisms in erythromycin.

Tetracycline:

Tetracycline is considered a bacteriostatic antibiotic, meaning that it hampers the growth of bacteria by inhibiting protein synthesis. Tetracycline accomplishes this by inhibiting action of the bacterial 30S ribosome through the binding of the enzyme aminoacyl-tRNA. Tetracycline resistance is often due to the acquisition of new genes, which code for energy-dependent efflux of tetracyclines, or for a protein that protects bacterial ribosomes from the action of tetracyclines.

Rifampin:

Rifampin is a bacterial RNA polymerase inhibitor, and functions by directly blocking the elongation of RNA. Rifampicin is typically used to treat mycobacterial infections, but also plays a role in the treatment of methicillin-resistant *Staphylococcus aureus* (MRSA) in combination with fusidic acid, a bacteriostatic protein synthesis inhibitor. There are no reports of rifampin resistance via efflux pumps in MRSA.

Hypothesis:

The null hypothesis is $\mu_1-\mu_2=0$ and $\mu_1-\mu_3=0$ where:

a) $\mu_1$ is sub-lethal dosimetry from the NIMEL laser system on MRSA as a control and;

b) $\mu_2$ is the same sub-lethal dosimetry from the NIMEL laser system on MRSA with the addition of tetracycline at resistant MIC just below effectiveness level and;

c) $\mu_3$ is the same sub-lethal dosimetry from the NIMEL laser system on MRSA with the addition of rifampin at resistant MIC just below effectiveness level.

The data shows that the addition of the antibiotic tetracycline or rifampin, after sub-lethal irradiation, results in the reduction in growth of these MRSA colonies, as follows:

$\mu_1-\mu_2=0$

Will uphold that the addition of tetracycline produces no deleterious effect after sub-lethal NIMEL irradiation, on normal growth of MRSA colonies.

$\mu_1-\mu_2>0$

Will uphold that the addition of tetracycline produces a deleterious effect after sub-lethal NIMEL irradiation, on normal growth of MRSA colonies.

$\mu_1-\mu_3=0$

Will uphold that the addition of rifampin produces no deleterious effect after sub-lethal NIMEL irradiation, on normal growth of MRSA colonies.

$\mu_1-\mu_3>0$

Will uphold that the addition of rifampin produces a deleterious effect after sub-lethal NIMEL irradiation, on normal growth of MRSA colonies.

TABLE 10

| | EXPERIMENTAL | | | | CONTROL | | |
|---|---|---|---|---|---|---|---|
| | AGAR | rifampin 90 ug/ml | tetracyc. 4 ug/ml | | AGAR | rifampin 90 ug/ml | tetracyc. 4 ug/ml |
| E1-1 | 307 | 210 | 42 | E1-1 | 270 | 183 | 240 |
| E1-2 | 300 | 200 | 56 | E1-2 | 210 | 210 | 256 |
| E1-3 | 300 | 280 | 46 | E1-3 | 224 | 166 | 268 |
| E1-4 | 310 | 378 | 48 | E1-4 | semared | 228 | 310 |
| E1-5 | 250 | 280 | 42 | E1-5 | 215 | 188 | 255 |
| E2-1 | 246 | 272 | 18 | E2-1 | 240 | 274 | 280 |
| E2-2 | 254 | 320 | 28 | E2-2 | 310 | 210 | 283 |
| E2-3 | 174 | 330 | 27 | E2-3 | 190 | 180 | 263 |
| E2-4 | 170 | semared | 16 | E2-4 | 257 | 240 | 260 |
| E2-5 | 240 | 284 | 18 | E2-5 | 275 | | 310 |
| E3-1 | 310 | 270 | 72 | E3-1 | 280 | 288 | 368 |
| E3-2 | 280 | 225 | 67 | E3-2 | 320 | 280 | 380 |
| E3-3 | 260 | 284 | 45 | E3-3 | 310 | 210 | 375 |
| E3-4 | 210 | 200 | 47 | E3-4 | 320 | 290 | 390 |
| E3-5 | 220 | smeared | 74 | E3-5 | 320 | 300 | smeared |

Results:

This experiment clearly showed that under sub-lethal laser parameters with the NIMELS system, $\mu_1-\mu_2=0$ and $\mu_1-\mu_3>=0$. This indicates that an efflux pump is being inhibited, and resistance to tetracycline is being reversed by the NIMELS effect on $\Delta\Psi$-steady-bact of the MRSA.

Example X

Assessment of the Impact of Sub-Lethal Doses of NIMELS Laser on MRSA with Methicillin and $\Delta\Psi$-Plas-Bact Inhibition of Cell Wall Synthesis Methicillin:

Methicillin is a β-lactam that was previously used to treat infections caused by gram-positive bacteria, particularly β-lactamase-producing organisms such as *S. aureus* that would otherwise be resistant to most penicillins, but is no longer clinically used. The term methicillin-resistant *S. aureus* (MRSA) continues to be used to describe *S. aureus* strains resistant to all penicillins.

Mechanism of Action

Like other β-lactam antibiotics, methicillin acts by inhibiting the synthesis of peptidoglycan (bacterial cell walls).

It has been shown in the gram positive bacterium *Bacillus subtilis*, that the activities of peptidoglycan autolysins are increased (i.e., no longer inhibited) when the ETS was blocked by adding proton conductors. This suggests that $\Delta\Psi$-plas-bact and $\Delta\mu H^+$ (independent of storing energy for cellular enzymatic functions) potentially has a profound and exploitable influence on cell wall anabolic functions and physiology.

In addition, it has been reported that $\Delta\Psi$-plas-bact uncouplers inhibit peptidoglycan formation with the accumulation of the nucleotide precursors involved in peptidoglycan synthesis, and the inhibition of transport of N-acetylglucosamine (GlcNAc), one of the major biopolymers in peptidoglycan.

Hypothesis Testing:

Bacitracin will potentiate the multiple influences of an optically lowered $\Delta\Psi$-plas-bact on a growing cell wall (i.e., increased cell wall autolysis, inhibited cell wall synthesis). This is especially relevant in gram positive bacteria such as MRSA, that do not have efflux pumps as resistance mechanisms for cell wall inhibitory antimicrobial compounds.

The null hypothesis is $\mu_1-\mu_2=0$ and $\mu_1-\mu_3=0$ where:

a) $\mu_1$ is sub-lethal dosimetry from the NIMEL laser system on MRSA as a control and;

b) $\mu_2$ is the same sub-lethal dosimetry from the NIMEL laser system on MRSA with the addition of methicillin at resistant MIC just below effectiveness level and;

$$\mu_1-\mu_2=0$$

Will uphold that the addition of methicillin produces no deleterious effect after sub-lethal NIMEL irradiation, on normal growth of MRSA colonies.

$$\mu_1-\mu_2>0$$

Will uphold that the addition of methicillin produces a deleterious effect after sub-lethal NIMEL irradiation, on normal growth of MRSA colonies.

Figure 15:
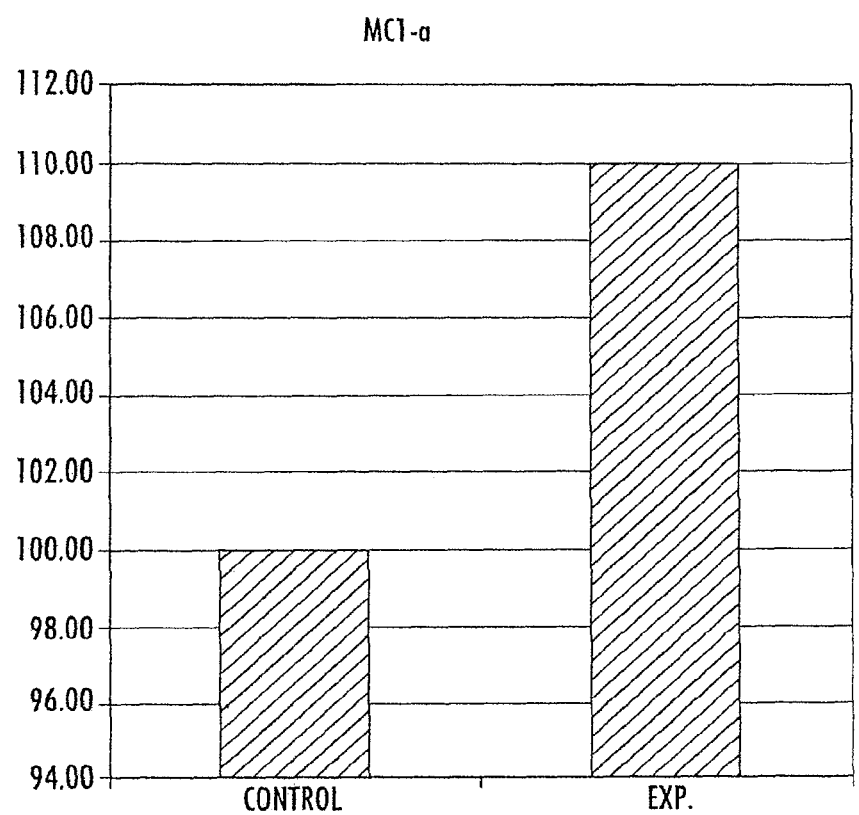
FIG. 15 illustrates the detection of increased glutathione in *E. coli* with sub-lethal NIMELS irradiation.

Results:

As shown in FIG. 15, this experiment clearly showed that under sub-lethal laser parameters with the NIMELS system, $\mu_1-\mu_2>=0$, meaning that the addition of methicillin produces a deleterious effect after sub-lethal NIMEL irradiation on normal growth of MRSA colonies as shown by CFU count. This suggest that methicillin (independent of an efflux pump) is being potentiated by the NIMELS effect on $\Delta\Psi$-steady-bact of the MRSA.

Hence, the NIMELS laser and its concomitant optical $\Delta\Psi$-plas-bact lowering phenomenon is synergistic with cell wall inhibitory antimicrobials in MRSA. Without wishing to be bound by theory, this must function via the inhibition of anabolic (periplasmic) ATP coupled functions, as MRSA does not have efflux pumps for methicillin.

Example XI

Assessment of the Impact of Sub-Lethal Doses of NIMELS Laser on MRSA with Bacitracin and $\Delta\Psi$-Plas-Bact Inhibition of Cell Wall Synthesis Bacitracin is a mixture of cyclic polypeptides produced by *Bacillus subtilis*. As a toxic and difficult-to-use antibiotic, bacitracin cannot generally be used orally, but is used topically.

Mechanism of Action:

Bacitracin interferes with the dephosphorylation of the $C_{55}$-isoprenyl pyrophosphate, a molecule which carries the building blocks of the peptidoglycan bacterial cell wall outside of the inner membrane in gram negative organisms and the plasma membrane in gram positive organism.

It has been shown in the gram positive bacterium *Bacillus subtilis*, that the activities of peptidoglycan autolysins are increased (i.e., no longer inhibited) when the ETS was blocked by adding proton conductors. This indicates that $\Delta\Psi$-plas-bact and $\Delta\mu H^+$ (independent of storing energy for cellular enzymatic functions) potentially has a profound and exploitable influence on cell wall anabolic functions and physiology.

In addition, it has been reported that $\Delta\Psi$-plas-bact uncouplers inhibit peptidoglycan formation with the accumulation of the nucleotide precursors involved in peptidoglycan synthesis, and the inhibition of transport of N-acetylglucosamine (GlcNAc), one of the major biopolymers in peptidoglycan.

Hypothesis Testing:

Bacitracin potentiates the multiple influences of an optically lowered $\Delta\Psi$-plas-bact on a growing cell wall (i.e., increased cell wall autolysis, inhibited cell wall synthesis). This is especially relevant in gram positive bacteria such as MRSA, that do not have efflux pumps as resistance mechanisms for cell wall inhibitory antimicrobial compounds.

The null hypothesis is $\mu_1-\mu_2=0$ and $\mu_1-\mu_3=0$ where:

a) $\mu_1$ is sub-lethal dosimetry from the NIMEL laser system on MRSA as a control and;

b) $\mu_2$ is the same sub-lethal dosimetry from the NIMEL laser system on MRSA with the addition of bacitracin at resistant MIC just below effectiveness level and;

$$\mu_1-\mu_2=0$$

Will uphold that the addition of bacitracin produces no deleterious effect after sub-lethal NIMEL irradiation, on normal growth of MRSA colonies.

$$\mu_1-\mu_2>0$$

Will uphold that the addition of bacitracin produces a deleterious effect after sub-lethal NIMEL irradiation, on normal growth of MRSA colonies.

Figure 16A:
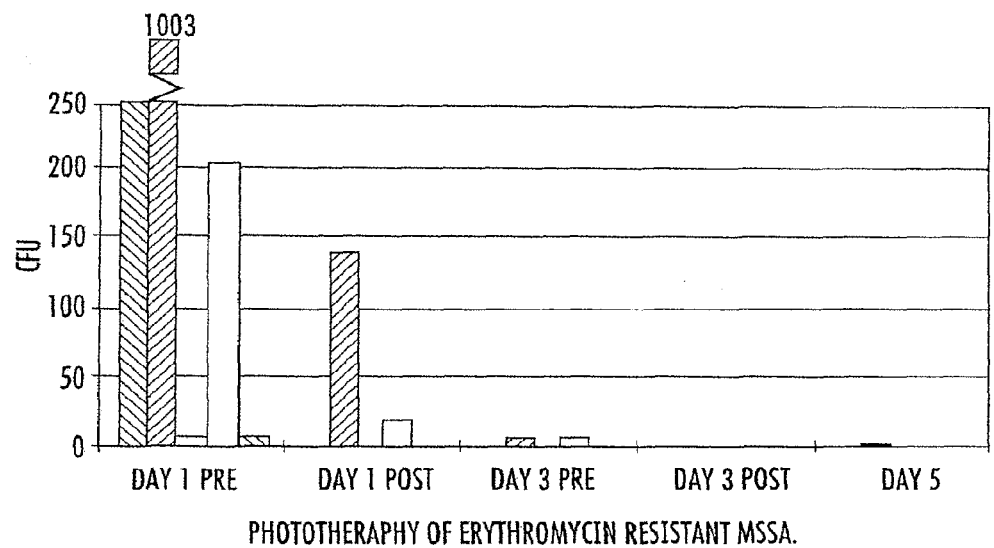
FIG. 16*a* illustrates five subjects initially culturing positive for erythromycin resistant MSSA, all showing positive responses to phototherapy.
Figure 16B:
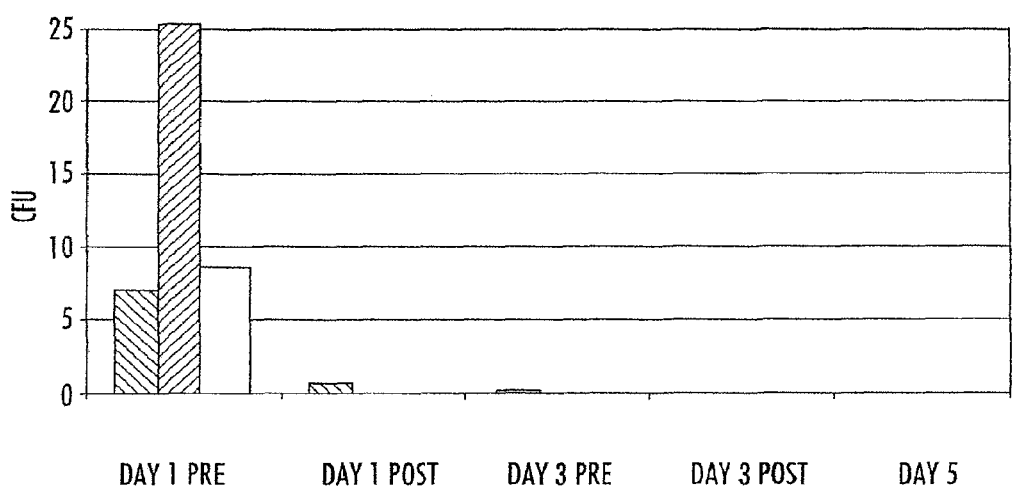
FIG. 16*b* illustrates three subjects initially culturing positive for erythromycin resistant MSRA, all showing positive responses to phototherapy.

Results:

As shown in FIG. 16, this experiment clearly showed that under sub-lethal laser parameters with the NIMELS system, $\mu_1-\mu_2>=0$, meaning that the addition of bacitracin produces a deleterious effect after sub-lethal NIMEL irradiation, on normal growth of MRSA colonies. In FIG. 16, arrows point to MRSA growth or a lack thereof in the two samples shown. This indicates that bacitracin (independent of an efflux pump) is being potentiated by the NIMELS effect on $\Delta\Psi$-steady-bact of the MRSA.

Hence, the NIMELS laser and its concomitant optical $\Delta\Psi$-plas-bact lowering phenomenon is synergistic with cell wall inhibitory antimicrobials in MRSA. Without wishing to be bound by theory, this most likely functions via the inhibition of anabolic (periplasmic) ATP coupled functions as MRSA does not have efflux pumps for bacitracin.

Example XII

NIMELS Dosimetry Calculations

The examples that follow describe selected experiments depicting the ability of the NIMELS approach to impact upon the viability of various commonly found microorganisms at the wavelengths described herein. The microorganisms exemplified include *E. coli* K-12, multi-drug resistant *E. coli*, *Staphylococcus aureus*, methicillin-resistant *S. aureus*, *Candida albicans*, and *Trichophyton rubrum*.

As discussed in more details supra, NIMELS parameters include the average single or additive output power of the laser diodes, and the wavelengths (870 nm and 930 nm) of the diodes. This information, combined with the area of the laser beam or beams (cm$^2$) at the target site, provide the initial set of information which may be used to calculate effective and safe irradiation protocols according to the invention.

The power density of a given laser measures the potential effect of NIMELS at the target site. Power density is a function of any given laser output power and beam area, and may be calculated with the following equations:

For a single wavelength:

$$\text{Power Density (W/cm}^2) = \frac{\text{Laser Output Power}}{\text{Beam Diameter (cm}^2)} \quad 1)$$

For dual wavelength treatments:

$$\text{Power Density (W/cm}^2) = \quad 2)$$
$$\frac{\text{Laser (1) Output Power}}{\text{Beam Diameter (cm}^2)} + \frac{\text{Laser (2) Output Power}}{\text{Beam Diameter (cm}^2)}$$

Beam area can be calculated by either:

$$\text{Beam Area (cm}^2) = \text{Diameter (cm)}^2 * 0.7854 \text{ or Beam Area (cm}^2) = \text{Pi} * \text{Radius (cm)}^2 \quad 3)$$

The total photonic energy delivered into the tissue by one NIMELS laser diode system operating at a particular output power over a certain period is measured in Joules, and is calculated as follows:

$$\text{Total Energy (Joules)} = \text{Laser Output Power (Watts)} * \text{Time (Secs.)} \quad 4)$$

The total photonic energy delivered into the tissue by both NIMELS laser diode systems (both wavelengths) at the same time, at particular output powers over a certain period, is measured in Joules, and is calculated as follows:

$$\text{Total Energy (Joules)} = \quad 5)$$
$$[\text{Laser (1) Output Power (Watts)} * \text{Time (Secs)}] +$$
$$[\text{Laser (2) Output Power (Watts)} * \text{Time (Secs)}]$$

In practice, it is useful (but not necessary) to know the distribution and allocation of the total energy over the irradiation treatment area, in order to correctly measure dosage for maximal NIMELS beneficial response. Total energy distribution may be measured as energy density (Joules/cm$^2$). As discussed infra, for a given wavelength of light, energy density is the most important factor in determining the tissue reaction. Energy density for one NIMELS wavelength may be derived as follows:

$$\text{Energy Density (Joules/cm}^2) = \quad 6)$$
$$\frac{\text{Laser Output power (Watts)} * \text{Time (secs)}}{\text{Beam Area (cm}^2)}$$

$$\text{Energy Density (Joule/cm}^2) = \text{Power Density (W/cm}^2) * \text{Time (secs)} \quad 7)$$

When two NIMELS wavelengths are being used, the energy density may be derived as follows:

$$\text{Energy Density (Joules/cm}^2) = \quad 8)$$
$$\frac{\text{Laser (1) Output power (Watts)} * \text{Time (secs)}}{\text{Beam Area (cm}^2)} +$$
$$\frac{\text{Laser (2) Output power (Watts)} * \text{Time (secs)}}{\text{Beam Area (cm}^2)}$$

or, $$\text{Energy Density (Joule/cm2)} = \quad 9)$$
$$\text{Power Density (1) (W/cm}^2) * \text{Time (Secs)} +$$
$$\text{Power Density (2) (W/cm}^2) * \text{Time (Secs)}$$

To calculate the treatment time for a particular dosage, a practitioner may use either the energy density (J/cm$^2$) or energy (J), as well as the output power (W), and beam area (cm$^2$) using either one of the following equations:

$$\text{Treatment Time (seconds)} = \frac{\text{Energy Density (Joules/cm}^2)}{\text{Output power Density (W/cm}^2)} \quad 10)$$

$$\text{Treatment Time (seconds)} = \frac{\text{Energy (Joules)}}{\text{Laser Output Power (Watts)}} \quad 11)$$

Because dosimetry calculations such as those exemplified in this Example can become burdensome, the therapeutic system may also include a computer database storing all researched treatment possibilities and dosimetries. The computer (a dosimetry and parameter calculator) in the controller is preprogrammed with algorithms based on the above-described formulas, so that any operator can easily retrieve the data and parameters on the screen, and input additional necessary data (such as: spot size, total energy desired, time and pulse width of each wavelength, tissue being irradiated, bacteria being irradiated) along with any other necessary information, so that any and all algorithms and calculations necessary for favorable treatment outcomes can be generated by the dosimetry and parameter calculator and hence run the laser.

In the examples that follow, in summary, when the bacterial cultures were exposed to the NIMELS laser, the bacterial kill rate (as measured by counting Colony Forming Units or CFU on post-treatment culture plates) ranged from 93.7% (multi-drug resistant *E. coli*) to 100% (all other bacteria and fungi).

Example XIII

Bacterial Methods: NIMELS Treatment Parameters for In Vitro *E. coli* Targeting

The following parameters illustrate the methods according to the invention as applied to *E. coli*, at final temperatures well below those associated in the literature with thermal damage.

A. Experiment Materials and Methods for *E. coli* K-12.

*E. coli* K12 liquid cultures were grown in Luria Bertani (LB) medium (25 g/L). Plates contained 35 mL of LB plate medium (25 g/L LB, 15 g/L bacteriological agar). Culture dilutions were performed using PBS. All protocols and manipulations were performed using sterile techniques.

B. Growth Kinetics

Drawing from a seed culture, multiple 50 mL LB cultures were inoculated and grown at 37° C. overnight. The next morning, the healthiest culture was chosen and used to inoculate 5% into 50 mL LB at 37° C. and the O.D.$_{600}$ was monitored over time taking measurements every 30 to 45 minutes until the culture was in stationary phase.

C. Master Stock Production

Starting with a culture in log phase (O.D.$_{600}$ approximately 0.75), 10 mL were placed at 4° C. 10 mL of 50% glycerol were added and was aliquoted into 20 cryovials and snap frozen in liquid nitrogen. The cryovials were then stored at −80° C.

D. Liquid Cultures

Liquid cultures of *E. coli* K12 were set up as described previously. An aliquot of 100 µL was removed from the sub-culture and serially diluted to 1:1200 in PBS. This dilution was allowed to incubate at room temperature approximately 2 hours or until no further increase in O.D.$_{600}$ was observed in order to ensure that the cells in the PBS suspension would reach a static state (growth) with no significant doubling and a relatively consistent number of cells could be aliquoted further for testing.

Once it was determined that the K12 dilution was in a static state, 2 mL of this suspension were aliquoted into selected wells of 24-well tissue culture plates for selected NIMELS experiments at given dosimetry parameters. The plates were incubated at room temperature until ready for use (approximately 2 hrs).

Following laser treatments, 100 µl was removed from each well and serially diluted to 1:1000 resulting in a final dilution of 1:12×10$^5$ of initial K12 culture. Aliquots of 3×200 L of each final dilution were spread onto separate plates in triplicate. The plates were then incubated at 37° C. for approximately 16 hours. Manual colony counts were performed and recorded. A digital photograph of each plate was also taken. Similar cell culture and kinetic protocols were performed for all NIMELS irradiation tests with *S. aureus* and *C. albicans* in vitro tests. For example, *C. albicans* ATCC 14053 liquid cultures were grown in YM medium (21 g/L, Difco) medium at 37° C. A standardized suspension was aliquoted into selected wells in a 24-well tissue culture plate. Following laser treatments, 100 µL was removed from each well and serially diluted to 1:1000 resulting in a final dilution of 1:5×10$^5$ of initial culture. 3×100 µL of each final dilution were spread onto separate plates. The plates were then incubated at 37° C. for approximately 16-20 hours. Manual colony counts were performed and recorded. A digital photograph of each plate was also taken.

*T. rubrum* ATCC 52022 liquid cultures were grown in peptone-dextrose (PD) medium at 37° C. A standardized suspension was aliquoted into selected wells in a 24-well tissue culture plate. Following laser treatments, aliquots were removed from each well and spread onto separate plates. The plates were then incubated at 37° C. for approximately 91 hours. Manual colony counts were performed and recorded after 66 hours and 91 hours of incubation. While control wells all grew the organism, 100% of laser-treated wells as described herein had no growth. A digital photograph of each plate was also taken.

Thermal tests performed on PBS solution, starting from room temperature. Ten (10) Watts of NIMELS laser energy were available for use in a 12 minute lasing cycle, before the temperature of the system is raised close to the critical threshold of 44° C.

TABLE 11

Time & Temperature measurements for In Vitro NIMELS Dosimetries

| NIMEL OUTPUT POWER (W) | BEAM SPOT 1.5 CM DIAMETER OVERLAP AREA (CM$^2$) | TREATMENT TIME (SEC) | TOTAL ENERGY (JOULES) | ENERGY DENSITY (RADIANT EXPOSURE) (J/CM$^2$) | POWER DENSITY (IRRADIANCE) (W/CM$^2$) | TEMPERATURE START | TEMP FINISH |
|---|---|---|---|---|---|---|---|
| Plate 1-N -- 3.0 + 3.0 = 6.0 | 1.76 | 720 | 4320 | 2448 | 3.40 | 20.5° C. | 34.0° C. |
| Plate 2-N -- 3.5 + 3.5 = 7.0 | 1.76 | 720 | 5040 | 2858 | 3.97 | 20.7° C. | 36.5° C. |
| Plate 3-N - 4.0 + 4.0 = 8.0 | 1.76 | 720 | 5760 | 3268 | 4.54 | 21.0° C. | 38.5° C. |
| Plate 4-N - 4.5 + 4.5 = 9.0 | 1.76 | 720 | 6480 | 3679 | 5.11 | 2.0° C. | 41.0° C. |
| Plate 5-N - 5.0 + 5.0 = 10. | 1.76 | 720 | 7200 | 4089 | 5.68 | 21.0° C. | 40.5° C. |
| Plate 6-N - 5.5 + 5.5 = 11 | 1.76 | 720 | 7920 | 4500 | 6.25 | 21.0° C. | 46.0° C. |
| Plate 7-N - 7.0 + 7.0 = 14.0 | 1.76 | 360 | 5040 | 2863 | 7.95 | 21.0° C. | 47.0° C. |
| Plate 8-N - 7.5 + 7.5 = 15 | 1.76 | 360 | 5400 | 3068 | 8.52 | 21.7° C. | 47.2° C. |

Example XIV

Dosimetry Values for NIMELS Laser Wavelength 930 nm for *E. coli* In Vitro Targeting The instant experiment demonstrates that the NIMELS single wavelength λ=930 nm is associated with quantitatable antibacterial efficacy against *E. coli* in vitro within safe thermal parameters for mammalian tissues.

Experimental data in vitro demonstrates that if the threshold of total energy into the system with 930 nm alone of 5400 J and an energy density of 3056 J/cm$^2$ is met in 25% less time, 100% antibacterial efficacy is still achievable.

TABLE 12

Sub-thermal NIMELS (λ = 930) Dosimetry for In Vitro *E. coli* Targeting

| OUTPUT POWER (W) | BEAM SPOT (CM) | TIME (SEC.) | TOTAL ENERGY JOULES | ENERGY DENSITY (J/CM$^2$) | POWER DENSITY (W/CM$^2$) | *E-COLI* KILL PERCENTAGE |
|---|---|---|---|---|---|---|
| 7.0 | 1.5 | 720 | 5040 | 2852 | 3.96 | 40.2% |
| 8.0 | 1.5 | 720 | 5760 | 3259 | 4.53 | 100.0% |
| 10.0 | 1.5 | 540 | 5400 | 3056 | 5.66 | 100.0% |

Experimental data in vitro also demonstrates that treatments using a single energy with λ=930 nm has antibacterial in vitro efficacy against the bacterial species *S. aureus* within safe thermal parameters for mammalian tissues.

It is also believed that if the threshold of total energy into the system of 5400 J and an energy density of 3056 J/cm$^2$ is met in 25% less time with *S. aureus* and other bacterial species, that 100% antibacterial efficacy will still be achieved.

TABLE 13

Sub-thermal NIMELS (λ = 930) Dosimetry for In Vitro *S. aureus* Targeting

| OUTPUT POWER (W) | BEAM SPOT (CM) | TIME (SEC) | TOTAL ENERGY JOULES | ENERGY DENSITY (J/CM$^2$) | POWER DENSITY (W/CM$^2$) | *S AUREUS* KILL PERCENTAGE |
|---|---|---|---|---|---|---|
| 7.0 | 1.5 | 720 | 5040 | 2852 | 3.96 | 24.1% |
| 8.0 | 1.5 | 720 | 5760 | 3259 | 4.53 | 100.0% |

Experimental in vitro data also showed that the NIMELS single wavelength of λ=930 nm has anti-fungal efficacy against in vitro *C. albicans* at ranges within safe thermal parameters for mammalian tissues.

It is also believed that if the threshold of total energy into the system of 5400 J and an energy density of 3056 J/cm$^2$ is met in 25% less time, that 100% antifungal efficacy will still be achieved.

TABLE 14

Sub-thermal NIMELS (λ = 930) Dosimetry for In Vitro *C. albicans* Targeting

| OUTPUT POWER (W) | BEAM SPOT (CM) | TIME (SEC.) | TOTAL ENERGY JOULES | ENERGY DENSITY (J/CM$^2$) | POWER DENSITY (W/CM$^2$) | *CANDIDA ALBICANS* KILL PERCENTAGE |
|---|---|---|---|---|---|---|
| 8.0 | 1.5 | 720 | 5760 | 3259 | 4.53 | 100.0% |
| 9.0 | 1.5 | 720 | 6840 | 3681 | 5.11 | 100.0% |

Example XV

Dosimetry Values for NIMELS Laser Wavelength 870 nm In Vitro

Experimental in vitro data also demonstrates that no significant kill is achieved up to a total energy of 7200 J, and energy density of 4074 J/cm$^2$ and a power density of 5.66 0 W/cm$^2$ with the wavelength of 870 nm alone against *E. coli*.

enhance the effect of the antibacterial efficacy of the second 930 nm NIMELS wavelength irradiance.

Experimental in vitro data demonstrates that this synergistic effect (combining the 870 nm wavelength to the 930 nm wavelength) allows for the 930 nm optical energy to be reduced. As shown herein, the optical energy was reduced to approximately ⅓ of the total energy and energy density

TABLE 15

*E. coli* Studies - Single wavelength λ = 870 nm

| OUTPUT POWER (W) | BEAM SPOT (CM) | TIME (SEC.) | TOTAL ENERGY JOULES | ENERGY DENSITY (J/CM$^2$) | POWER DENSITY (W/CM$^2$) | CONTROL CFUS | NIMELS CFUS | DIFFERENCE CONTROL - NIMEL | *E. COLI* KILL PERCENTAGE |
|---|---|---|---|---|---|---|---|---|---|
| 6.0 | 1.5 | 720 | 4320 | 2445 | 3.40 | 90 | 95 | (5) | −5.6% |
| 7.0 | 1.5 | 720 | 5040 | 2852 | 3.96 | 94 | 94 | 0 | 0.0% |
| 8.0 | 1.5 | 720 | 5760 | 3259 | 4.53 | 93 | 118 | (25) | −26.9% |
| 9.0 | 1.5 | 720 | 6480 | 3667 | 5.09 | 113 | 112 | 1 | 0.9% |
| 10.0 | 1.5 | 720 | 7200 | 4074 | 5.66 | 103 | 111 | (8) | −7.8% |
| 10.0 | 1.5 | 540 | 5400 | 3056 | 5.66 | 120 | 101 | 19 | 15.8% |

Comparable results using radiation having λ = 870 nm alone were also observed with *S. aureus*.

Example XVI

NIMELS Unique Alternating Synergistic Effect Between 870 nm and 930 nm Optical Energies Experimental in vitro data also demonstrates that there is a greater than additive effect between the two NIMELS wavelengths (λ=870 nm and 930 nm) when they are alternated (870 nm before 930 nm). The presence of the 870 nm NIMELS wavelength as a first irradiance has been found to enhance... required for NIMELS 100% *E. coli* antibacterial efficacy, when the (870 nm before 930 nm) wavelengths are combined in an alternating manner.

Experimental in vitro data also demonstrates that this synergistic mechanism can allow for the 930 nm optical energy (total energy and energy density) to be reduced to approximately ½ of the total energy density necessary for NIMELS 100% *E. coli* antibacterial efficacy if equal amounts of 870 nm optical energy are added to the system before the 930 nm energy at 20% higher power densities.

TABLE 16

*E. coli* data from Alternating NIMELS Wavelengths

| OUTPUT POWER (W) | SPOT (CM) | TIME (SEC.) | TOTAL ENERGY JOULES | ENERGY DENSITY (J/CM$^2$) | POWER DENSITY (W/CM$^2$) | *E. COLI* KILL PERCENTAGE |
|---|---|---|---|---|---|---|
| 8 W/8 W | 1.5 | 540/180 12 min. | 4320/1440 = 5760 | 2445/815 = 3529 | 4.53/4.53 | 100.0% |
| 10 W/10 W | 1.5 | 240/240 8 min. | 2400/2400 = 4800 | 1358/1358 = 2716 | 5.66/5.66 | 100.0% |

This synergistic ability is significant to human tissue safety, as the 930 nm optical energy heats up tissues at a greater rate than the 870 nm optical energy, and it is beneficial to a mammalian system to produce the least amount of heat possible during treatment.

It is also believed that if the NIMELS optical energies (870 nm and 930 nm) are alternated in the above manner with other bacterial species, that the 100% antibacterial effect will be essentially the same.

Example XVII

NIMELS Unique Simultaneous Synergistic Effect Between $\lambda$=870 nm and $\lambda$=930 nm Optical Energies Experimental in vitro data also demonstrates that there is a greater than additive effect between the two NIMELS wavelengths (870 nm and 930 nm) when they are used simultaneously (870 nm combined with 930 nm). The presence of the 870 nm NIMELS wavelength and the 930 nm NIMELS wavelength as a simultaneous irradiance absolutely enhances the effect of the antibacterial efficacy of the NIMELS system.

In vitro experimental data (see, for example, Tables IX and X below) demonstrated that by combining $\lambda$=870 nm and $\lambda$=930 nm (in this example used simultaneously) effectively reduces the 930 nm optical energy and density by about half of the total energy and energy density required when using a single treatment according to the invention.

TABLE 17

*E. coli* data from Combined NIMEL Wavelengths

| OUTPUT POWER (W) 870 NM/ 930 NM | BEAM SPOT (CM) | TIME (SEC) | TOTAL ENERGY JOULES | ENERGY DENSITY (J/CM$^2$) | POWER DENSITY (W/CM$^2$) | E-COLI KILL PERCENTAGE |
|---|---|---|---|---|---|---|
| 5 W + 5 W = 10 | 1.5 | 720 | 3600 (×2) = 7200 | 2037 (×2) = 4074 | 5.66 | 100% |

This simultaneous synergistic ability is significant to human tissue safety, as the 930 nm optical energy, heats up a system at a greater rate than the 870 nm optical energy, and it is beneficial to a mammalian system to produce the least amount of heat possible during treatment.

Thus, NIMELS wavelengths ($\lambda$=870 nm and 930 nm) may be used to achieve antibacterial and anti-fungal efficacy in an alternating mode or simultaneously or in any combination of such modes thereby reducing the exposure at the $\lambda$=930 associated with temperature increases which are minimized.

Experimental in vitro data also demonstrates that when *E. coli* is irradiated alone with a (control) wavelength of $\lambda$=830 nm, at the following parameters, the control 830 nm laser produced zero antibacterial efficacy for 12 minutes irradiation cycles, at identical parameters to the minimum NIMELS dosimetry associated with 100% antibacterial and anti-fungal efficacy with radiation of $\lambda$=930 nm.

TABLE 18

*E. coli* Single Wavelength $\lambda$ = 830 nm

| OUTPUT POWER (W) | BEAM SPOT (CM) | TIME (SEC.) | TOTAL ENERGY JOULES | ENERGY DENSITY (J/CM$^2$) | POWER DENSITY (W/CM$^2$) |
|---|---|---|---|---|---|
| 8.0 | 1.5 | 720 | 5760 | 3259 | 4.53 |
| 9.0 | 1.5 | 720 | 6480 | 3667 | 5.09 |

Experimental in vitro data also demonstrates that when applied at safe thermal dosimetries, there is little additive effect when using radiance of $\lambda$=830 nm in combination with $\lambda$=930 nm. The presence of the 830 nm control wavelength as a first irradiance is far inferior to the enhancement effect of the 870 nm NIMELS wavelength in producing synergistic antibacterial efficacy with the second 930 nm NIMELS wavelength.

TABLE 19

E. coli data from Substituted alternating 830 nm control Wavelength

| OUTPUT POWER (W) 830 NM/ 930 NM | BEAM SPOT (CM) | TIME (SEC) | TOTAL ENERGY JOULES | ENERGY DENSITY (J/CM$^2$) | POWER DENSITY (W/CM$^2$) | E. COLI KILL PERCENTAGE |
|---|---|---|---|---|---|---|
| 8 W/8 W | 1.5 | 540/ 180 12 min | 4320/ 1440 = 5760 | 2445/815 = 3529 | 4.53/4.53 | 0% |
| 10 W/10 W | 1.5 | 240/ 240 8 min | 2400/ 2400 = 4800 | 1358/1358 = 2716 | 5.66/5.66 | 65% |

Experimental in vitro data also demonstrates that when applied at safe thermal dosimetries, there is less additive effect with the 830 nm wavelength, and the NIMELS 930 nm wavelength when they are used simultaneously. In fact, experimental in vitro data demonstrates that 17% less total energy, 17% less energy density, and 17% less power density is required to achieve 100% E. coli antibacterial efficacy when 870 nm is combined simultaneously with 930 nm vs. the commercially available 830 nm. This, again, substantially reduces heat and harm to an in vivo system being treated with the NIMELS Thermal Parameters:

Experimental in vitro data also demonstrates that the NIMELS laser system can accomplish 100% antibacterial and anti-fungal efficacy within safe thermal tolerances for human tissues.

Example XVI

The Effects of Lower Temperatures on NIMELS

Cooling of Bacterial species:

Experimental in vitro data also demonstrated that by substantially lowering the starting temperature of bacterial

TABLE 20

E. coli data from Substituted Simultaneous 830 nm control Wavelength

| OUTPUT POWER (W) 830 NM/ 930 NM | BEAM SPOT (CM) | TIME (SEC) | TOTAL ENERGY JOULES | ENERGY DENSITY (J/CM$^2$) | POWER DENSITY (W/CM$^2$) | E-COLI KILL PERCENTAGE |
|---|---|---|---|---|---|---|
| 5 W + 5 W = 10 | 1.5 | 720 | 3600(×2) = 7200 | 2037(×2) = 4074 | 5.66 | 91% |
| 5.5 W + 5.5 = 11 W | 1.5 | 720 | 3960 (×2) = 7920 | 2250(×2) = 4500 | 6.25 | 90% |
| 6 W + 6 W = 12 W | 1.5 | 720 | 3960 (×2) = 8640* | 2454(×2) = 4909* | 6.81* | 100% |

Amount of Bacteria Killed:

In vitro data also showed that the NIMELS laser system in vitro is effective (within thermal tolerances) against solutions of bacteria containing 2,000,000 (2×10$^6$) Colony Forming Units (CFU's) of E. coli and S. aureus. This is a 2× increase over what is typically seen in a 1 gm sample of infected human ulcer tissue. Brown et al. reported that microbial cells in 75% of the diabetic patients tested were all at least 100,000 CFU/gm, and in 37.5% of the patients, quantities of microbial cells were greater than 1,000,000 (1×10$^6$) CFU (see Brown et al., Ostomy Wound Management, 401:47, issue 10, (2001), the entire teaching of which is incorporated herein by reference). samples to 4° C. for two hours in PBS before lasing cycle, that optical antibacterial efficacy was not achieved at any currently reproducible antibacterial energies with the NIMELS laser system.

Example XIX

MRSA/Antimicrobial Potentiation

This example shows the use of NIMELS wavelengths (λ=830 nm and 930 nm) in in vitro targeting of MRSA to increase antimicrobial sensitivity to methicillin. Four separate experiments have been performed. The data sets for these four experiments are presented in the tables that follow. See, also, FIG. 17, which shows: (a) the synergistic effects of NIMELS with methicillin, penicillin and erythromycin in growth inhibition of MRSA colonies; data show that penicillin and methicillin is being potentiated by sub-lethal NIMELS dosimetry by inhibiting the Bacterial Plasma Membrane Proton-motive force (Δp-plas-Bact) thereby inhibiting peptidoglycan synthesis anabolic processes that are co-targeted with the drug; and (b) that erythromycin is potentiated to a greater extent, because the Nimels effect is inhibiting the Bacterial Plasma Membrane Proton-motive force (Δp-plasBact) that supplies the energy for protein synthesis anabolic processes and erythromycin resistance efflux pumps.

General Methods for CFU Counts:

TABLE 21

| Time (hrs) | Task |
|---|---|
| T −18 | Inoculate overnight culture |
|  | 50 ml directly from glycerol stock |
| T −4 | Set up starter cultures |
|  | Three dilutions 1:50, 1:125, 1:250 |
|  | Monitor $OD_{600}$ of starter cultures |
| T 0 | Preparation of plating culture |
|  | At 10:00 am, the culture which is at $OD_{600} = 1.0$ is diluted 1:300 in PBS (50 mls final volume) and stored at RT for 1 hour. |
|  | (Room temp should be ~25° C.) |
| T +1 | Seeding of 24-well plates |
|  | 2 ml aliquots are dispensed into pre-designated wells in 24-well plates and transferred to NOMIR (8 24-well plates total) |
| T +2 to +8 | Dilution of treated samples |
|  | After laser treatment, 100 μl from each well is diluted serially to a final dilution of 1:1000 in PBS. |
|  | Plating of treated samples |
|  | 100 μl of final dilution is plated in triplicate on TSB agar with and without 30 μg/ml methicillin. (6 TSB plates per well) |
|  | Plates are incubated at 37° C. 18-24 hrs. |
| T +24 | Colonies are counted on each plate (96 plates total) |

TABLE 22

MRSA Dosimetry Progression 11-06-06 Experiment #1

First lasing procedure: Both 870 and 930

Second lasing procedure 930 alone

| Parameters | Output Power (W) | Beam Spot (cm) | Area of Spot (cm2) | Time (sec) | Total Energy Joules | Energy Density (J/cm$^2$) | Power Density (W/cm$^2$) | Temp Initial C. | Temp Final C. |
|---|---|---|---|---|---|---|---|---|---|
| Test (1) 870 at 5 W and 930 at 5 W for 12 min followed by | 10.0 | 1.5 | 1.77 | 720 | 7200 | 4074 | 5.66 | 24.4 | 44 |
| Test (1) 930 at 8 W for 6 min | 8.0 | 1.5 | 1.77 | 360 | 2880 | 1630 | 4.53 | 44 | 46.8 |
| Test (2) 870 at 5.5 W and 930 at 5.5 W for 12 min followed by | 11.0 | 1.5 | 1.77 | 720 | 7920 | 4482 | 6.22 | 26.5 | 48.1 |
| Test (2) 930 at 8 W for 6 min | 8.0 | 1.5 | 1.77 | 360 | 2880 | 1630 | 4.53 | 48.1 | 47.4 |
| Test (3) 870 at 5.5 W and 930 at 5.5 W for 10 min followed by | 10.0 | 1.5 | 1.77 | 600 | 6000 | 3395 | 5.66 | 25.7 | 43.1 |
| Test (3) 930 at 8 W for 4 min | 8.0 | 1.5 | 1.77 | 240 | 1920 | 1086 | 4.53 | 43.1 | 44.8 |
| Test (4) 870 at 5.5 W and 930 at 5.5 W for 10 min followed by | 11.0 | 1.5 | 1.77 | 600 | 6600 | 3735 | 6.22 | 22.9 | 45.2 |
| Test (4) 930 at 8 W for 4 min | 8.0 | 1.5 | 1.77 | 240 | 1920 | 1086 | 4.53 | 45.2 | 45.3 |
| Test (5) 870 at 5 W and 930 at 5 W for 8 min followed by | 10.0 | 1.5 | 1.77 | 480 | 4800 | 2716 | 5.66 | 24.2 | 43.2 |
| Test (5) 930 at 7 W for 4 min | 7.0 | 1.5 | 1.77 | 240 | 1680 | 951 | 3.96 | 43.2 | 43.8 |
| Test (6) 870 at 5.5 W and 930 at 5.5 W for 8 min followed by | 11.0 | 1.5 | 1.77 | 480 | 5280 | 2988 | 6.22 | 25.3 | 42.7 |
| Test (6) 930 at 7 W for 4 min | 7.0 | 1.5 | 1.77 | 240 | 1680 | 951 | 3.96 | 42.7 | 44.9 |
| Test (7) 870 at 5 W and 930 at 5 W for 6 min followed by | 10.0 | 1.5 | 1.77 | 360 | 3600 | 2037 | 5.66 | 26.2 | 40.6 |
| Test (7) 930 at 7 W for 4 min | 7.0 | 1.5 | 1.77 | 240 | 1680 | 951 | 3.96 | 40.6 | 44 |
| Test (8) 870 at 5.5 W and 930 at 5.5 W for 6 min followed by | 11.0 | 1.5 | 1.77 | 360 | 3960 | 2241 | 6.22 | 26 | 42 |
| Test (8) 930 at 7 W for 4 min | 7.0 | 1.5 | 1.77 | 240 | 1680 | 951 | 3.96 | 42 | 44.2 |

Experiment 1

Design

Eight different laser dosages were used to treat a saline-suspension of logarithmically growing MRSA, labeled A1 to H1.

The treated and a control untreated suspension were diluted and plated in triplicate on trypic soy agar with or without 30 μg/ml methicillin.

After 24 hrs of growth at 37° C. colonies were counted.

CFU (colony forming units) were compared between the plates with and without methicillin for both control (untreated) and treated MRSA.

Experiment 1

Results

Conditions D1 through H1 showed a similar reduction in CFU on the methicillin plates in treated and untreated samples.

Conditions A1, B1 and C1 showed 30%, 33%, or 67% fewer CFU in the laser treated samples compared to the untreated controls, respectively.

This indicates that the treatments performed on sample A1, B1 and C1 sensitized the MRSA to the effects of methicillin.

TABLE 23

MRSA Data Progression

| | | Methicillin (Meth) | | CFU | AVG | CFU/ml | Meth Effect | Laser Effect (+Meth) |
|---|---|---|---|---|---|---|---|---|
| A1 | Cont | no | 1 | 224 | 203.7 | 6.11E+08 | | |
| | | | 2 | 266 | | | | |
| | | | 3 | 121 | | | | |
| | | yes | 1 | 207 | 141.7 | 4.25E+08 | 0.695581 | |
| | | | 2 | 137 | | | | |
| | | | 3 | 81 | | | | |
| | Exp | no | 1 | 132 | 134.3 | 4.03E+08 | | |
| | | | 2 | 143 | | | | |
| | | | 3 | 128 | | | | |
| | | yes | 1 | 99 | 99.7 | 2.99E+08 | 0.741935 | 0.7035 |
| | | | 2 | 96 | | | | |
| | | | 3 | 104 | | | | |
| B1 | Cont | no | 1 | 235 | 188.3 | 5.65E+08 | | |
| | | | 2 | 220 | | | | |
| | | | 3 | 110 | | | | |
| | | yes | 1 | 166 | 169.3 | 5.08E+08 | 0.899115 | |
| | | | 2 | 192 | | | | |
| | | | 3 | 150 | | | | |
| | Exp | no | 1 | 213 | 200.3 | 6.01E+08 | | |
| | | | 2 | 199 | | | | |
| | | | 3 | 189 | | | | |
| | | yes | 1 | 102 | 113.3 | 3.40E+08 | 0.565724 | 0.6693 |
| | | | 2 | 107 | | | | |
| | | | 3 | 131 | | | | |
| C1 | Cont | no | 1 | 280 | 320.3 | 9.61E+08 | | |
| | | | 2 | 242 | | | | |
| | | | 3 | 439 | | | | |
| | | yes | 1 | 240 | 406 | 1.22E+09 | 1.26743 | |
| | | | 2 | 466 | | | | |
| | | | 3 | 512 | | | | |
| | Exp | no | 1 | 187 | 184 | 5.52E+08 | | |
| | | | 2 | 189 | | | | |
| | | | 3 | 176 | | | | |
| | | yes | 1 | 95 | 132.3 | 3.97E+08 | 0.719203 | 0.3259 |
| | | | 2 | 176 | | | | |
| | | | 3 | 126 | | | | |
| D1 | Cont | no | 1 | 251 | 184 | 5.52E+08 | | |
| | | | 2 | 125 | | | | |
| | | | 3 | 176 | | | | |
| | | yes | 1 | 171 | 154 | 4.62E+08 | 0.836957 | |
| | | | 2 | 141 | | | | |
| | | | 3 | 150 | | | | |
| | Exp | no | 1 | 221 | 203.7 | 6.11E+08 | | |
| | | | 2 | 180 | | | | |
| | | | 3 | 210 | | | | |
| | | yes | 1 | 164 | 155.3 | 4.66E+08 | 0.762684 | 1.0087 |
| | | | 2 | 153 | | | | |
| | | | 3 | 149 | | | | |
| E1 | Cont | no | 1 | 142 | 225.3 | 6.76E+08 | | |
| | | | 2 | 268 | | | | |
| | | | 3 | 266 | | | | |
| | | yes | 1 | 147 | 131.3 | 3.94E+08 | 0.58284 | |
| | | | 2 | 121 | | | | |
| | | | 3 | 126 | | | | |
| | Exp | no | 1 | 226 | 258.3 | 7.75E+08 | | |
| | | | 2 | 217 | | | | |
| | | | 3 | 332 | | | | |
| | | yes | 1 | 181 | 214.3 | 6.43E+08 | 0.829677 | 1.632 |
| | | | 2 | 232 | | | | |
| | | | 3 | 230 | | | | |
| F1 | Cont | no | 1 | 223 | 226.7 | 6.80E+08 | | |
| | | | 2 | 260 | | | | |
| | | | 3 | 197 | | | | |
| | | yes | 1 | 197 | 198 | 5.94E+08 | 0.873529 | |
| | | | 2 | 188 | | | | |
| | | | 3 | 209 | | | | |
| | Exp | no | 1 | 223 | 237.7 | 7.13E+08 | | |
| | | | 2 | 256 | | | | |
| | | | 3 | 234 | | | | |
| | | yes | 1 | 206 | 197 | 5.91E+08 | 0.828892 | 0.9949 |
| | | | 2 | 179 | | | | |
| | | | 3 | 206 | | | | |
| G1 | Cont | no | 1 | 214 | 224 | 6.72E+08 | | |
| | | | 2 | 217 | | | | |
| | | | 3 | 241 | | | | |
| | | yes | 1 | 246 | 219.3 | 6.58E+08 | 0.979167 | |
| | | | 2 | 222 | | | | |
| | | | 3 | 190 | | | | |
| | Exp | no | 1 | 243 | 242.7 | 7.28E+08 | | |
| | | | 2 | 261 | | | | |
| | | | 3 | 224 | | | | |
| | | yes | 1 | 193 | 210.7 | 6.32E+08 | 0.868132 | 0.9605 |
| | | | 2 | 237 | | | | |
| | | | 3 | 202 | | | | |
| H1 | Cont | no | 1 | 252 | 255.3 | 7.66E+08 | | |
| | | | 2 | 267 | | | | |
| | | | 3 | 247 | | | | |
| | | yes | 1 | 188 | 192.3 | 5.77E+08 | 0.753264 | |
| | | | 2 | 206 | | | | |
| | | | 3 | 183 | | | | |
| | Exp | no | 1 | 232 | 245 | 7.35E+08 | | |
| | | | 2 | 232 | | | | |
| | | | 3 | 271 | | | | |
| | | yes | 1 | 211 | 199.7 | 5.99E+08 | 0.814966 | 1.0381 |
| | | | 2 | 212 | | | | |
| | | | 3 | 176 | | | | |

TABLE 24

MRSA Dosimetry Progression
MRSA Dosimetry Progression
Nov. 07, 2006
First lasing procedure: Both 870 and 930
Second lasing procedure 930 alone

| Parameters | Output Power (W) | Beam Spot (cm) | Area of Spot (cm2) | Time (sec) | Total Energy Joules | Energy Density (J/cm$^2$) | Power Density (W/cm$^2$) | Temp Initial C. | Temp Final C. |
|---|---|---|---|---|---|---|---|---|---|
| Test (1) 870 at 5 W and 930 at 5 W for 12 min followed by | 10.0 | 1.5 | 1.77 | 720 | 7200 | 4074 | 5.66 | 23.4 | 45.3 |
| Test (1) 930 at 8 W for 6 min | 8.0 | 1.5 | 1.77 | 360 | 2880 | 1630 | 4.53 | 45.3 | 46.8 |
| Test (2) 870 at 5 W and 930 at 5 W for 12 min followed by | 10.0 | 1.5 | 1.77 | 720 | 7200 | 4074 | 5.66 | 21.2 | 45.5 |
| Test (2) 930 at 8 W for 6 min | 8.0 | 1.5 | 1.77 | 360 | 2880 | 1630 | 4.53 | 45.5 | 47.7 |
| Test (3) 870 at 5 W and 930 at 5 W for 12 min followed by | 10.0 | 1.5 | 1.77 | 720 | 7200 | 4074 | 5.66 | 21.6 | 47.0 |
| Test (3) 930 at 8 W for 6 min | 8.0 | 1.5 | 1.77 | 360 | 2880 | 1630 | 4.53 | 47.0 | 49.0 |
| Test (4) 870 at 5.5 W and 930 at 5.5 W for 12 min followed by | 11.0 | 1.5 | 1.77 | 720 | 7920 | 4482 | 6.22 | 20.4 | 50.3 |
| Test (4) 930 at 8 W for 6 min | 8.0 | 1.5 | 1.77 | 360 | 2880 | 1630 | 4.53 | 50.3 | 50.1 |
| Test (5) 870 at 5.5 W and 930 at 5.5 W for 12 min followed by | 11.0 | 1.5 | 1.77 | 720 | 7920 | 4482 | 6.22 | 24.0 | 50.9 |
| Test (5) 930 at 8 W for 6 min | 8.0 | 1.5 | 1.77 | 360 | 2880 | 1630 | 4.53 | 50.9 | 50.2 |
| Test (6) 870 at 5.5 W and 930 at 5.5 W for 12 min followed by | 11.0 | 1.5 | 1.77 | 720 | 7920 | 4482 | 6.22 | 23.0 | 48.2 |
| Test (6) 930 at 8 W for 6 min | 8.0 | 1.5 | 1.77 | 360 | 2880 | 1630 | 4.53 | 48.2 | 48.3 |
| Test (7) 870 at 5 W and 930 at 5 W for 14 min followed by | 10.0 | 1.5 | 1.77 | 840 | 8400 | 4753 | 5.66 | 22.0 | 48.3 |
| Test (7) 930 at 7 W for 8 min | 7.0 | 1.5 | 1.77 | 480 | 3360 | 1901 | 3.96 | 48.3 | 44.2 |
| Test (8) 870 at 5 W and 930 at 5 W for 14 min followed by | 11.0 | 1.5 | 1.77 | 840 | 9240 | 5229 | 6.22 | 22.0 | 47.6 |
| Test (8) 930 at 7 W for 8 min | 7.0 | 1.5 | 1.77 | 480 | 3360 | 1901 | 3.96 | 47.6 | 46.2 |

Experiment 2

Design

Eight different laser dosages based on an effective dose established in experiment 1 and previously were used to treat a saline-suspension of logarithmically growing MRSA, labeled A2 to H2.

The treated and a control untreated suspension were diluted and plated in triplicate on trypic soy agar with or without 30 µg/ml methicillin.

After 24 hrs of growth at 37° C. colonies were counted.

Experiment 2

Results

Comparison of CFU on plates with and without methicillin showed a significant increase in the effectiveness of methicillin in all laser treated samples with the exception of A2 and B2. This data is summarized in tabular form below.

TABLE 25

| Grouping | Fold increase in methicillin sensitivity |
|---|---|
| A2 | 0.84 |
| B2 | 0.91 |
| C2 | 3.20 |
| D2 | 2.44 |
| E2 | 4.33 |
| F2 | 2.13 |
| G2 | 3.47 |
| H2 | 1.62 |

TABLE 26

MRSA Data Progression

| | | Methicillin (Meth) | | CFU | AVG | CFU/ml | Meth Effect | Laser Effect (+Meth) |
|---|---|---|---|---|---|---|---|---|
| A2 | Cont | no | 1 | 51 | 49.3 | 1.48E+08 | | |
| | | | 2 | 43 | | | | |
| | | | 3 | 54 | | | | |
| | | yes | 1 | 35 | 35.7 | 1.07E+08 | 0.72 | |
| | | | 2 | 47 | | | | |
| | | | 3 | 25 | | | | |
| | Exp | no | 1 | 49 | 47 | 1.41E+08 | | |
| | | | 2 | 45 | | | | |
| | | | 3 | 47 | | | | |
| | | yes | 1 | 39 | 41 | 1.23E+08 | 0.87 | 1.15 |
| | | | 2 | 48 | | | | |
| | | | 3 | 36 | | | | |
| B2 | Cont | no | 1 | 97 | 71.3 | 2.14E+08 | | |
| | | | 2 | 47 | | | | |
| | | | 3 | 70 | | | | |
| | | yes | 1 | 47 | 49.7 | 1.49E+08 | 0.7 | |
| | | | 2 | 56 | | | | |
| | | | 3 | 46 | | | | |
| | Exp | no | 1 | 32 | 34.7 | 1.04E+08 | | |
| | | | 2 | 34 | | | | |
| | | | 3 | 38 | | | | |
| | | yes | 1 | 27 | 26.7 | 8.00E+07 | 0.77 | 0.54 |
| | | | 2 | 28 | | | | |
| | | | 3 | 25 | | | | |
| C2 | Cont | no | 1 | 60 | 55.7 | 1.67E+08 | | |
| | | | 2 | 65 | | | | |
| | | | 3 | 42 | | | | |
| | | yes | 1 | 42 | 55.3 | 1.66E+08 | 0.99 | |
| | | | 2 | 71 | | | | |
| | | | 3 | 53 | | | | |
| | Exp | no | 1 | 35 | 40.3 | 1.21E+08 | | |
| | | | 2 | 38 | | | | |
| | | | 3 | 48 | | | | |

TABLE 26-continued

MRSA Data Progression

| | Methicillin (Meth) | | CFU | AVG | CFU/ml | Meth Effect | Laser Effect (+Meth) |
|---|---|---|---|---|---|---|---|
| | yes | 1 | 16 | 12.7 | 3.80E+07 | 0.31 | 0.23 |
| | | 2 | 12 | | | | |
| | | 3 | 10 | | | | |
| D2 Cont | no | 1 | 108 | 85.3 | 2.56E+08 | | |
| | | 2 | 85 | | | | |
| | | 3 | 63 | | | | |
| | yes | 1 | 20 | 52 | 1.56E+08 | 0.61 | |
| | | 2 | 65 | | | | |
| | | 3 | 71 | | | | |
| Exp | no | 1 | 9 | 9.3 | 2.80E+07 | | |
| | | 2 | 9 | | | | |
| | | 3 | 10 | | | | |
| | yes | 1 | 5 | 2.3 | 7.00E+06 | 0.25 | 0.04 |
| | | 2 | 1 | | | | |
| | | 3 | 1 | | | | |
| E2 Cont | no | 1 | 52 | 59.7 | 1.79E+08 | | |
| | | 2 | 60 | | | | |
| | | 3 | 67 | | | | |
| | yes | 1 | 68 | 62.3 | 1.87E+08 | 1.04 | |
| | | 2 | 66 | | | | |
| | | 3 | 53 | | | | |
| Exp | no | 1 | 8 | 11 | 3.30E+07 | | |
| | | 2 | 12 | | | | |
| | | 3 | 13 | | | | |
| | yes | 1 | 2 | 2.7 | 8.00E+06 | 0.24 | 0.04 |
| | | 2 | 2 | | | | |
| | | 3 | 4 | | | | |
| F2 Cont | no | 1 | 125 | 87.7 | 2.63E+08 | | |
| | | 2 | 73 | | | | |
| | | 3 | 65 | | | | |
| | yes | 1 | 62 | 71 | 2.13E+08 | 0.81 | |
| | | 2 | 64 | | | | |
| | | 3 | 87 | | | | |
| Exp | no | 1 | 37 | 41 | 1.23E+08 | | |
| | | 2 | 43 | | | | |
| | | 3 | 43 | | | | |
| | yes | 1 | 13 | 15.7 | 4.70E+07 | 0.38 | 0.22 |
| | | 2 | 15 | | | | |
| | | 3 | 19 | | | | |
| G2 Cont | no | 1 | 77 | 80 | 2.40E+08 | | |
| | | 2 | 110 | | | | |
| | | 3 | 53 | | | | |
| | yes | 1 | 75 | 83.3 | 2.50E+08 | 1.04 | |
| | | 2 | 92 | | | | |
| | | 3 | 83 | | | | |
| Exp | no | 1 | 26 | 28 | 8.40E+07 | | |
| | | 2 | 28 | | | | |
| | | 3 | 30 | | | | |
| | yes | 1 | 10 | 8.3 | 2.50E+07 | 0.3 | 0.1 |
| | | 2 | 7 | | | | |
| | | 3 | 8 | | | | |
| H2 Cont | no | 1 | 77 | 105.7 | 3.17E+08 | | |
| | | 2 | 156 | | | | |
| | | 3 | 84 | | | | |
| | yes | 1 | 76 | 76.7 | 2.30E+08 | 0.73 | |
| | | 2 | 72 | | | | |
| | | 3 | 82 | | | | |
| Exp | no | 1 | 28 | 28.3 | 8.50E+07 | | |
| | | 2 | 36 | | | | |
| | | 3 | 21 | | | | |
| | yes | 1 | 13 | 12.7 | 3.80E+07 | 0.45 | 0.17 |
| | | 2 | 12 | | | | |
| | | 3 | 13 | | | | |

TABLE 27

Outlined Protocol for MRSA Study

| Time (hrs) | Task |
|---|---|
| T −18 | Inoculate overnight culture<br>50 ml directly from glycerol stock |
| T −4 | Set up starter cultures<br>Three dilutions 1:50, 1:125, 1:250<br>Monitor $OD_{600}$ of starter cultures |
| T 0 | Preparation of plating culture<br>At 10:00 am, the culture which is at $OD_{600} = 1.0$ is diluted 1:300 in PBS (50 mls final volume) and stored at RT for 1 hour.<br>(Room temp should be ~25° C.) |
| T +1 | Seeding of 24-well plates (8 plates in total)<br>2 ml aliquots are dispensed into pre-designated wells in 24-well plates and transferred to NOMIR (8 24-well plates total) |
| T +2 to +8 | Dilution of treated samples<br>After laser treatment, 100 μl from each well is diluted serially to a final dilution of 1:1000 in PBS.<br>Plating of treated samples<br>100 μl of final dilution is plated in quintuplicate (5X) on TSB agar with and without 30 μg/ml methicillin.<br>(10 TSB plates per well)<br>Plates are incubated at 37° C. 18-24 hrs. |
| T +24 | Colonies are counted on each plate (160 plates total) |

TABLE 28

MRSA Dosimetry Progression
MRSA Dosimetry Progression
Nov. 09, 2006
First lasing procedure: Both 870 and 930
Second lasing procedure 930 alone

| Parameters | Output Power (W) | Beam Spot (cm) | Area of Spot (cm2) | Time (sec) | Total Energy Joules | Energy Density (J/cm$^2$) | Power Density (W/cm$^2$) | Temp Initial C. | Temp Final C. |
|---|---|---|---|---|---|---|---|---|---|
| Test (1) 870 at 5.5 W and 930 at 5.5 W for 12 min followed by | 11.0 | 1.5 | 1.77 | 720 | 7920 | 4482 | 6.22 | 22.0 | 48.1 |
| Test (1) 930 at 8 W for 6 min | 8.0 | 1.5 | 1.77 | 360 | 2880 | 1630 | 4.53 | 48.1 | 47.7 |
| Test (2) 870 at 5.5 W and 930 at 5.5 W for 12 min followed by | 11.0 | 1.5 | 1.77 | 720 | 7920 | 4482 | 6.22 | 22.9 | 48.8 |
| Test (2) 930 at 8 W for 6 min | 8.0 | 1.5 | 1.77 | 360 | 2880 | 1630 | 4.53 | 48.8 | 48.7 |
| Test (3) 870 at 5.5 W and 930 at 5.5 W for 12 min followed by | 11.0 | 1.5 | 1.77 | 720 | 7920 | 4482 | 6.22 | 22.8 | 48.9 |

TABLE 28-continued

MRSA Dosimetry Progression
MRSA Dosimetry Progression
Nov. 09, 2006
First lasing procedure: Both 870 and 930
Second lasing procedure 930 alone

| Parameters | Output Power (W) | Beam Spot (cm) | Area of Spot (cm2) | Time (sec) | Total Energy Joules | Energy Density (J/cm$^2$) | Power Density (W/cm$^2$) | Temp Initial C. | Temp Final C. |
|---|---|---|---|---|---|---|---|---|---|
| Test (3) 930 at 8 W for 6 min | 8.0 | 1.5 | 1.77 | 360 | 2880 | 1630 | 4.53 | 48.9 | 48.9 |
| Test (4) 870 at 5.5 W and 930 at 5.5 W for 12 min followed by | 11.0 | 1.5 | 1.77 | 720 | 7920 | 4482 | 6.22 | 24.0 | 50.3 |
| Test (4) 930 at 8 W for 6 min | 8.0 | 1.5 | 1.77 | 360 | 2880 | 1630 | 4.53 | 50.3 | 50.5 |
| Test (5) 870 at 5 W and 930 at 5 W for 14 min followed by | 10.0 | 1.5 | 1.77 | 840 | 8400 | 4753 | 5.66 | 23.7 | 48.4 |
| Test (5) 930 at 6 W for 9 min | 6.0 | 1.5 | 1.77 | 540 | 3240 | 1833 | 3.40 | 48.4 | 45.0 |
| Test (6) 870 at 5 W and 930 at 5 W for 14 min followed by | 10.0 | 1.5 | 1.77 | 840 | 8400 | 4753 | 5.66 | 23.5 | 49.2 |
| Test (6) 930 at 6 W for 9 min | 6.0 | 1.5 | 1.77 | 540 | 3240 | 1833 | 3.40 | 42.9 | 46.3 |
| Test (7) 870 at 5 W and 930 at 5 W for 14 min followed by | 10.0 | 1.5 | 1.77 | 840 | 8400 | 4753 | 5.66 | 25.6 | 49.9 |
| Test (7) 930 at 6 W for 9 min | 6.0 | 1.5 | 1.77 | 540 | 3240 | 1833 | 3.40 | 49.9 | 46.3 |
| Test (8) 870 at 5 W and 930 at 5 W for 14 min followed by | 10.0 | 1.5 | 1.77 | 840 | 8400 | 4753 | 5.66 | 22.1 | 48.0 |
| Test (8) 930 at 6 W for 9 min | 6.0 | 1.5 | 1.77 | 540 | 3240 | 1833 | 3.40 | 48.0 | 46.0 |

Experiment 3

Design

Eight different laser dosages based on an effective dose established in experiments 1 and 2 and previously were used to treat a saline-suspension of logarithmically growing MRSA, labeled A3 to H3.

The treated and a control untreated suspension were diluted and plated in pentuplicate on trypic soy agar with or without 30 µg/ml methicillin. After 24 hrs of growth at 37° C. colonies were counted.

Experiment 3

Results

Comparison of CFU on plates with and without methicillin showed a significant increase in the effectiveness of methicillin in all laser treated samples. This data is summarized in tabular form below.

TABLE 29

| Grouping | Fold increase in methicillin sensitivity |
|---|---|
| A3 | 1.98 |
| B3 | 1.62 |
| C3 | 1.91 |
| D3 | 2.59 |
| E3 | 2.09 |
| F3 | 2.08 |
| G3 | 3.16 |
| H3 | 2.97 |

TABLE 30

MRSA Data Progression

| | | Methicillin (Meth) | | CFU | AVG | CFU/ml | Meth Effect | Laser Effect (+M) |
|---|---|---|---|---|---|---|---|---|
| A3 | Cont | no | 1 | 41 | 47 | 1.41E+08 | | |
| | | | 2 | 63 | | | | |
| | | | 3 | 46 | | | | |
| | | | 4 | 49 | | | | |
| | | | 5 | 36 | | | | |
| | | yes | 1 | 35 | 48.4 | 1.45E+08 | 1.03 | |
| | | | 2 | 45 | | | | |
| | | | 3 | 52 | | | | |
| | | | 4 | 66 | | | | |
| | | | 5 | 44 | | | | |
| | Exp | no | 1 | 24 | 31.4 | 9.42E+07 | | |
| | | | 2 | 34 | | | | |
| | | | 3 | 26 | | | | |
| | | | 4 | 33 | | | | |
| | | | 5 | 40 | | | | |
| | | yes | 1 | 23 | 16.2 | 4.86E+07 | 0.52 | 0.33 |
| | | | 2 | 15 | | | | |
| | | | 3 | 14 | | | | |
| | | | 4 | 16 | | | | |
| | | | 5 | 13 | | | | |
| B3 | Cont | no | 1 | 109 | 72 | 2.16E+08 | | |
| | | | 2 | 61 | | | | |
| | | | 3 | 59 | | | | |
| | | | 4 | 61 | | | | |
| | | | 5 | 70 | | | | |
| | | yes | 1 | 61 | 71.4 | 2.14E+08 | 0.99 | |
| | | | 2 | 79 | | | | |
| | | | 3 | 51 | | | | |
| | | | 4 | 68 | | | | |
| | | | 5 | 98 | | | | |
| | Exp | no | 1 | 27 | 31.2 | 9.36E+07 | | |
| | | | 2 | 25 | | | | |
| | | | 3 | 39 | | | | |
| | | | 4 | 24 | | | | |
| | | | 5 | 41 | | | | |
| | | yes | 1 | 9 | 19 | 5.70E+07 | 0.61 | 0.27 |
| | | | 2 | 22 | | | | |
| | | | 3 | 23 | | | | |
| | | | 4 | 25 | | | | |
| | | | 5 | 16 | | | | |

TABLE 30-continued

MRSA Data Progression

| | | Methicillin (Meth) | | CFU | AVG | CFU/ml | Meth Effect | Laser Effect (+M) |
|---|---|---|---|---|---|---|---|---|
| C3 | Cont | no | 1 | 46 | 57.6 | 1.73E+08 | | |
| | | | 2 | 60 | | | | |
| | | | 3 | 60 | | | | |
| | | | 4 | 66 | | | | |
| | | | 5 | 56 | | | | |
| | | yes | 1 | 70 | 58.4 | 1.75E+08 | 1.01 | |
| | | | 2 | 54 | | | | |
| | | | 3 | 52 | | | | |
| | | | 4 | 51 | | | | |
| | | | 5 | 65 | | | | |
| | Exp | no | 1 | 52 | 38.2 | 1.15E+08 | | |
| | | | 2 | 34 | | | | |
| | | | 3 | 38 | | | | |
| | | | 4 | 34 | | | | |
| | | | 5 | 33 | | | | |
| | | yes | 1 | 12 | 20.2 | 6.06E+07 | 0.53 | 0.35 |
| | | | 2 | 26 | | | | |
| | | | 3 | 22 | | | | |
| | | | 4 | 24 | | | | |
| | | | 5 | 17 | | | | |
| D3 | Cont | no | 1 | 50 | 50.6 | 1.52E+08 | | |
| | | | 2 | 45 | | | | |
| | | | 3 | 55 | | | | |
| | | | 4 | 54 | | | | |
| | | | 5 | 49 | | | | |
| | | yes | 1 | 58 | 51.2 | 1.54E+08 | 1.01 | |
| | | | 2 | 46 | | | | |
| | | | 3 | 43 | | | | |
| | | | 4 | 59 | | | | |
| | | | 5 | 50 | | | | |
| | Exp | no | 1 | 7 | 9.2 | 2.76E+07 | | |
| | | | 2 | 10 | | | | |
| | | | 3 | 8 | | | | |
| | | | 4 | 9 | | | | |
| | | | 5 | 12 | | | | |
| | | yes | 1 | 6 | 3.6 | 1.08E+07 | 0.39 | 0.07 |
| | | | 2 | 3 | | | | |
| | | | 3 | 1 | | | | |
| | | | 4 | 5 | | | | |
| | | | 5 | 3 | | | | |
| E3 | Cont | no | 1 | 47 | 54.8 | 1.64E+08 | | |
| | | | 2 | 55 | | | | |
| | | | 3 | 71 | | | | |
| | | | 4 | 45 | | | | |
| | | | 5 | 56 | | | | |
| | | yes | 1 | 56 | 50.6 | 1.52E+08 | 0.92 | |
| | | | 2 | 48 | | | | |
| | | | 3 | 48 | | | | |
| | | | 4 | 52 | | | | |
| | | | 5 | 49 | | | | |
| | Exp | no | 1 | 50 | 53.2 | 1.60E+08 | | |
| | | | 2 | 65 | | | | |
| | | | 3 | 49 | | | | |
| | | | 4 | 46 | | | | |
| | | | 5 | 56 | | | | |
| | | yes | 1 | 15 | 23.6 | 7.08E+07 | 0.44 | 0.47 |
| | | | 2 | 24 | | | | |
| | | | 3 | 26 | | | | |
| | | | 4 | 27 | | | | |
| | | | 5 | 26 | | | | |
| F3 | Cont | no | 1 | 57 | 72.4 | 2.17E+08 | | |
| | | | 2 | 142 | | | | |
| | | | 3 | 62 | | | | |
| | | | 4 | 52 | | | | |
| | | | 5 | 49 | | | | |
| | | yes | 1 | 65 | 53.2 | 1.60E+08 | 0.73 | |
| | | | 2 | 50 | | | | |
| | | | 3 | 54 | | | | |
| | | | 4 | 40 | | | | |
| | | | 5 | 57 | | | | |
| | Exp | no | 1 | 29 | 28.4 | 8.52E+07 | | |
| | | | 2 | 39 | | | | |
| | | | 3 | 25 | | | | |
| | | | 4 | 23 | | | | |
| | | | 5 | 26 | | | | |
| | | yes | 1 | 13 | 9.8 | 2.94E+07 | 0.35 | 0.18 |
| | | | 2 | 10 | | | | |
| | | | 3 | 14 | | | | |
| | | | 4 | 5 | | | | |
| | | | 5 | 7 | | | | |
| G3 | Cont | no | 1 | 60 | 57.8 | 1.73E+08 | | |
| | | | 2 | 53 | | | | |
| | | | 3 | 54 | | | | |
| | | | 4 | 66 | | | | |
| | | | 5 | 56 | | | | |
| | | yes | 1 | 56 | 67.6 | 2.03E+08 | 1.17 | |
| | | | 2 | 56 | | | | |
| | | | 3 | 70 | | | | |
| | | | 4 | 63 | | | | |
| | | | 5 | 93 | | | | |
| | Exp | no | 1 | 23 | 22.8 | 6.84E+07 | | |
| | | | 2 | 24 | | | | |
| | | | 3 | 21 | | | | |
| | | | 4 | 21 | | | | |
| | | | 5 | 25 | | | | |
| | | yes | 1 | 9 | 8.4 | 2.52E+07 | 0.37 | 0.12 |
| | | | 2 | 11 | | | | |
| | | | 3 | 5 | | | | |
| | | | 4 | 8 | | | | |
| | | | 5 | 9 | | | | |
| H3 | Cont | no | 1 | 64 | 72.4 | 2.17E+08 | | |
| | | | 2 | 86 | | | | |
| | | | 3 | 72 | | | | |
| | | | 4 | 45 | | | | |
| | | | 5 | 95 | | | | |
| | | yes | 1 | 72 | 75.2 | 2.26E+08 | 1.04 | |
| | | | 2 | 75 | | | | |
| | | | 3 | 71 | | | | |
| | | | 4 | 79 | | | | |
| | | | 5 | 79 | | | | |
| | Exp | no | 1 | 20 | 23.8 | 7.14E+07 | | |
| | | | 2 | 17 | | | | |
| | | | 3 | 23 | | | | |
| | | | 4 | 28 | | | | |
| | | | 5 | 31 | | | | |
| | | yes | 1 | 6 | 8.4 | 2.52E+07 | 0.35 | 0.11 |
| | | | 2 | 12 | | | | |
| | | | 3 | 4 | | | | |
| | | | 4 | 9 | | | | |
| | | | 5 | 11 | | | | |

TABLE 31

Outlined Protocol

| Time (hrs) | Task |
|---|---|
| T −18 | Inoculate overnight culture |
| | 50 ml directly from glycerol stock |
| T −4 | Set up starter cultures |
| | Three dilutions 1:50, 1:125, 1:250 |
| | Monitor $OD_{600}$ of starter cultures |
| T 0 | Preparation of plating culture |
| | At 10:00 am, the culture which is at $OD_{600}$ = 1.0 is diluted 1:300 in PBS (50 mls final volume) and stored at RT for 1 hour. |
| | (Room temp should be ~25° C.) |
| T +1 | Seeding of 24-well plates (6 plates in total) |
| | 2 ml aliquots are dispensed into pre-designated wells in 24-well plates and transferred to NOMIR (6 24-well plates total) |

TABLE 31-continued

Outlined Protocol

| Time (hrs) | Task |
|---|---|
| T +2 to +8 | Dilution of treated samples<br>After laser treatment, 100 μl from each well is diluted serially to a final dilution of 1:1000 in PBS.<br>Plating of treated samples<br>100 μl of final dilution is plated in Quintuplicate (5X) on TSB agar in the following manner:<br>24 well Plate # 1 and 2 with and without 30 μg/ml methicillin.<br>24 well Plate # 3 and 4 with and without μg/ml Penicillin<br>24 well Plate # 5 and 6 with and without μg/ml Erythromycin<br>(10 TSB plates per well)<br>Plates are incubated at 37° C. 18-24 hrs. |
| T +24 | Colonies are counted on each plate (120 plates total) |

TABLE 32

MRSA Dosimetry Progression
MRSA Dosimetry Progression
First lasing procedure: Both 870 and 930
Second lasing procedure 930 alone

| Parameters | Output Power (W) | Beam Spot (cm) | Area of Spot (cm2) | Time (sec) | Total Energy Joules | Energy Density (J/cm$^2$) | Power Density (W/cm$^2$) | Temp Initial C. | Temp Final C. |
|---|---|---|---|---|---|---|---|---|---|
| Test (1) 870 at 5.5 W and 930 at 5.5 W for 12 min followed by | 11.0 | 1.5 | 1.77 | 720 | 7920 | 4482 | 6.22 | 22.3 | 46.3 |
| Test (1) 930 at 8 W for 6 min (METHICILLIN PLATES) | 8.0 | 1.5 | 1.77 | 360 | 2880 | 1630 | 4.53 | 46.3 | 47.6 |
| Test (2) 870 at 5 W and 930 at 5 W for 14 min followed by | 10.0 | 1.5 | 1.77 | 840 | 8400 | 4753 | 5.66 | 23.1 | 47.1 |
| Test (2) 930 at 6 W for 9 min (METHICILLIN PLATES) | 6.0 | 1.5 | 1.77 | 540 | 3240 | 1833 | 3.40 | 47.1 | 44.3 |
| Test (3) 870 at 5.5 W and 930 at 5.5 W for 12 min followed by | 11.0 | 1.5 | 1.77 | 720 | 7920 | 4482 | 6.22 | 24.4 | 48.4 |
| Test (3) 930 at 8 W for 6 min (PENICILLIN G PLATES) | 8.0 | 1.5 | 1.77 | 360 | 2880 | 1630 | 4.53 | 48.4 | 47.1 |
| Test (4) 870 at 5 W and 930 at 5 W for 14 min followed by | 10.0 | 1.5 | 1.77 | 840 | 8400 | 4753 | 5.66 | 23.3 | 47.9 |
| Test (4) 930 at 6 W for 9 min (PENICILLIN G PLATES) | 6.0 | 1.5 | 1.77 | 540 | 3240 | 1833 | 3.40 | 47.9 | 45.0 |
| Test (5) 870 at 5.5 W and 930 at 5.5 W for 12 min followed by | 11.0 | 1.5 | 1.77 | 720 | 7920 | 4482 | 6.22 | 22.9 | 50.2 |
| Test (5) 930 at 8 W for 6 min (ERYTHROMYCIN PLATES) | 8.0 | 1.5 | 1.77 | 360 | 2880 | 1630 | 4.53 | 50.2 | 51.6 |
| Test (6) 870 at 5 W and 930 at 5 W for 14 min followed by | 10.0 | 1.5 | 1.77 | 840 | 8400 | 4753 | 5.66 | 24.2 | 50.3 |
| Test (6) 930 at 6 W for 9 min (ERYTHROMYCIN PLATES) | 6.0 | 1.5 | 1.77 | 540 | 3240 | 1833 | 3.40 | 50.3 | 43.6 |

Independent Report for MRSA Studies

Experiment 4

Design

Two different laser dosages based on an effective dose established in previous experiments were used to treat a saline-suspension of logarithmically growing MRSA, labeled A4 to F4.

The treated and a control untreated suspension were diluted and plated in pentuplicate on trypic soy agar with or without 30 μg/ml methicillin (Groups A4 and B4), 0.5 μg/ml penicillin G (Groups C4 and D4) or 4 μg/ml erythromycin (Groups E4 and F4).

After 24 hrs of growth at 37° C. colonies were counted.

Experiment 4
Results

Laser treatment increases sensitivity of MRSA to each antibiotic tested by several fold. This data is summarized below.

TABLE 33

| Series | Drug |
|---|---|
| A4 | Methicillin |
| B4 | Methicillin |
| C4 | Penicillin |

TABLE 33-continued

| Series | Drug |
|---|---|
| D4 | Penicillin |
| E4 | Erythromycin |
| F4 | Erythromycin |

TABLE 34

| Grouping | Fold increase in antibiotic sensitivity |
|---|---|
| A4 | 2.19 |
| B4 | 2.63 |
| C4 | 2.21 |
| D4 | 3.45 |

TABLE 34-continued

| Grouping | Fold increase in antibiotic sensitivity |
|---|---|
| E4 | 50.50 |
| F4 | 9.67 |

TABLE 35

MRSA Data Progression

| | Drug? | | CFU | AVG | CFU/ml | Drug Effect | Laser Effect (+Drug) |
|---|---|---|---|---|---|---|---|
| A4 Cont | no | 1 | 84 | 92 | 2.76E+08 | | |
| | | 2 | 95 | | | | |
| | | 3 | 69 | | | | |
| | | 4 | 106 | | | | |
| | | 5 | 106 | | | | |
| | yes | 1 | 97 | 86.2 | 2.59E+08 | 0.94 | |
| | | 2 | 104 | | | | |
| | | 3 | 82 | | | | |
| | | 4 | 58 | | | | |
| | | 5 | 90 | | | | |
| Exp | no | 1 | 82 | 84.4 | 2.53E+08 | | |
| | | 2 | 80 | | | | |
| | | 3 | 85 | | | | |
| | | 4 | 90 | | | | |
| | | 5 | 85 | | | | |
| | yes | 1 | 37 | 36.2 | 1.09E+08 | 0.43 | 0.42 |
| | | 2 | 33 | | | | |
| | | 3 | 36 | | | | |
| | | 4 | 39 | | | | |
| | | 5 | 36 | | | | |
| B4 Cont | no | 1 | 86 | 105 | 3.15E+08 | | |
| | | 2 | 142 | | | | |
| | | 3 | 105 | | | | |
| | | 4 | 97 | | | | |
| | | 5 | 95 | | | | |
| | yes | 1 | 149 | 132.6 | 3.98E+08 | 1.26 | |
| | | 2 | 101 | | | | |
| | | 3 | 119 | | | | |
| | | 4 | 153 | | | | |
| | | 5 | 141 | | | | |
| Exp | no | 1 | 73 | 88.8 | 2.66E+08 | | |
| | | 2 | 84 | | | | |
| | | 3 | 109 | | | | |
| | | 4 | 89 | | | | |
| | | 5 | 89 | | | | |
| | yes | 1 | 46 | 42.4 | 1.27E+08 | 0.48 | 0.32 |
| | | 2 | 34 | | | | |
| | | 3 | 42 | | | | |
| | | 4 | 44 | | | | |
| | | 5 | 46 | | | | |
| C4 Cont | no | 1 | 211 | 143.8 | 4.31E+08 | | |
| | | 2 | 138 | | | | |
| | | 3 | 114 | | | | |
| | | 4 | 145 | | | | |
| | | 5 | 111 | | | | |
| | yes | 1 | 106 | 108.4 | 3.25E+08 | 0.75 | |
| | | 2 | 99 | | | | |
| | | 3 | 102 | | | | |
| | | 4 | 113 | | | | |
| | | 5 | 122 | | | | |
| Exp | no | 1 | 84 | 90.2 | 2.71E+08 | | |
| | | 2 | 84 | | | | |
| | | 3 | 87 | | | | |
| | | 4 | 107 | | | | |
| | | 5 | 89 | | | | |
| | yes | 1 | 25 | 30.4 | 9.12E+07 | 0.34 | 0.28 |
| | | 2 | 33 | | | | |
| | | 3 | 19 | | | | |
| | | 4 | 33 | | | | |
| | | 5 | 42 | | | | |
| D4 Cont | no | 1 | 111 | 123.6 | 3.71E+08 | | |
| | | 2 | 110 | | | | |
| | | 3 | 135 | | | | |
| | | 4 | 107 | | | | |
| | | 5 | 155 | | | | |
| | yes | 1 | 101 | 132.8 | 3.98E+08 | 1.07 | |
| | | 2 | 111 | | | | |
| | | 3 | 138 | | | | |
| | | 4 | 132 | | | | |
| | | 5 | 182 | | | | |
| Exp | no | 1 | 73 | 75.6 | 2.27E+08 | | |
| | | 2 | 86 | | | | |
| | | 3 | 93 | | | | |
| | | 4 | 74 | | | | |
| | | 5 | 52 | | | | |
| | yes | 1 | 14 | 23.8 | 7.14E+07 | 0.31 | 0.18 |
| | | 2 | 23 | | | | |
| | | 3 | 22 | | | | |
| | | 4 | 29 | | | | |
| | | 5 | 31 | | | | |
| E4 Cont | no | 1 | 122 | 125.6 | 3.77E+08 | | |
| | | 2 | 154 | | | | |
| | | 3 | 127 | | | | |
| | | 4 | 116 | | | | |
| | | 5 | 109 | | | | |
| | yes | 1 | 199 | 127 | 3.81E+08 | 1.01 | |
| | | 2 | 125 | | | | |
| | | 3 | 103 | | | | |
| | | 4 | 101 | | | | |
| | | 5 | 107 | | | | |
| Exp | no | 1 | 17 | 17.6 | 5.28E+07 | | |
| | | 2 | 20 | | | | |
| | | 3 | 18 | | | | |
| | | 4 | 21 | | | | |
| | | 5 | 12 | | | | |
| | yes | 1 | 0 | 0.4 | 1.20E+06 | 0.02 | 0 |
| | | 2 | 1 | | | | |
| | | 3 | 0 | | | | |
| | | 4 | 0 | | | | |
| | | 5 | 1 | | | | |
| F4 Cont | no | 1 | 117 | 177.8 | 5.33E+08 | | |
| | | 2 | 126 | | | | |
| | | 3 | 318 | | | | |
| | | 4 | 166 | | | | |
| | | 5 | 162 | | | | |
| | yes | 1 | 186 | 155.4 | 4.66E+08 | 0.87 | |
| | | 2 | 170 | | | | |
| | | 3 | 121 | | | | |
| | | 4 | 132 | | | | |
| | | 5 | 168 | | | | |
| Exp | no | 1 | 60 | 66.4 | 1.99E+08 | | |
| | | 2 | 54 | | | | |
| | | 3 | 60 | | | | |
| | | 4 | 102 | | | | |
| | | 5 | 56 | | | | |
| | yes | 1 | 2 | 5.8 | 1.74E+07 | 0.09 | 0.04 |
| | | 2 | 7 | | | | |
| | | 3 | 6 | | | | |
| | | 4 | 6 | | | | |
| | | 5 | 8 | | | | |

Example XX

Non-Thermal NIMELS Interaction

Evidence for Non-Thermal NIMELS Interaction:

It was demonstrated through experimentation (in vitro water bath studies), that the temperatures reached in the in vitro NIMELS experimentation, were not high enough in and of themselves to neutralize the pathogens.

In the chart that follows, it can clearly be seen that when simple *E. coli* Bacteria were challenged at 47.5 C continuously for 8 minutes in a test tube in a water bath, they achieved 91% growth of colonies. Therefore, it was demonstrated essentially that the NIMELS reaction is indeed photo-chemical in nature, and occurs in the absence of exogenous drugs and/or dyes.

TABLE 36

Water Bath Test
Bacteria placed in PBS on bench at room
temperature for 3 hours; then in water
bath at 47.5 C. for 8 min and plated.

|   | Control<br>Aug. 26, 2005 |   | Final<br>Aug. 26, 2005 |
|---|---|---|---|
| A | 73 | D | 64 |
| B | 82 | E | 73 |
| C | 75 | F | 72 |
| | Average %<br>Growth | | 90.9%<br>Lived | after 47.5 C. for 8 min.

Example XXI

Laser Treatment for Microbial Reduction and Elimination of Nasal Colonization of MRSA The Nomir Near Infrared Microbial Elimination Laser System (NOVEON™ Model 1120 dual-wavelength diode laser was employed for this study. The laser operates in continuous wave format at two wavelengths, 870 nm (+/−5 nm n) and 930 nm (+/−5 nm). This device is a class II non-significant risk laser device. The laser sources of this device are semiconductor laser arrays that are optically coupled to form a single fiber laser output. The delivery system consists of a single flexible optical fiber. The device delivers continuous wave laser light only.

The device is designed specifically to effect microbial cell optical destruction, while preserving and without substantial damage optically or thermally to the human tissue at the infection site being irradiated. In that regard, the NOVEON™ system was designed to harness the known photo-lethal characteristics of these precise energies to kill pathogenic microorganism at far lower energy levels and heat deposition than is generally necessary to kill pathogens using laser-based thermal sterilization means.

Using exposure to the dual wavelength infrared NOVEON™ laser, at temperature levels inherently not lethal to the organism, we had accomplished in vitro successful reversal of MRSA resistance to Methicillin, Penicillin, Erythromycin and Tetracycline. It has also been shown in vitro, that MRSA that has been exposed to a sublethal dose by the NOVEON™ laser will become sensitive to antibiotics to which it was previously resistant.

Currently, topical intra-nasal antimicrobial agents are recognized as the preferred method for preventing (distal-site) infections because of their demonstrated effectiveness and widespread desire to minimize the use of systemic antimicrobials.

Thus, the design of this protocol includes a number of important factors have been considered. Foremost is the need to assure that the amount of energy used in the Nares is safe for the nasal and nares tissues. Furthermore, significant human and histological tests have been done with the Noveon laser in the areas that the study is treating Human Studies Initial studies were performed to chart and ensure the thermal safety of laser energies on human dermal tissues. Exposure of dermal surfaces to both 870 nm and 930 nm simultaneously with a combined Power Density of 1.70 W/cm$^2$ for up to 233 seconds, results in a skin surface temperature of 100° F. as measured with a laser infrared thermometer. Exposure of dermal surfaces to 930 nm alone at a Power Density of 1.70 W/cm$^2$ for up to 142 seconds, results in a skin surface temperature of 97° F. At or above these doses to dermal infection sites, pain can result. It is therefore desirable from a standpoint of patient comfort not to exceed these doses.

TABLE 37

Dosimetry Simultaneously Using 870 and 930 Nanometers

| Parameters | Output<br>Power<br>(W) | Beam<br>Spot<br>(cm) | Area<br>of<br>Spot<br>(cm2) | Time<br>(sec) | Total<br>Energy<br>Joules | Energy<br>Density<br>(J/cm2) | Power<br>Density<br>(W/<br>cm2) |
|---|---|---|---|---|---|---|---|
| 870 nm | 1.5 | 1.5 | 1.77* | 250 | 375 | 212 | 0.85 |
| 930 nm | 1.5 | 1.5 | 1.77* | 250 | 375 | 212 | 0.85 |
| Combined | 3.0 | 1.5 | 1.77* | 250 | 750 | 424 | 1.70 |

TABLE 38

Dosimetry at 930 Nanometers

| Parameters | Output<br>Power<br>(W) | Beam<br>Spot<br>(cm) | Area<br>of<br>Spot<br>(cm2) | Time<br>(sec) | Total<br>Energy<br>Joules | Energy<br>Density<br>(J/cm2) | Power<br>Density<br>(W/<br>cm2) |
|---|---|---|---|---|---|---|---|
| 930 nm | 3.0 | 1.5 | 1.77* | 120 | 360 | 204 | 1.70 |

Additional testing of the device on the epithelial tissue of humans was conducted using a specially prepared dispersion tip designed to be inserted in the nares. Using a dispersion tip, laser energy was delivered to the nostrils circumferentially by an optical fiber (connected to the NOVEON™ laser) that terminates in a central diffusing tip. This was placed within the inner lumen of the nostril (nares).

A cylindrical diffusing optical fiber tip for near infrared light delivery was fabricated specifically for uniform illumination of a length of 1.5 cm, to then be placed in a transparent catheter (of given width) to prevent placement too far anteriorly in the nostril, and guarantee a uniform power density at all tissues proximal to the catheter within the nostril.

The tip included an optically transmissive, light diffusing, fiber tip assembly having an entrance aperture through a proximal reflector, a radiation-scattering, transmissive material (e.g. a poly-tetrafluoroethylene tube) surrounding an enclosed cavity (e.g. a cylindrical void filled with air or another substantially non-scattering, transparent medium), and a distal reflective surface. As radiation propagates through the fiber tip assembly, a portion of the radiation is scattered in a cylindrical (or partly cylindrical) pattern along the distal portion of the fiber tip. Radiation, which is not scattered during this initial pass through the tip, is reflected by at least one surface of the assembly and returned through the tip. During this second pass, the remaining radiation, (or a portion of the returning radiation), is scattered and emitted from the proximal portion of the tube. Multiple additional reflections off of the proximal and distal reflectors provide further homogenization of the intensity profile. Preferably the scattering medium has a prescribed inner diameter. This inner diameter of the scattering material is designed such that the interaction with this material and the multiple reflections off of the cavity reflectors interact to provide a substantially proscribed axial distribution of laser radiation over the length of the tip apparatus. Suitable choices of tip dimensions provide control over the emitted axial and azimuthal energy distributions.

To first document safety with the instrumentation, samples of turkey muscle (shown to be a suitable model for nasal mucosa, were irradiated with the above described dispersion tip. The maximum temperature attained during this experiment was 33.9 degrees Centigrade. Further, no specimen showed any burning or necrosis, despite use of exposure times that were double than any anticipated for use in human subjects.

TABLE 39

Dosimetry Simultaneously Using 870 and 930 Nanometers

| Parameters | Output Power (W) | Time (sec) | Total Energy Joules | Energy Density (J/cm2) | Power Density (W/cm2) |
|---|---|---|---|---|---|
| 870 nm | 0.5 | 180 | 90 | | |
| 930 nm | 1.5 | 180 | 180 | | |
| Combined | 1.5 | 180 | 270 | 45 | .25 |

TABLE 40

Dosimetry at 930 Nanometers

| Parameters | Output Power (W) | Time (sec) | Total Energy Joules | Energy Density (J/cm2) | Power Density (W/cm2) |
|---|---|---|---|---|---|
| 930 nm | 1.5 | 180 | 270 | 45 | .25 |

Studies have shown that there are five factors to consider regarding energy absorption and heat generation by the "y" emissions of near infrared diode lasers. These factors are: wavelength and optical penetration depth of the laser; absorption characteristics of exposed tissue; temporal mode (pulsed or continuous; exposure time; and power density of the laser beam.

Diode lasers in the near infrared range have a very low absorption coefficient in water; hence, they achieve relatively deep optical penetration in tissues that contain 80% water (such as the dermis, the oral mucosa, bone and the gingiva. With conventional near infrared diode soft tissue lasers, the depth of penetration (before photon absorption) of the greatest amount of the incident energy is about 1.5 cm. This allows the near infrared laser energy to pass through water with minimal absorption, producing thermal effects deeper in the tissue and the photons are absorbed by the deeper tissue pigments. This photobiology allows for controlled, deeper soft-tissue irradiation and decontamination, as the photons that emerge from the dispersion tip in a uniform dosimetry from the diffusing tip absorbed by blood and other tissue pigments.

Approached from other known dosimetry perspectives, if the conventional Power Equation is applied to in vivo NIMELS dosimetries [Power (Watts)=Work/Time], the following examples illustrate the Power differences between current therapies: Photoablative dosimetry=1000 $J/cm^2$ in $1/1,000^{th}$ of a second; Thermal vaporizing dosimetry=1000 $J/cm^2$ in 1 second; and NIMELS decontamination dosimetry=500 $J/cm^2$ in 360 seconds.

This investigational protocol was designed to demonstrate that the Noveon Laser treatment is able to produce reduction in Nasal carriage of MRSA in patients with previously "culture positive" history. This investigational protocol was an open-label study of subjects who are colonized with MRSA in the nares (nostril). The study was done in two parts.

Part One

Subjects

In this human study, three arms were produced. Subjects with a previous "culture positive" history who were found to be positive for MRSA colonization in the nares were randomized to one of three treatment groups: Arm #1: ⅓ of the subjects were treated with laser alone; Arm #2: ⅓ of the subjects were be treated with topical $H_2O_2$ and then the laser after two minutes. This was done on day 1 and again on day three; and Arm #3: ⅓ of the subjects were treated with the laser and then a topical antibiotic three times a day for five days. Prior to enrollment in this study, prospective subjects met all of the following criteria: age≥18 years and ≤70 years of age; previous positive MRSA culture; negative urine pregnancy test or post-menopausal for one year; willing to comply with study requirements, including return visits and self-application of topical antibiotics; and willing to provide informed consent to participate. Prospective subjects were excluded from this study if any of the following criteria were met: pregnancy; patients who are severely immunocompromised (such as may occur in AIDS, renal transplant regimens, immunosuppressed states consequent to malignancy or agents used in rendering oncologic care, or who suffer from end stage renal disease); diabetic patients; allergy to antimicrobials being used in the study (group 3). The exclusion of such groups in this instance was solely for purposes of performing a controlled clinical study, and it is particularly noted that the above exclusion groups are actually considered good candidates for the phototherapeutic treatments described herein, wherein such patients would actually benefit from therapeutic bacterial photodamage in that reduced systemic doses of antibiotics could be given and infection sites could be better cleared.

Study Procedures:

All participants underwent an initial quantitative assessment for nasal carriage of S. aureus, during their first visit. Each participant had the anterior nares (each nostril) sampled for culture with a circular movement (three rotations on each side) of a sterile wood applicator plain Rayon® tipped swab in each nostril and placed in a labeled tube. 2 ml of room temp phosphate buffered saline was placed in the tube after the removal of the swab (to completely cover the swab in the tube). Each swab was then placed back in the tube and the tube was then vortexed for 15 seconds to disperse isolates of MRSA and/or MSSA into the PBS solution. Aliquots of PBS from the tube were plated in the following manner: 100 μl from each tube was lawn plated in triplicate (3×) on selective Chromogenic MRSA And MSSA agar. Plates were placed in incubator within 30 minutes of the plating procedure, and colonies were counted manually, and recorded 18 hrs after plating.

On day one of the study, all subjects underwent this exact procedure in arms 1 and 2 of the study two minutes before the laser procedure. They again were sampled in the same manner 2 minutes after the laser procedure. In the third arm of the study, they were swabbed two minutes before the procedure and the first antibiotic administration was completed after the laser therapy. The post/laser swab sample was taken for this arm 20 min later.

On day three of the study, all subjects from arms one two and three underwent the exact same procedures as day 1 of the study.

On day five all subjects from all arms underwent just one swabbing per nostril with the exact same sampling procedure one time.

Application of H202:

3% OTC hydrogen peroxide was applied to a cotton pledget for application to the subject prior to irradiation. This was inserted in the nose for 120 seconds and then removed. The subjects were then given doses of phototherapeutic near infrared radiation as described.

Application of Generic Topical Antimicrobial:

The subjects were first given doses of phototherapeutic near infrared radiation as described. Subsequently, 2% erythromycin paste was applied to a cotton tipped swab for application to the subject following irradiation. The swab was inserted approximately 1 cm in to the anterior nares and rotated 360 degrees several times and removed. Patients were instructed to perform the exact application procedure 3 times a day for the remaining 5 days.

Treatment Description

The NOVEON™ laser was used for two (2) six-minute treatments in each nostril on day (1) and day (3) of the study. The dosimetries used are shown in the Table TT, below.

The laser was calibrated before the first treatment of the day. Intermittent temperature testing of the treatment site was performed on each subject using a noncontact infrared thermometer (Raytek Minitemp), 30-60 second intervals. If a temperature of 110 F degrees was reached, or the patient complained of pain, the laser treatment was interrupted and only resumed when the patient was comfortable. Interruption only occurred once in 40 treatments (20 nostrils×2 treatments over three days), and was resumed 30 seconds later to completion.

TABLE 41

| Laser nm | power density W/cm2 | Length mm | Diameter mm | Area cm2 | Trans percent | set power W |
|---|---|---|---|---|---|---|
| 930 | 0.46 | 10 | 12 | 3.77 | 80 | 2.17 |
| 870 | 0.185 | 10 | 12 | 3.77 | 80 | 0.87 |
| 930 | 0.277 | 10 | 12 | 3.77 | 80 | 1.30 |
|  |  |  |  |  | 80 |  |
| 930 | 0.405 | 10 | 12 | 3.77 | 80 | 1.91 |
| 870 | 0.16 | 10 | 12 | 3.77 | 80 | 0.75 |
| 930 | 0.243 | 10 | 12 | 3.77 | 80 | 1.14 |
| both | 0.54 | 10 | 12 | 3.77 | 80 | 2.54 |
| both | 0.46 | 10 | 12 | 3.77 | 70 | 2.48 |

Quantitative Assessments to Measure Change in MRSA and MSSA Colonies

The following Tables 42-44 represent the mean values of the triplicate CFU counts and plating of each swab from each nostril, pre and post laser therapy (for this data set the mean is the sum of the observed and counted CFU's per plate, divided by the number of counted plates).

TABLE 42

| | Initial Analysis | | | | | | | |
|---|---|---|---|---|---|---|---|---|
| | Pre swab | | | | Post-treatment swab | | | |
| | left | | right | | left | | right | |
| Patient | s. aureus Average | MRSA Average | s. aureus Average | MRSA Average | s. aureus Average | MRSA Average | s. aureus Average | MRSA Average |
| Laser Alone | | | | | | | | |
| 01-003 | 407 | 0 | 442 | 0 | 1146 | 0 | 1291 | 0 |
| 01-006 | 549 | 0 | 1978 | 4 | 709 | 1 | 1333 | 1 |
| 01-010 | 0 | 0 | 507 | 0 | 0 | 0 | 454 | 0 |
| Laser w/ Peroxide | | | | | | | | |
| 01-002 | 1 | 0 | 0 | 0 | 0 | 0 | 0 | 0 |
| 01-004 | 53 | 63 | 29 | 30 | 20 | 22 | 506 | 455 |
| 01-007 | 17 | 0 | 285 | 0 | 1 | 0 | 146 | 0 |
| 01-009 | 124 | 4 | 3996 | 4032 | 0 | 1 | 3272 | 2752 |
| Laser w/ Erythromycin | | | | | | | | |
| 01-001 | 0 | 0 | 0 | 0 | 0 | 0 | 0 | 0 |
| 01-005 | 3045 | 3072 | 16 | 8 | 188 | 166 | 0 | 1 |
| 01-008 | 0 | 0 | 0 | 0 | 0 | 0 | 0 | 0 |

TABLE 43

| | Second Analysis | | | | | | | |
| --- | --- | --- | --- | --- | --- | --- | --- | --- |
| | Pre swab | | | | Post-treatment swab | | | |
| | left | | right | | left | | right | |
| Patient | s. aureus Average | MRSA Average | s. aureus Average | MRSA Average | s. aureus Average | MRSA Average | s. aureus Average | MRSA Average |
| Laser Alone | | | | | | | | |
| 01-003 | 2 | 0 | 0 | 0 | 0 | 0 | 0 | 0 |
| 01-006 | 227 | 0 | 3413 | 4 | 1175 | 2 | 1141 | 1 |
| 01-010 | 24 | 0 | 933 | 0 | 2 | 0 | 145 | 0 |
| Laser w/ Peroxide | | | | | | | | |
| 01-002 | 1 | 0 | 1 | 0 | 0 | 0 | 0 | 0 |
| 01-004 | 206 | 180 | 94 | 90 | 10 | 12 | 126 | 114 |
| 01-007 | 4 | 0 | 257 | 0 | 0 | 0 | 5 | 0 |
| 01-009 | 12 | 17 | 4373 | 3099 | 0 | 0 | 3589 | 3347 |
| Laser w/ Erythromycin | | | | | | | | |
| 01-001 | 0 | 0 | 0 | 0 | 0 | 0 | 0 | 0 |
| 01-005 | 71 | 76 | 0 | 0 | 0 | 0 | 0 | 0 |
| 01-008 | 0 | 0 | 0 | 0 | 0 | 0 | 0 | 0 |

TABLE 44

| | Third Analysis Swab | | | |
| --- | --- | --- | --- | --- |
| | left | | right | |
| Patient | s. aureus Average | MRSA Average | s. aureus Average | MRSA Average |
| Laser Alone | | | | |
| 01-003 | 193 | 0 | 359 | 0 |
| 01-006 | 387 | 0 | 645 | 5 |
| 01-010 | 22 | 0 | 387 | 0 |
| Laser w/ Peroxide | | | | |
| 01-002 | 1 | 0 | 1 | 0 |
| 01-004 | 868 | 827 | 586 | 563 |
| 01-007 | 28 | 0 | 52 | 0 |
| 01-009 | 0 | 0 | 3493 | 3648 |
| Laser w/ Erythromycin | | | | |
| 01-001 | 0 | 0 | 0 | 0 |
| 01-005 | 0 | 0 | 0 | 0 |
| 01-008 | 0 | 0 | 0 | 0 |

Results

We treated performed 36 treatments of 10 patients (20 infection sites) with zero negative sequelae from the laser in identified MRSA carriers based on a physician's evaluation of all the patients 2 days following the second laser therapy.

Patients 1 and 8 (in the laser plus antibiotic arm) were not treated a second time, as there was no growth of S. aureus or MRSA colonies present on the pre-test swabs. These patients were dismissed from the study by the principal investigator. The Laser alone arm was showed inconsequential colony reduction in MRSA and MSSA colonies in the nares. The Laser plus $H_2O_2$ arm may have had some transient benefit in some of the patients, but no obvious long-term efficacy.

The remaining patient (01-005) in the Laser/erythromycin that began the study with culturable S. aureus and MRSA showed a remarkable reduction in culturable bacterial from the colonization site as the treatments progressed, to the point of MRSA and MSSA eradication in both nostrils. In this patient, the combination of near infrared bacterial photodamage and topical antibiotics eradicated the MRSA infection. The heavily colonized nostril showed at least a 3 log reduction of bioburden, and resulted in no culturable bacteria; and the moderately colonized nostril showed at least a 2 log reduction of bioburden, and resulted in no culturable bacteria. Notably, the MRSA colony in that patient was not sensitive to erythromycin prior to phototherapy with the NOVEON™ laser system.

Part Two

A second human study was conducted, to further evaluate the therapeutic potential of the NOVEON™ laser system, including its ability to reverse drug resistance in bacteria. The study was conducted in a similar manner as Part One, above. Outcome measures assessed included both laboratory study and clinical observations.

Positive anterior nares cultures were obtained in six patients (12 nostrils) having nasal colonization of MRSA or MSSA, before initiating bacterial photodamage through doses of phototherapeutic near infrared radiation. One patient had MRSA only, 3 had MSSA only, and 2 had both MRSA and MSSA. All MRSA and MSSA were cultured and verified to be resistant to erythromycin.

Application of Topical Antimicrobial:

Antimicrobial paste (generic 2% erythromycin) was placed on a cotton tipped swab for application after phototherapeutic near infrared radiation. The swab was inserted approximately 1 cm in to the anterior nares of the subject, rotated 360 degrees several times and removed. The application of erythromycin was maintained for 3 times a day for the remainder of the study.

The laser was calibrated before the first treatment of the day and between each patient. The NOVEON™ laser was used for four six-minute treatments of the nares at the following sets of dosimetries (Tables 45), which were evaluated for safety in previous studies. Utilizing a 10 cm flat-top diffuser, each patient underwent exposure with the Noveon for 7 minutes (energy density—207 J/cm2) to each anterior nostril on Day 1 and on Day 3. The treatment was divided into two parts, an approximately 3-minute exposure using a combination of 870 nm and 930 nm and an approximately 3-minute exposure of 930 nm alone. Temperatures of the nares were recorded every 30 seconds with an IR temperature thermometer.

TABLE 45

| Laser nm | power density W/cm2 | Length mm | Diameter mm | Area cm2 | Trans percent | set power W | Laser Amp | set power W | IRB Power ratio |
|---|---|---|---|---|---|---|---|---|---|
| 930 | 0.46 | 10 | 12 | 3.77 | 80 | 2.17 | 5.95 | 2.17 | 1.00 |
| 870 | 0.185 | 10 | 12 | 3.77 | 80 | 0.87 | 4.65 | 0.87 | 0.40 |
| 930 | 0.277 | 10 | 12 | 3.77 | 80 | 1.30 | 4.85 | 1.30 | 0.60 |

Bacteriology

Quantitative cultures from each nostril were obtained and plated in triplicate on chromogenic agar before and 20 minutes after exposure on day 1 and day 3. A final culture was taken on day 5. Anterior nares specimens were collected on rayon-tipped swabs, and stored in Amies liquid transport medium. The nasal swab was plated on Columbia colistin-nalidixic agar (CNA) with 5% sheep blood, then incubated 18 to 48 hours at 35° C. in 5% CO2. S. aureus was identified by colony morphology and Staphaurex™ latex agglutination test (Murex Biotech Limited, Dartford, Kent, UK). Samples were frozen and stored at −20° C.

Results:

The Erythromycin resistant MRSA was completely cleared by culture in all 3 carriers, as was the E-mycin resistant MSSA in four of the five (5) carriers after the second laser treatment on day 3 and remained clear on day 5. In one patient the E-mycin resistant MSSA (baseline count>1000 CFU's) showed a 3-log reduction in MSSA on the day 5 culture. No sequelae or adverse events were observed. The average maximum temperature of the nares reached in all patients was 99 F.

Conclusions

NOVEON™ laser exposure at a non-damaging energy density and approximately physiologic temperatures, re-sensitized erythromycin resistant MRSA and MSSA to 2% generic erythromycin paste. Photodamage to the organism results in sensitivity to antibiotics in otherwise drug resistant strains. The NOVEON™ laser system provides for local reduction of drug resistant microbes and a concomitant reduction of bio-burden in: e.g., wounds, mucosal or cutaneous tissues, and other colonized or infected areas such as surgical sites and tissue/medical device interfaces, which are prone to contamination particularly by nosocomial strains of microbes frequently having multidrug resistance phenotypes.

Exemplary NIMELS Systems

Figure 17:
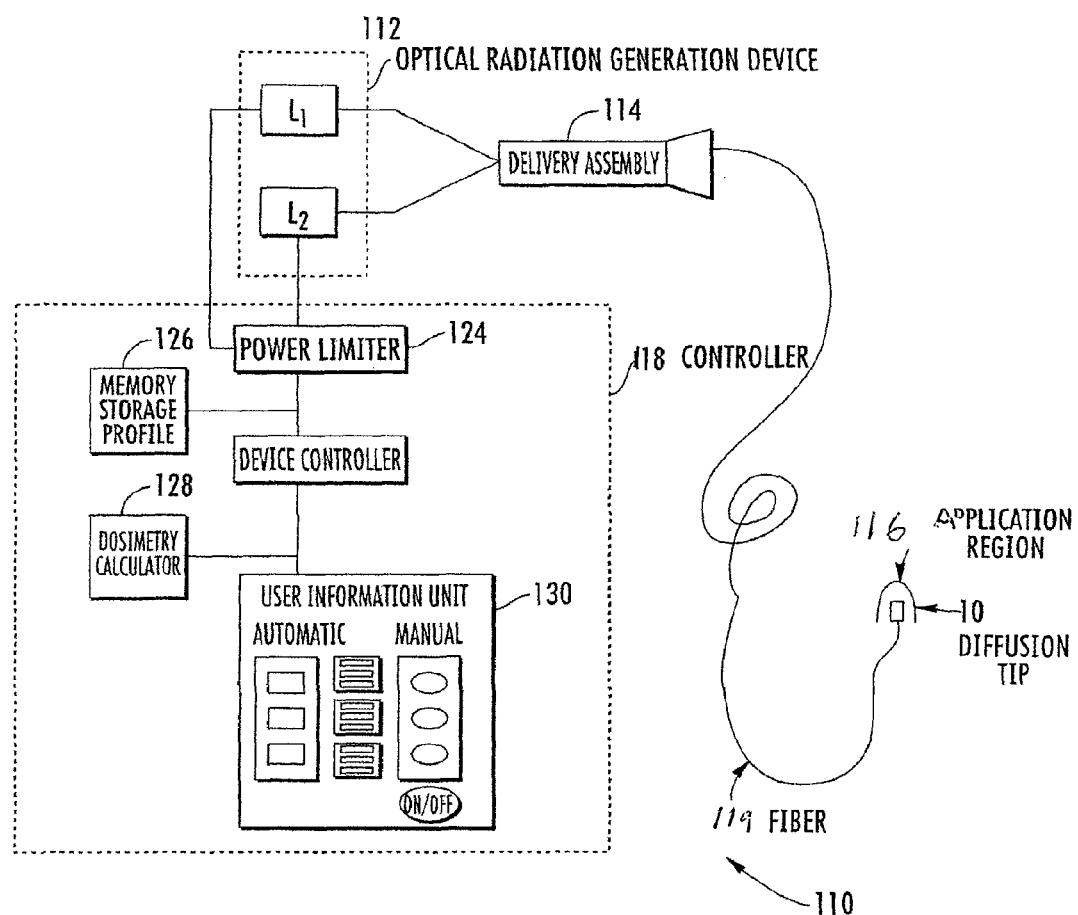
FIG. 17 illustrates an exemplary NIMELS treatment system.

FIG. 17 illustrates a schematic diagram of a therapeutic radiation treatment device according one embodiment of the present disclosure. The therapeutic system 110 includes an optical radiation generation device 112, a delivery assembly 114, an application region 116, and a controller 118.

According one aspect of the present disclosure, the optical radiation generation device (source) includes one or more suitable lasers, L1 and L2. A suitable laser may be selected based on a degree of coherence. In exemplary embodiments, a therapeutic system can include at least one diode laser configured and arranged to produce an output in the near infrared region. Suitable diode lasers can include a semiconductor materials for producing radiation in desired wavelength ranges, e.g., 850 nm-900 nm and 905 nm-945 nm. Suitable diode laser configurations can include cleave-coupled, distributed feedback, distributed Bragg reflector, vertical cavity surface emitting lasers (VCSELS), etc.

With continued reference to FIG. 17, in certain embodiments the delivery assembly 114 can generate a "flat-top" energy profile for uniform distribution of energy over large areas. For example, a diffuser tip 10, may be included which diffuses treatment light with a uniform cylindrical energy profile in an application region 116 (e.g. a nasal cavity as described in the example above). As noted, the optical radiation generation device 112 can include one or more lasers, e.g., laser oscillators L1 and L2. In exemplary embodiments, one laser oscillator can be configured to emit optical radiation in a first wavelength range of 850 nm to 900 nm, and the other laser oscillator can be configured to emit radiation in a second wavelength range of 905 nm to 945 nm. In certain embodiments, one laser oscillator is configured to emit radiation in a first wavelength range of 865 nm to 875 nm, and the other laser oscillator 28 is configured to emit radiation in a second wavelength range of 925 nm to 935 nm. The geometry or configuration of the individual laser oscillators may be selected as desired, and the selection may be based on the intensity distributions produced by a particular oscillator geometry or configuration.

With continued reference to FIG. 17, in certain embodiments, the delivery assembly 114 includes an elongated flexible optical fiber 118 adapted for delivery of the dual wavelength radiation from the oscillators 26 and 28 to diffuser tip 10 to illuminate the application region 116. The delivery assembly 14 may have different formats (e.g., including safety features to prevent thermal damage) based on the application requirements. For example, in one form, the delivery assembly 114 or a portion thereof (e.g. tip 10) may be constructed with a size and with a shape for inserting into a patient's body. In alternate forms, the delivery assembly 114 may be constructed with a conical shape for emitting radiation in a diverging-conical manner to apply the radiation to a relatively large area. Hollow waveguides may be used for the delivery assembly 114 in certain embodiments. Other size and shapes of the delivery assembly 14 may also be employed based on the requirements of the application site. In exemplary embodiments, the delivery assembly 114 can be configured for free space or free beam application of the optical radiation, e.g., making use of available transmission through tissue at NIMELS wavelengths described herein. For example, at 930 nm (and to a similar degree, 870 nm), the applied optical radiation can penetrate patient tissue by up to 1 cm or more. Such embodiments may be particularly well suited for use with in vivo medical devices as described herein.

In an exemplary embodiment, the controller 118 includes a power limiter 124 connected to the laser oscillators L1 and L2 for controlling the dosage of the radiation transmitted through the application region 116, such that the time integral of the power density of the transmitted radiation per unit area is below a predetermined threshold, which is set up to prevent damages to the healthy tissue at the application site. The controller 118 may further include a memory 126 for storing treatment information of patients. The stored information of a particular patient may include, but not limited to, dosage of radiation, (for example, including which wavelength, power density, treatment time, skin pigmentation parameters, etc.) and application site information (for example, including type of treatment site (lesion, cancer, etc.), size, depth, etc.).

In an exemplary embodiment, the memory 126 may also be used to store information of different types of diseases and the treatment profile, for example, the pattern of the radiation and the dosage of the radiation, associated with a particular type of disease. The controller 118 may further include a dosimetry calculator 128 to calculate the dosage needed for a particular patient based on the application type and other application site information input into the controller by a physician. In one form, the controller 118 further includes an imaging system for imaging the application site. The imaging system gathers application site information based on the images of the application site and transfers the gathered information to the dosimetry calculator 128 for dosage calculation. A physician also can manually calculate and input information gathered from the images to the controller 118.

As shown in FIG. 17, the controller may further include a control panel 130 through which, a physician can control the therapeutic system manually. The therapeutic system 10 also can be controlled by a computer, which has a control platform, for example, a WINDOWS™ based platform. The parameters such as pulse intensity, pulse width, pulse repetition rate of the optical radiation can be controlled through both the computer and the control panel 30.

Figure 18A:
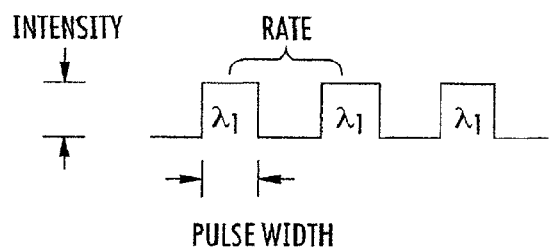
FIGS. 18*a*-18*d* illustrate the delivery of treatment light from a NIMELS treatment system.
Figure 18B:
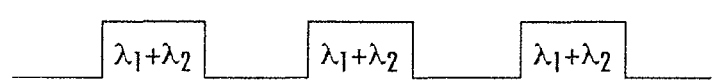
Figure 18C:
Figure 18D:
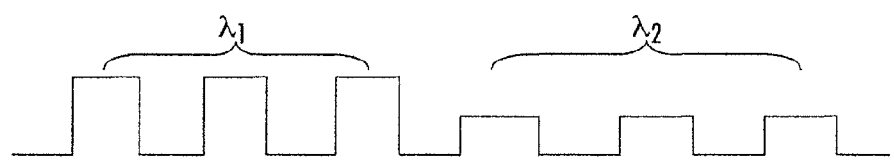

FIGS. 18a-18d show different temporal patterns of the optical radiation that can be delivered from the therapeutic system to the application site. The optical radiation can be delivered in one wavelength range only, for example, in the first wavelength range of 850 nm to 900 nm, or in the range of 865 nm to 875 nm, or in the second wavelength range of 905 nm to 945 nm, or in the range of 925 nm to 935 nm, as shown in FIG. 18a. The radiation in the first wavelength range and the radiation in the second wavelength range also can be multiplexed by a multiplex system installed in the optical radiation generation device 112 and delivered to the application site in a multiplexed form, as shown in FIG. 18b. In an alternative form, the radiation in the first wavelength range and the radiation in the second wavelength range can be applied to the application site simultaneously without passing through a multiplex system. FIG. 18c shows that the optical radiation can be delivered in an intermission-alternating manner, for example, a first pulse in the first wavelength range, a second pulse in the second wavelength range, a third pulse in the first wavelength range again, and a fourth pulse in the second wavelength range again, and so on. The interval can be CW (Continuous Wave), one pulse as shown in FIG. 18c, or two or more pulses (not shown). FIG. 18d shows another pattern in which the application site is first treated by radiation in one of the two wavelength ranges, for example, the first wavelength range, and then treated by radiation in the other wavelength range. The treatment pattern can be determined by the physician based on the type, and other information of the application site.

Delivery Apparatus

Several non-limiting examples of delivery devices that may be used in the delivery assembly 114 of the exemplary NIMELS system are described herein. For example, delivery devices of the types described herein may make up an end portion of the fiber 119 of the delivery assembly 114. These delivery devices may operate with or without the diffuser tip 10.

For example, referring to FIG. 19, the improved delivery device 510 includes an optical fiber 512 having a fiber-optic core 514, a cladding layer 516 circumferentially disposed around the core 514, and an outer buffer coating 518 circumferentially disposed around the cladding layer 516. In some embodiments, as shown, the outer buffer coating 518 is removed from the emission end of the optical fiber 512, and the fiber-optic core 514 and cladding 516 extend to position close to but not in optical contact with the optical element 530. In some embodiments, the separation of these two elements determines the imaging properties of the emitted beam. For example, in some embodiments, the optical element 530 may be a focusing lens having a focal plane located at or near the end face of the fiber optic core 514, thereby imaging the core to an image plane. In other embodiments, the optical element 530 may abut the end of the optical fiber 512.

At its proximal end, the housing 520 is adapted to accept the fiber optic 512 and the region having buffer coating 516 removed. At its distal end, the housing 520 firmly holds and aligns the optical element 530 with the fiber core 514. For example, in some embodiments housing 520 is an elastic cuff. The cuff is stretched perpendicular to the longitudinal axis of the optical fiber 512 providing a press fit that holds the optical components 512, 530 together.

In various embodiments, the coupling and positioning between multiple source fibers, the integrating optical fiber, the housing, the buffer, and the optical element enables a substantially improved precise and stable uniform beam in a durable construction unaffected by the extreme thermal cycling of sterilization and other treatments. According to an embodiment of the invention, the housing is made from a material having a coefficient of thermal expansion approximately equal to the coefficient of thermal expansion of the buffer. In this manner, both the housing and the buffer will thermally expand (and contract) approximately the same amount, thus minimizing the effects of heat cycling on the device.

According to one embodiment, the housing is made from a polymer material having an anisotropic, non-linear Young's modulus with the greater value co-axial with the optical fiber. Also according to preferred embodiment of the invention, the housing is made with a low index (e.g. lower than that of the optical element) of refraction material to act as a cladding to the encased optical component. In some embodiments the housing may have an index of refraction less than 1.7, less than 1.6, less than 1.5, less than 1.4, less than 1.3, or even less.

Figure 20A:
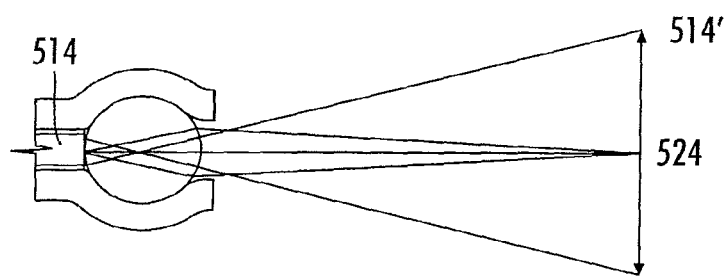
FIGS. 20*a* & *b* shows the core imaging principal and intensity distribution of the present invention.
Figure 20B:
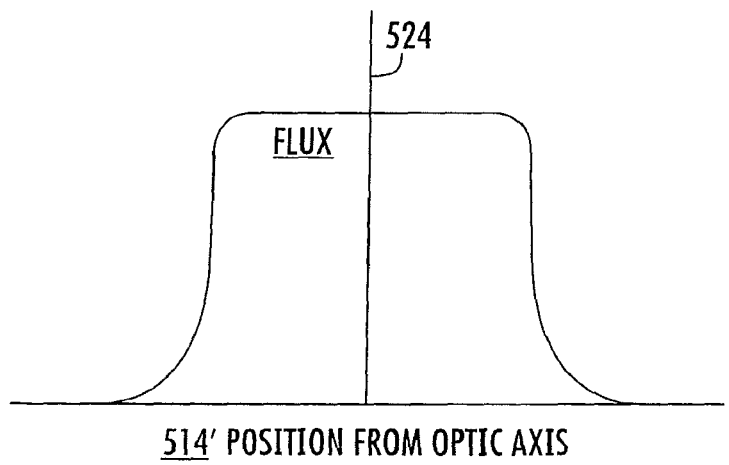

In some phototherapy applications it is important that a precise, uniform beam be employed for many conditions. Biophotonic responses are complex, and unpredictable variations in illumination may result in unnecessary damage to healthy tissues or the survival of malignant pockets, among other side effects. In a preferred embodiment shown in FIG. 20a, an image 514' of the core 514 of the optical fiber 512 is focused by optical element 530 at the design region of illumination 524. This results in a uniform spatial intensity or 'top hat' at the design region of illumination 524 as shown in graph of intensity verses axial spatial position in FIG. 20(b). Accordingly, in some embodiments, delivery device 510 produces a beam with a substantially non-gaussian beam profile. The beam profile may vary in intensity by less than 10%, less than 5%, or even less than 1% across the substantially the entire profile of the beam). For example, as shown in FIG. 20(b) the beam is very uniform except at a small peripheral region where the intensity quickly drops to near zero.

Figure 21:
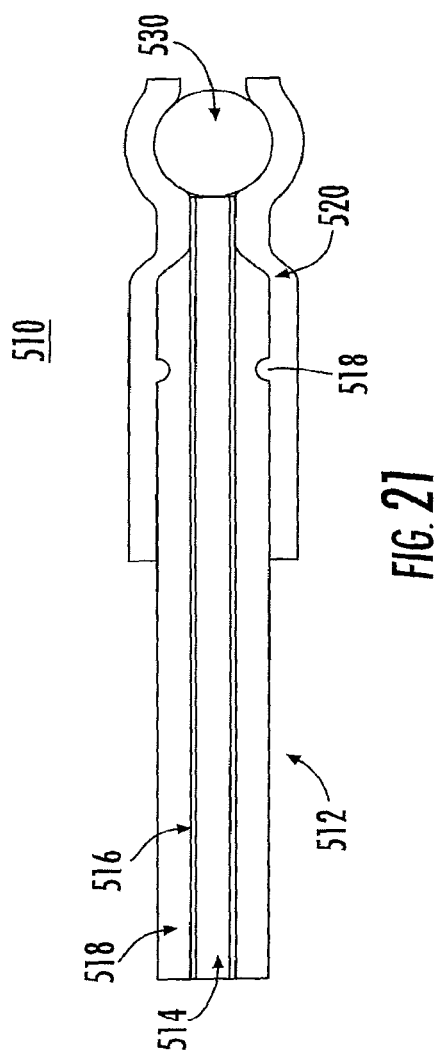
FIG. 21 shows the positive-locking, buffer-housing system.

FIG. 21 shows a construction of the delivery device 510 having a protrusion on the interior face of the 5 housing 520 locking at a recess on the buffer coating 518. The recess 518 may be pre-fabricated or the result of the assembly of the components.

Figure 22:
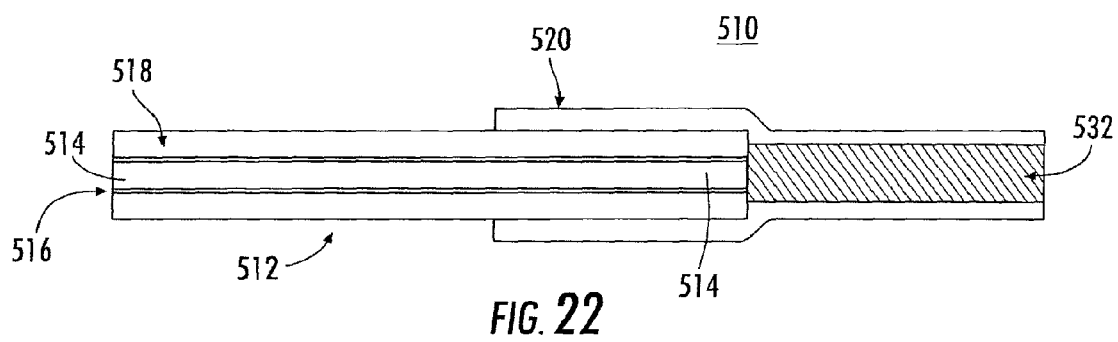
FIG. 22 shows a GRIN embodiment of the present invention.

In another embodiment shown in FIG. 22, a GRIN lens 532 is used in place of the optical element 530. The GRIN lens 532 normally abuts the coupling core 514. In various embodiments, any suitable optical element may be used to produce any desired illumination pattern at an illumination region. For example, the optical element may include a lens (e.g. a spherical lens, aspherical lens, compound lens, singlet, doublet, etc.), a GRIN lens, a diffractive element, a diffusive element, a hologram, a concentrating element, and a collimator. In some embodiments, more than one optical element may be used.

Figure 23:
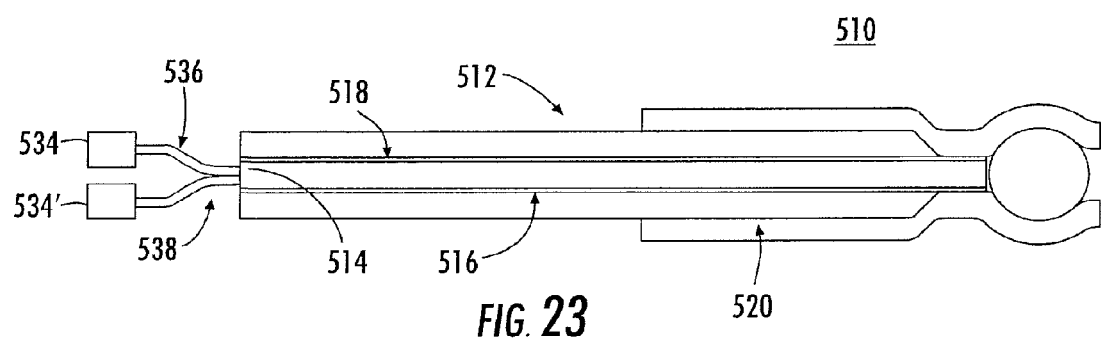
FIG. 23 shows a multiple-source optical fiber integration embodiment.

FIG. 23 shows a preferred integrating embodiment of delivery device 510. As shown, a multiplicity of sources 534, 534' may be of different wavelengths or wavelength ranges (e.g. either distinct ranges or partially overlapping ranges). Each of the sources 534, 534' are optically coupled at an input end, respectively, to the source output optical fibers 536 and 538. The source output fibers each transmit light to an output end optically couples to the core 514 of the principal integrating optical fiber 512. This construction enables a transmission efficiency of up to about 92% or more and a uniform mixing of the individual sources during the transmission in the principal fiber 512. In some embodiments, sources 534, 534' may be lasers L1 and L2 of the NIMELS system shown in FIG. 17. In some embodiments, one or more optical elements (not shown) may be used to couple light from the source output fibers 436 and 538 to integrating fiber 512.

Note that although two source output fibers are shown above, in various embodiments more or fewer may be used. In some embodiments, at least a portion (e.g. the output end portion) of each of the source output optical fibers may have a diameter less than that of the integrating fiber. In some embodiments, the total combined packed diameter of the source output optical fibers may be less than that of the integrating fiber. For example, as shown in FIG. 23, the combined diameter of the output ends of the source output fibers 536 and 538 is less than the diameter of the core 514 of the integrating fiber 512.

Figure 24A:
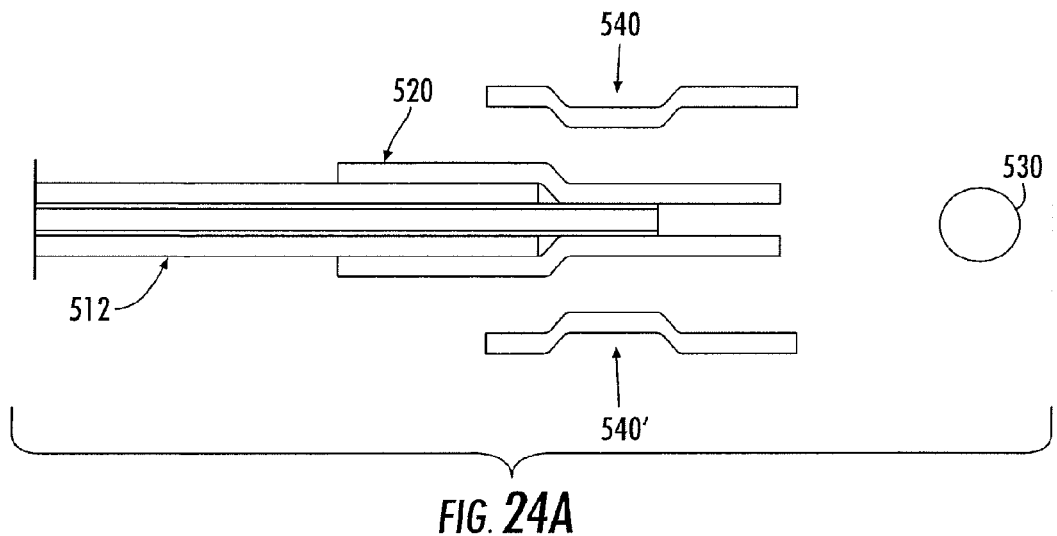
FIGS. 24*a*-24*d* shows assembly methodology including the principal optical fiber, buffer, housing and optical element and press-fit template.
Figure 24B:
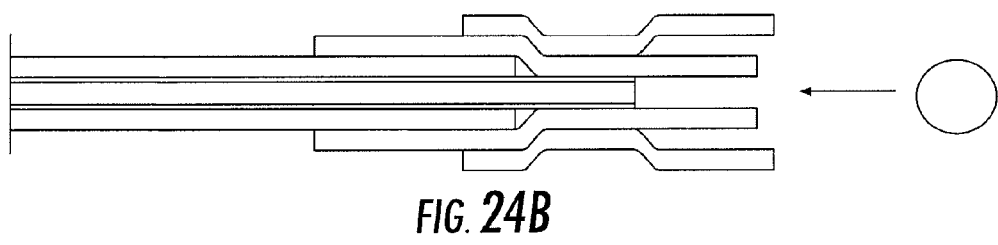
Figure 24C:
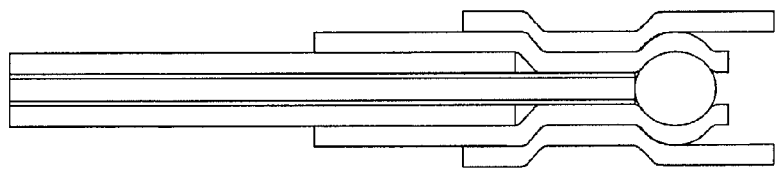
Figure 24D:
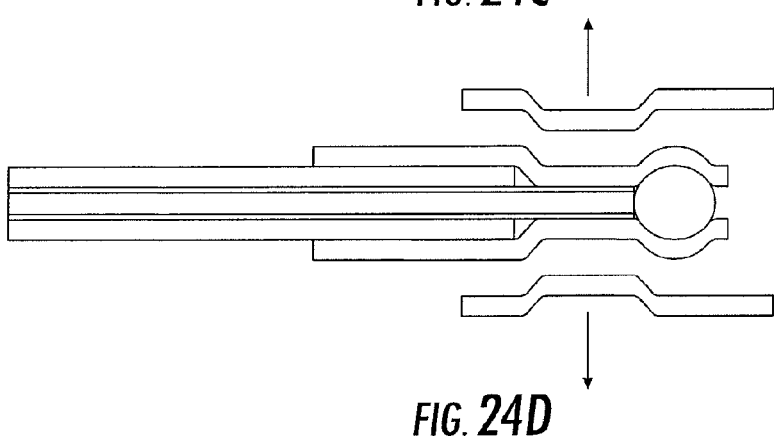

FIGS. 24a-24d show a method for the construction of the device described above. In FIG. 24a, one end of the housing 520 is stretched over the end of the fiber 512. In FIG. 24b an alignment template 540 is temporarily affixed to the optical fiber 512 enabling the accurate insertion and alignment of the optical element 530, as shown in FIGS. 24b and 24c. The alignment template 540 may be of a solid material and a split construction 540, 541'. In FIG. 24d, the alignment template 540 is removed.

The above described press-fit process provides the precise, controlled alignment and seating of the elements. It may be accomplished in a stable, temperature controlled environment, within the elastic modulus of the materials, further eliminating alignment errors and post manufacturing transitions. For example, the entire process may be accomplished ay room temperature, at temperatures below 500 C, below 400 C, below 300 C, below 200 C, below 100 C, below 50 C, or less. The process has substantial advantages over a heat-shrink construction by eliminating the potential heat damage to the cladding, the heat-induced stresses in the optical element and the resulting misalignment from post-manufacturing cooling. Further, it permits the use of more stable optical, cladding, buffer and housing materials. These include but are not limited to new improved polymer optics whose operational temperature is less than 500 C.

Figure 25:
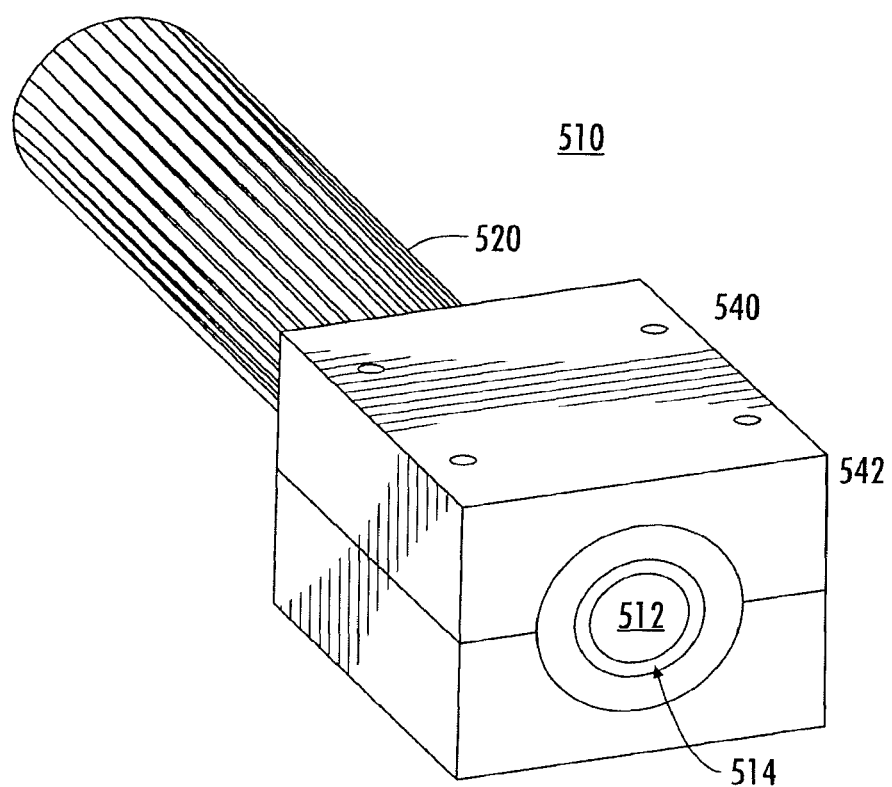
FIG. 25 shows a compressible mechanical assembly

In one embodiment, fluoro-polymer materials, such Teflon® materials and the like, are used as materials for the housing 520 to inhibit contact-adhesion between the tip assembly and biological tissue during procedures. In some embodiments, the Teflon® material is a Teflon® FEP material (a polyperfluoroethylene-6 propylene copolymer). Other Teflon® materials such as Teflon® PFA (a polytetra-fluoro-ethylene polymer with perfluoro-alkoxy side chains) and Teflon® PTFE (polytetrafluoroethylene) also can be useful in certain applications. Press-fit process has substantial advantages over a heat-shrink construction as a result of, including but not limited, improved precision of construction; stable optical properties;

FIG. 25 shows an embodiment wherein two sides of a low index of refraction clamshell clamp 542, which when compressed holds and position the fiber and optical element. The clamp may have an index of refraction less than the optical element 530, thereby serving as a cladding for the element.

The above has described delivery device 510 used with a NIMELS, but it is to be understood that the may be used with any phototherapeutic devices, e.g., any multi-wavelength device where it is desirable to integrate light output from multiple sources.

Fiber Diffusion Tip

As noted above, in some embodiments, treatment system 110 employs a diffusion tip 10 to diffuse therapeutic treatment light delivered from a therapeutic light source by optical fiber 118. The tip operates to provide a desired illumination profile (i.e. emitted intensity profile) at the application region 116. For example, as described above, in embodiments where treatment light is applied to the nares, a substantially uniform cylindrical illumination profile is desirable. Other embodiments of tip 10 may be used to direct treatment light to other areas such as tissue spaces (e.g. the periodontal pocket or within a joint e.g. in an orthopedic surgical procedure), interfaces between body tissue and other surfaces (e.g. the surface of an implantable medical device), over a wide area such as a dermal surface, etc.

The following describes several embodiments of diffuser tips suitable for use with the treatment techniques and devices described herein.

In one embodiment, diffuser tip 10 is an optically transmissive, light diffusing, fiber tip assembly having an entrance aperture through a proximal reflector, a radiation-scattering, transmissive material surrounding an enclosed void (e.g. a cylindrical cavity), and a distal reflective surface is disclosed. As radiation propagates through the fiber tip, a portion of the radiation is scattered in a cylindrical (or partly cylindrical) pattern along the distal portion of the fiber tip. Radiation, which is not scattered during this initial pass through the tip, is reflected by at least one surface of the assembly and returned through the tip. During this second pass, the remaining radiation, (or a portion of the returning radiation), is scattered and emitted from the proximal portion of the tube. Multiple additional reflections off of the proximal and distal reflectors provide further homogenization of the intensity profile. Preferably the scattering medium has a prescribed inner diameter. This inner diameter of the scattering material is designed such that the interaction with this material and the multiple reflections off of the cavity reflectors interact to provide a substantially proscribed axial distribution of laser radiation over the length of the tip apparatus. Various embodiments provide a diffusing tip with control over the emitted axial and azimuthal energy distributions.

The diffusion techniques and devices disclosed herein are generally applicable for diffusing radiation from an optical fiber to provide a larger exposure area for photo-illumination. Some embodiments are particularly useful as part of a fiber-optic based medical laser system in which a lower aspect ratio of length to diameter than typical diffuser designs is desirable. Suitable laser systems include those described herein along with those described in U.S. patent application Ser. No. 11/930,941 filed 31 Oct. 2007 and U.S. patent application Ser. No. 11/981,486 filed 31 Oct. 2007; the entire contents of both of which applications are incorporated herein by reference.

Some embodiments provide substantially uniform energy distribution to a major portion of the exposure area. Some embodiments provide for constructing and implementing circumferential and/or sideways emitting diffusing tip assemblies for optical fibers to direct laser radiation in a radially outward pattern relative to the fiber's longitudinal axis. As used herein the term "optical fiber" is intended to encompass optically transmissive waveguides of various shapes and sizes.

Some diffusing tip designs are intended for a higher aspect ratio of length to diameter. Typical aspect ratios for prior art diffusing tip technologies are usually from 20 to 1 and higher. (e.g. 1 mm diameter and 20 mm length). Some embodiments of the diffusion tips described herein allow for producing diffusing tip assemblies with aspect ratios of about 10 or less, about 1 or less, or about 0.1 or less. For example, one embodiment may be used to produce uniform emission from a diffusing tip with 10 mm diameter and 10 mm length. The aspect ratio of this diffusing tip would be 1.

In one embodiment, a diffusive tip assembly is disclosed for diffusing radiation from an optical fiber. The tip assembly includes a light transmissive, tubular housing, alignable with, and adapted to receive, the distal end of the fiber and serve as a diffusive scattering medium for light that has been emitted by the optical fiber. The assembly further includes a reflective cavity formed by reflectors on each side of the diffusive tube, such that the light is scattered by the tube on it's first pass through the tube, and is emitted outward to the illumination site. The un-scattered portion of the illumination is reflected back to further interact with the scattering tube. This second pass illumination is then scattered outward by the scattering tube to complement the light emitted on the first pass to produce the desired illumination profile. Additional 2nd, 3rd and 4th reflections with subsequent scattering from the diffusing tube can be added to produce additional homogeneity of the emitted axial energy profiles.

The reflective surfaces of the apparatus can also be modified to effect non-planar forms. Reflective structures are disclosed which control the spatial distribution of the light emitted from the tip. These techniques and structures permit, for example, an evenly distributed orthogonal projection of the radiation.

In another aspect, the diameter of the tubular scattering material and/or the length of the diffusing tip can be controlled such that the diffusion of the radiation during the initial and reflected paths are complementary. By proper choice of such parameters, the cumulative energy profile, or fluence, along at least a portion of the fiber tip can be rendered uniform. The term "substantially uniform" is commonly used in the field of phototherapy to describe light diffusers that possess a uniformity of about +/−15% or less of the average intensity of light emitted from the diffusive tip assembly. Thus embodiments of tip 10 provide a mechanism for substantially uniform cylindrical illumination of biological structures and other illumination applications.

In some embodiments, the diffuser tips described herein may be used to apply therapeutic light at NIMELS dosimetry and wavelengths (e.g. as described above) without exhibiting heating to temperatures which are unwanted or intolerable at the treatment site (i.e. temperatures that would cause substantial thermal damage at the site, or discomfort to a patient undergoing treatment). For example, in some embodiments, the diffuser tip may absorb about 20% or less of the therapeutic light delivered from a therapeutic source at NIMELS dosimetry and wavelengths. In some embodiments, the diffuser tip may be operated to deliver therapeutic light at NIMELS dosimetry and wavelengths for treatment times on the order tens of seconds or on the order of minutes or more while remaining at an operating temperature of 110 F degrees or less, or 100 F degrees or less.

Figure 26:
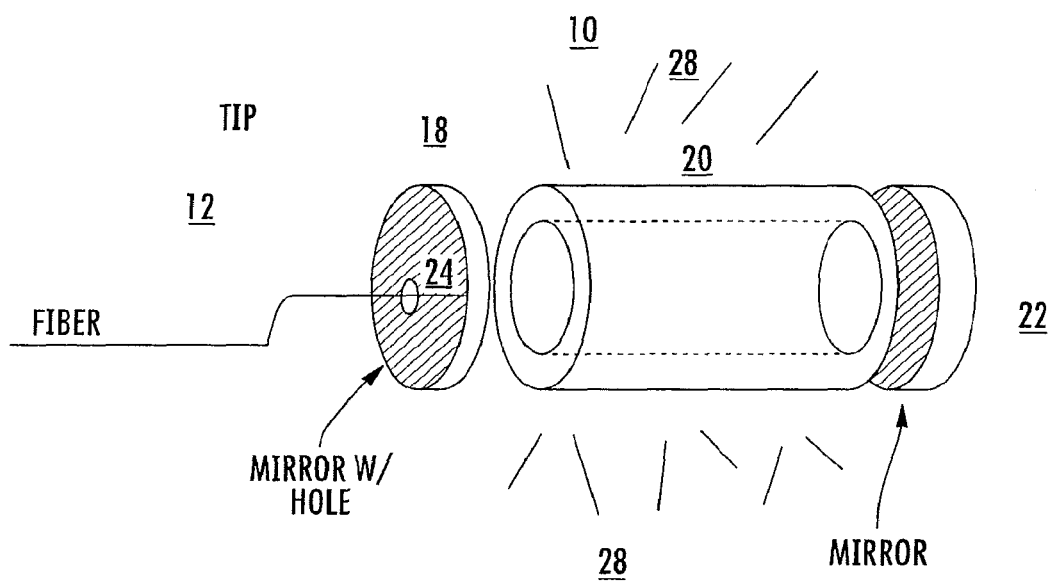
FIG. 26 is a perspective illustration of a diffusive fiber tip device.

In FIG. 26 an optical fiber diffusive tip assembly 10 is shown including and optical fiber 12 having a light transmissive core 14, a cladding 16, a proximal first mirror 18, a diffusing tube 20, and a distal second mirror 22. The end face of fiber 12 is inserted through an aperture 24 in the first mirror 18.

Figure 27:
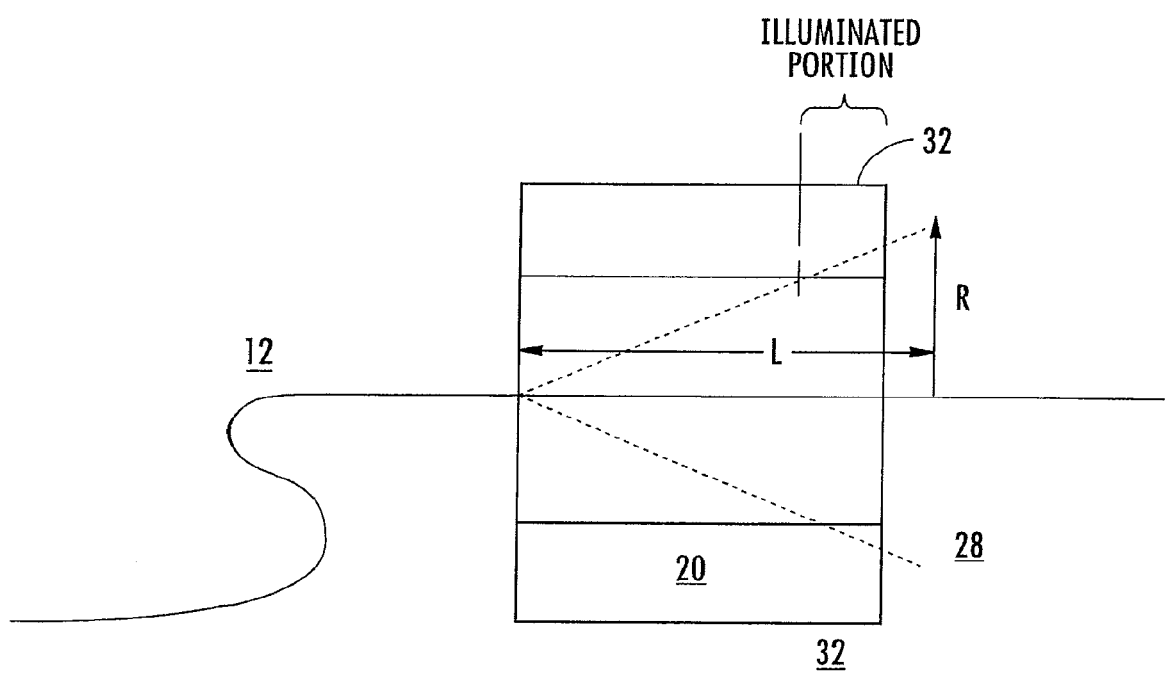
FIG. 27 is a cross sectional representation of a diffusive fiber tip device that shows how the light emitted from a fiber optic initially interacts with a diffusion tube without the mirrors that form the reflective cavity.

In FIG. 27, the operation of diffuser tip 10 is shown where the radiation 28 from the fiber 12 expanding at angle defined by numerical aperture NA intersects the diffusing tube 20. As indicated, a distal portion 32 of diffusing tube 20 is illuminated by light which intersects the tub and is scattered radially outward.

Figure 28:
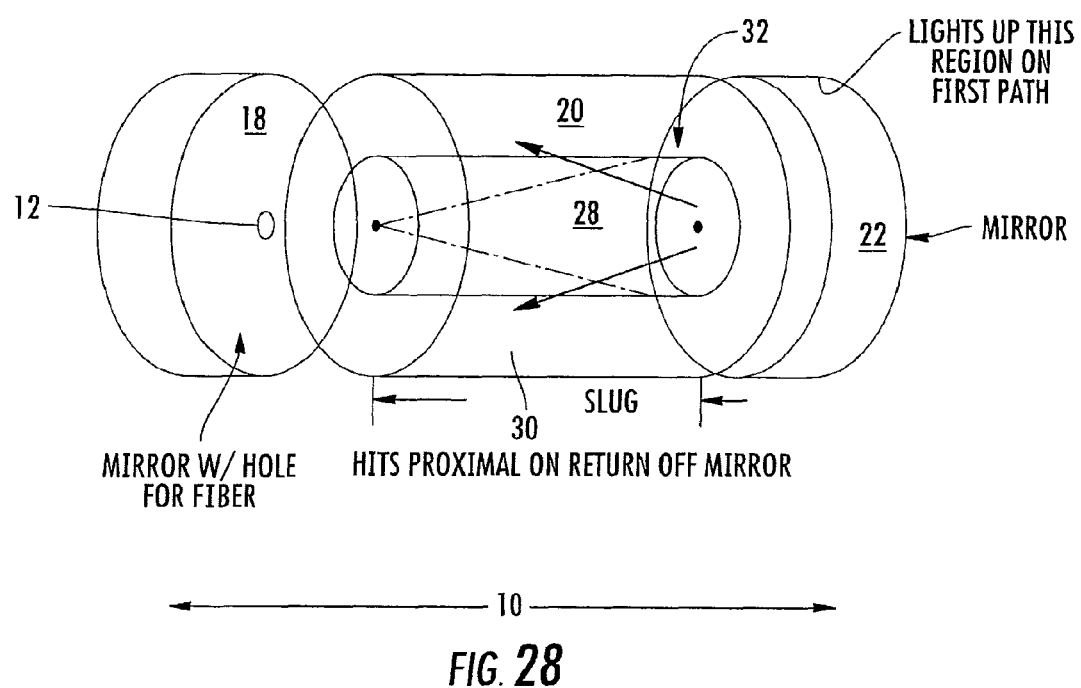
FIG. 28 is a perspective illustration of the operation of the diffusing tube of FIG. 20 with the addition of the cavity mirrors.

FIG. 28 shows the operation of diffuser tip 10 where the radiation 28 from the fiber 12 which does not interact with the diffusing tube 20 reflects back into the void 30 from the distal mirror 22. The diffusing tube may be constructed from many materials with suitable optical and scattering properties, but preferably from those materials with low absorption (e.g. less than 20% of the incident intensity) and high scattering properties, of which expanded poly-tetrafluoroethylene (PTFE) is an example. Radiation which propagates into the diffusing material 20 is efficiently scattered in region 32 with a portion escaping the material 20 and emerging into external space. A portion of the radiation 28 is returned into the void 30 where it is propagated into another region of the diffusing tube 20 or continues to be reflected by first or second mirrors 18, 22. The radiation scattered out of tube 20 sums to a cumulative illumination pattern which depends on properties of tip 10 (e.g. the distance between the reflectors, the size of the interior void, the curvature of the reflectors, etc.).

Figure 29:
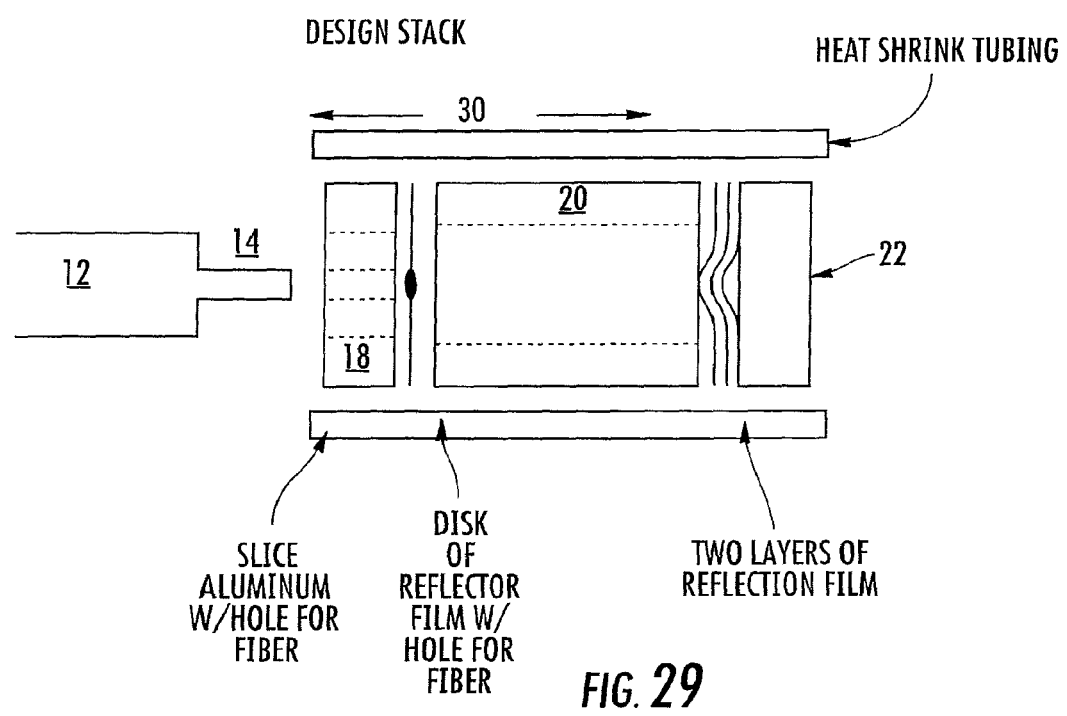
FIG. 29 is a cross sectional illustration of a curved mirror embodiment of a diffusive fiber tip assembly.

For example, FIG. 29 shows the diffusive tip assembly 10. Shown are the optical fiber 12, a proximal first mirror 18, a diffusing tube 20, and a distal second mirror 22 having a curved reflective face. FIG. 23 shows a graph of the tip's light intensity (ordinate) as a function of axial position (ordinate) for a planar distal mirror 22 (left graph) and for a curved distal second mirror 22 (right graph). For this configuration the void in the diffusion tube 20 was larger than preferred to provide a uniform axial intensity distribution. In this design regime a properly curved second mirror 22 can increase the uniformity of the tip's axial intensity profile.

Figure 30:
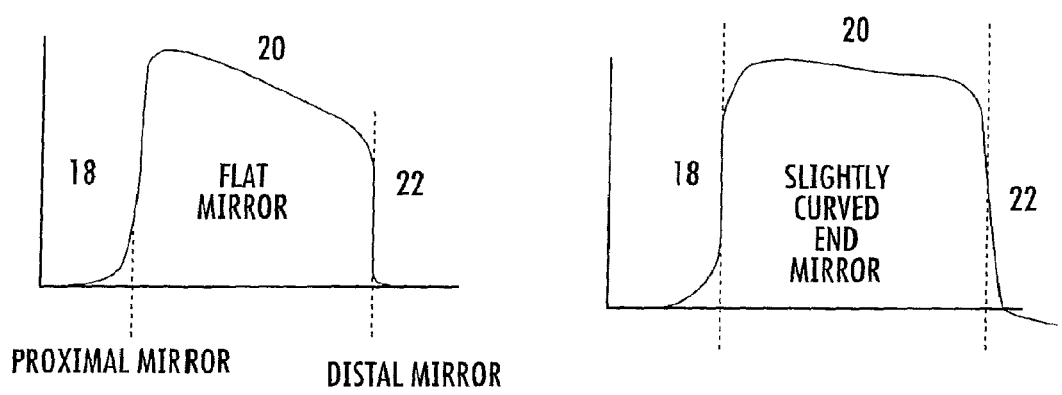
FIG. 30 shows intensity profiles observed from the operation of the diffusive tip assembly.
Figure 31:
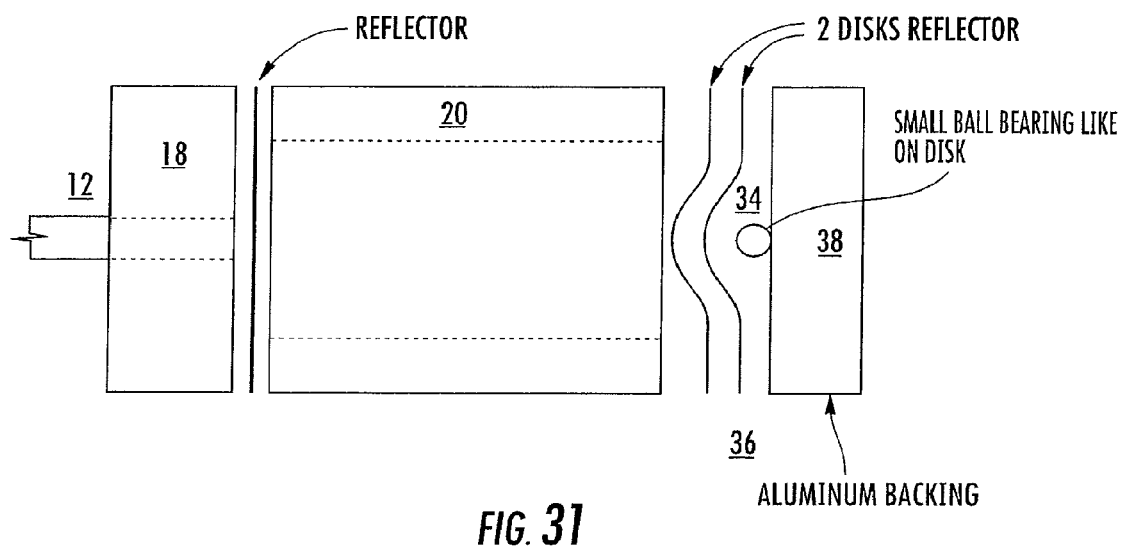
FIG. 31 is a cross sectional illustration of an exemplary construction of a curved mirror embodiment of the diffusive tip assembly.

FIG. 30 shows a method of construction of the curved second mirror 22 where a small form or sphere 34 is placed between the flexible reflective films 36 and the distal backing of the second mirror assembly 22. An example of a flexible reflective film is 3M Vikuity enhanced specular reflective film.

Figure 32:
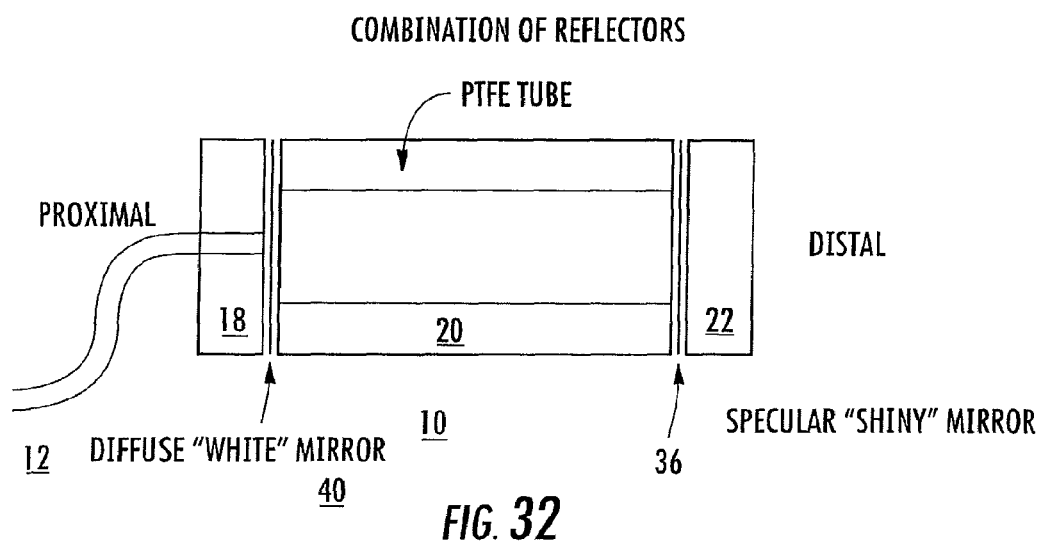
FIG. 32 is a cross sectional illustration of an exemplary construction of the diffusive reflector embodiment of the diffusive fiber tip assembly.

FIG. 32 shows a cross section of the fiber tip 10 having a proximal first mirror 18 with diffuse reflective surface 40. An example of this kind of film is white Backlight reflector sheet made of a polyester film such as that produced by Kimoto.

This alternative construction enables an improved radiant uniformity when factors including, but not limited to, cost and simplicity of construction are considered. In some embodiments, the distal mirror 36 may be specular or diffuse, preferably specular. The proximal mirror may be specular or diffuse, preferably diffuse.

Figure 33:
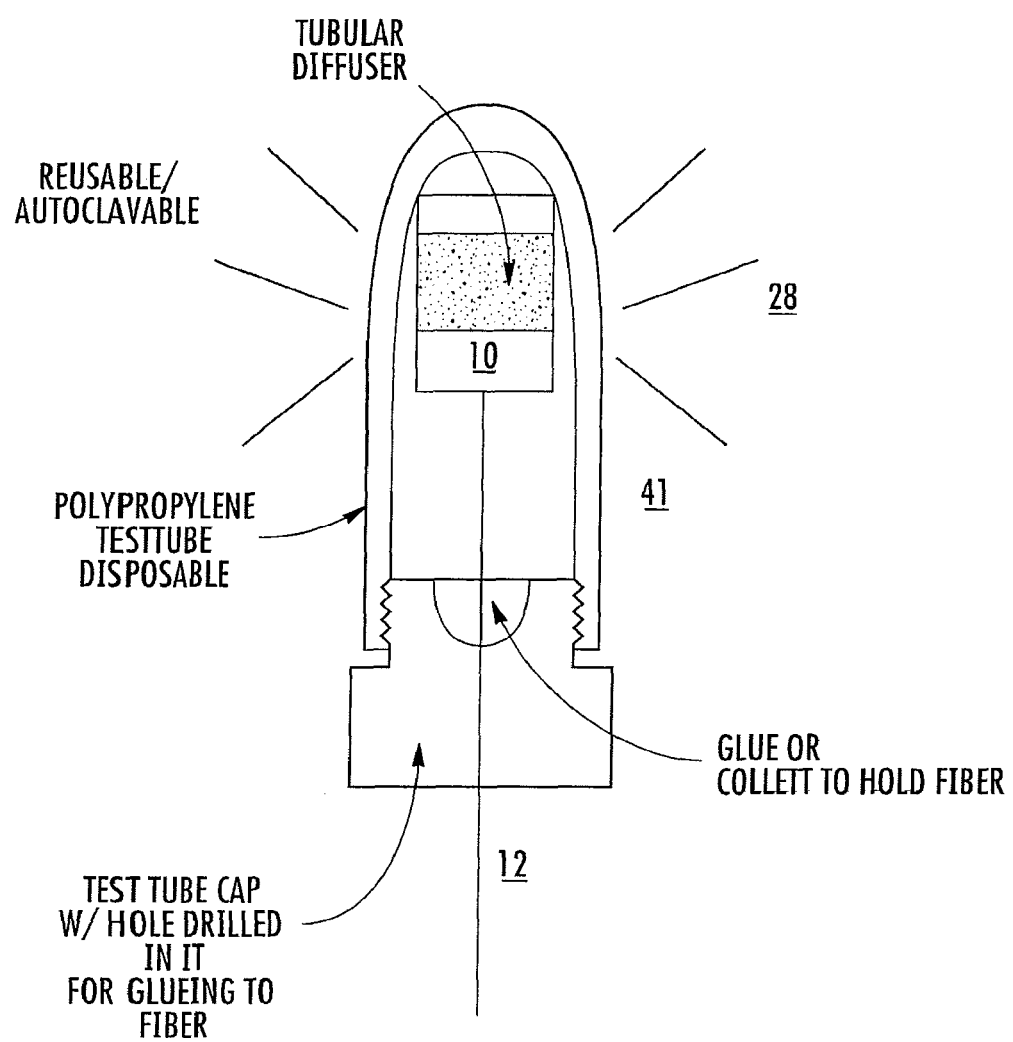
FIG. 33 is a drawing of a reusable diffusion tip encased in a disposable polypropylene outer jacket.

FIG. 33 shows an embodiment of diffuser tip 10 where the diffusion tube is enclosed by a disposable, sterile, test tube sized appropriately for the diffusion tip assembly. A preferred disposable tube is made from Polypropylene, due to its high transmission of visible and near infrared light, non shattering nature and ability to withstand high temperatures. Alternate materials could include polycarbonate or Pyrex glass. In some embodiments diffuser tip 10 is autoclavable and reusable. In other embodiments, diffuser tip 20 is detachably connected to fiber 12, and is disposable.

Figure 34:
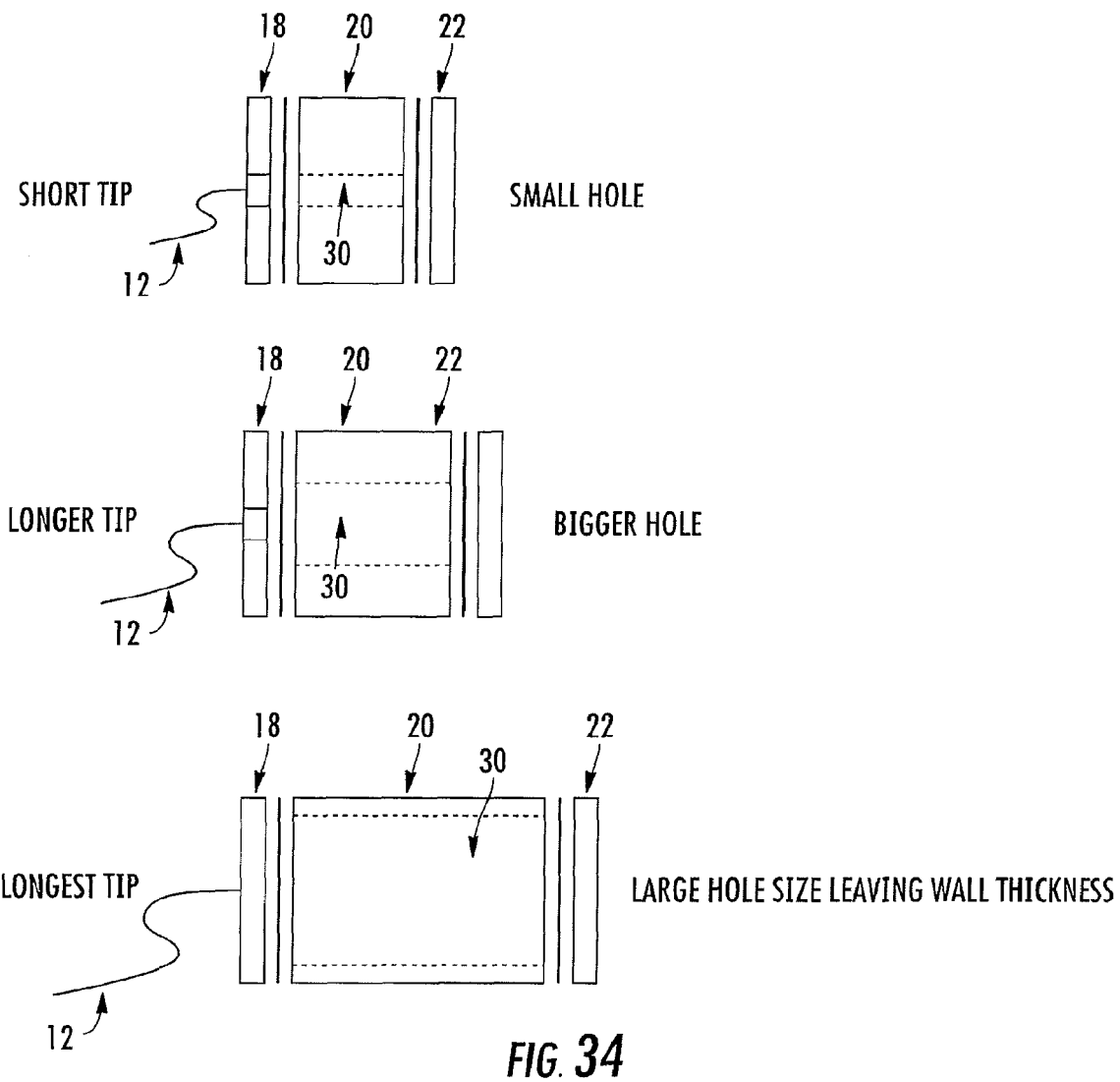
FIG. 34 illustrates several exemplary embodiments of diffusion tips.

FIG. 34 shows how the size of void 30 may be adjusted relative to the length of tip 10 in order to maintain a substantially uniform axial intensity distribution. In general, as the void size is increased, the length of the tip that can be used to provide uniform illumination is increased up to the point at which the wall thickness becomes extremely thin. Above that point, other properties of tip 10 (e.g. the curvature of one or more of the reflectors) must be adjusted to maintain uniform illumination.

Figure 35:
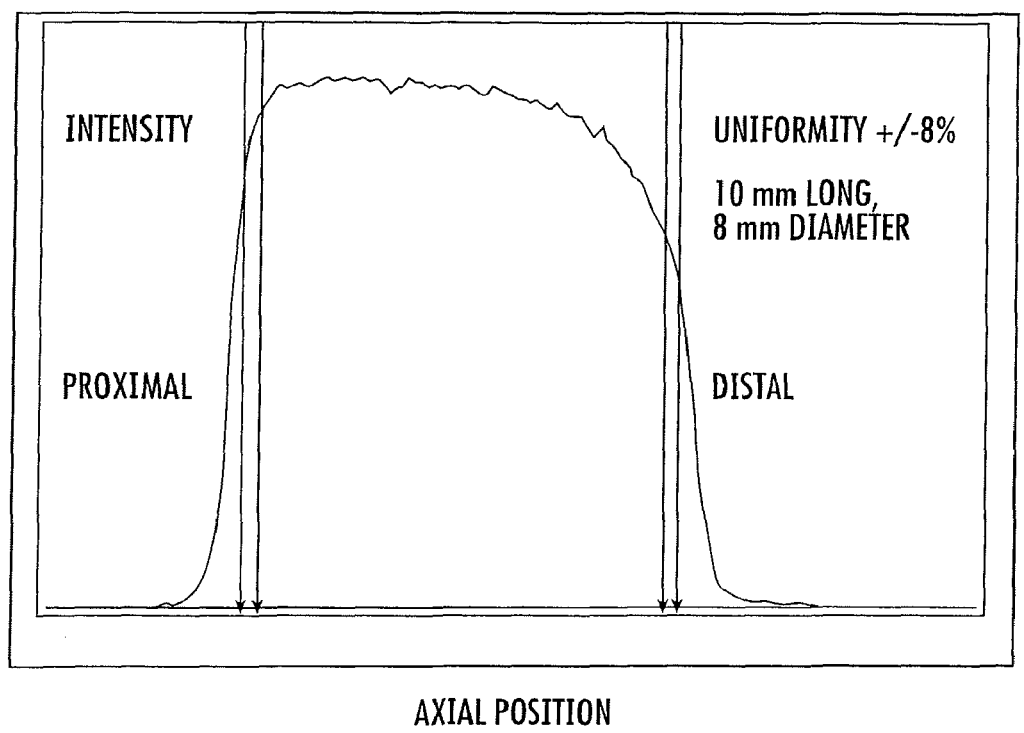
FIG. 35 is an intensity CCD camera scan of a diffusion tip.

FIG. 35 shows an intensity profile of a diffusion tip 10. Axial intensity distribution uniformity of +/−8% is achieved using the techniques taught herein. Note also the lack of any light outside the cavity region. This indicates that the cumulative illumination pattern for this tip is a substantially uniform cylindrical pattern characterized by uniform axial intensity distribution directed outward in the radial direction along diffusion tube 20 and substantially proscribed illumination in the axial direction.

Figure 36:
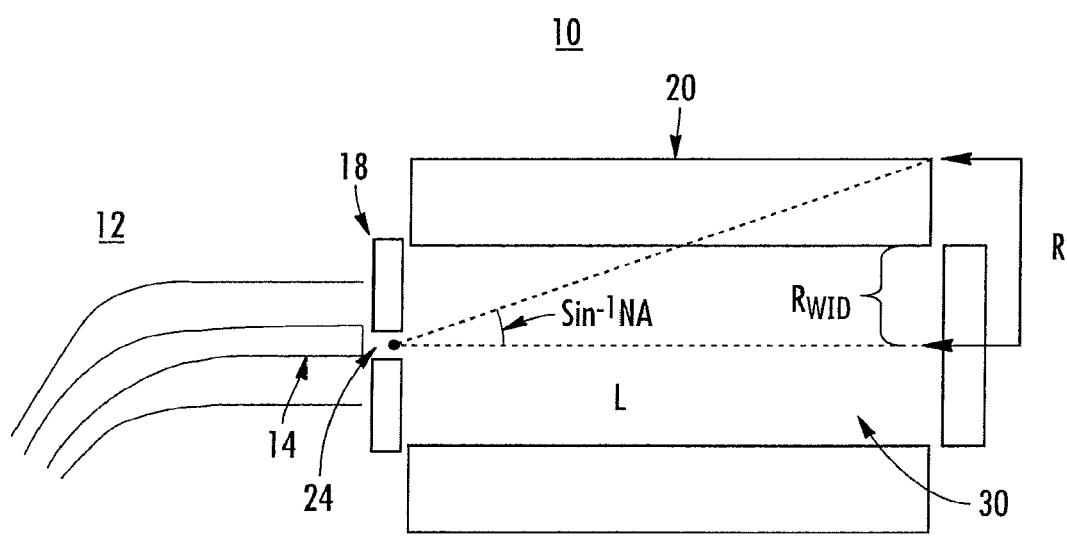
FIG. 36 is an illustration of a diffusion tip.

Referring to FIG. 36, in one embodiment, the preferred void size or preferred length for a given void size may be calculated as follows. Light from fiber 12 propagates radial outward in a cone from aperture 24 as defined by the numerical aperture NA and the length L of tube 20. The radius of this cone at the distal end of tube 20 is defined as R. The radius of void 30 is defined at $R_{void}$. In one embodiment, for uniform axial illumination, the area of the void is chosen to be chosen to be 40% of the area of the cone at the distal end of tube 20 such that $$R_{void} = 0.4\pi R^2 = (0.4 NAL)^(1/2) = 0.63 NAL.$$

Thus, for an embodiment where L=10 mm and NA=0.3, $R_{void}$ is about 1.89 mm. In an embodiment employing a standard 5/16 inch tube having a 3/16 inch void, L is equal to about one half inch. Thus, uniform intensity profiles may be obtained using easily obtainable components for diffusion tips have aspect rations on the order of 0.1 to 10.

In some embodiments, the fiber assembly elements are held together in a transparent tube, such as a heat shrink tubing. In one embodiment, the heat shrink tubing is a clear thin walled polyester tubing. In some embodiments, aluminum disks make convenient backing plates for both mirror assemblies.

Figure 37:
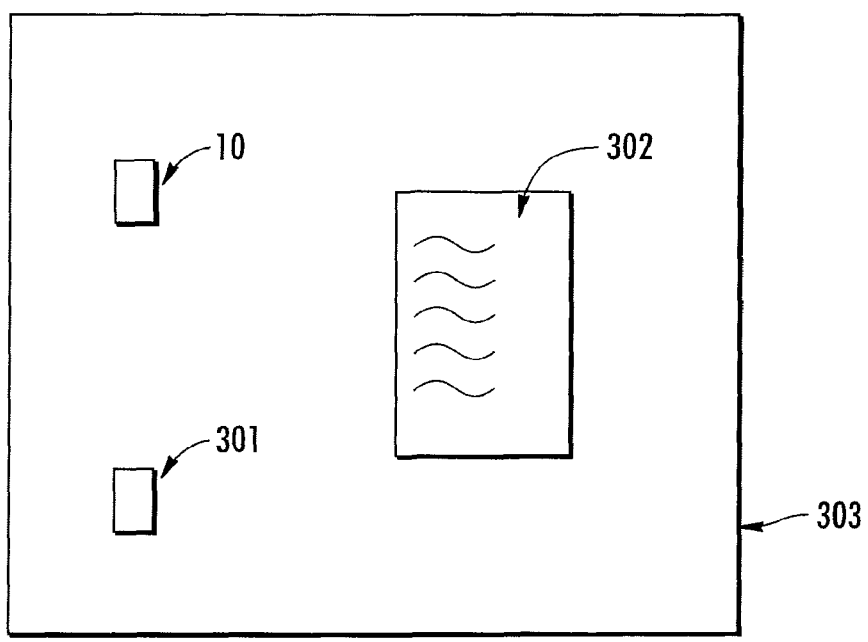
FIG. 37 is an illustration of a kit including a diffusion tip.

Referring to FIG. 37, a kit 300 includes a diffuser tip 10, e.g. of the types described herein, suitable for use with a treatment system of the type described above (e.g. system 110) to provide a desired distribution of treatment light at a target site. Tip 10 may be may be detachably connected to the treatment system and may be configured to apply therapeutic light at NIMELS dosimetry and wavelengths without becoming subject to unwanted levels of heating at treatment site.

Kit 300 also includes antimicrobial (e.g. antibiotic or antifungal) application 301 which is potentiated by treatment light delivered from the diffuser tip. As described in detail above, antimicrobial application 301 may be potentiated by the treatment light to treat a resistant biological contaminate at a treatment site even though the antimicrobial application alone would be ineffective in treating the contaminate. For example, in one embodiment, antimicrobial application 302 may be erythromycin potentiated by NIMELS treatment light to treat antibiotic resistant bacteria such as MRSA or MSSA. In various embodiments antimicrobial application 301 may be a topical application (e.g. a paste) or may be administered in other ways known in the art (e.g. ingested orally, administered intravenously, etc.)

Kit 300 may also include instructions 302 instructing the use of antimicrobial application 301 in conjunction with potentiating treatment light diffused by tip 10. The instructions may provide guidance as to the types of contaminates which may be treated using the kit, along with information regarding suitable dosimetry for the treatment light (e.g. NIMELS dosimetry). The instructions may be provided in any media including print or electronic formats.

The above described elements of Kit 300 may be contained in suitable packaging 303, e.g. a box or pouch. In some embodiments the packaging may include sterile packaging. For example, in some embodiments tip 10 may be sterilized and packed in a sterile container.

In various embodiments, diffusion tip 10 may include any number of sensors, e.g., temperature sensors which may communicate (by wire or wirelessly) with therapeutic system 110. Information provided by these sensors may be used to control applied dosages of therapeutic light, e.g. for safety purposes. Tip 10 may also include one or more cooling devices (e.g. a thermoelectric cooler), or attachments suitable for engagement with external cooling devices (e.g. tubular plumbing for circulation of cooling fluids).

It is to be understood that, as used herein, the phrases "light", "optical", etc. are not limited to the visible spectrum, but may refer to electromagnetic radiation at any wavelength including, e.g., the infrared.

While this invention has been particularly shown and described with references to example embodiments thereof, it will be understood by those skilled in the art that various changes in form and details may be made therein without departing from the scope of the invention encompassed by the appended claims.

What is claimed is:

1. An optical delivery apparatus comprising:
   an optical fiber extending between a distal end having a distal end face and a proximal end having a proximal end face, said fiber configured to receive light from at least one source at the proximal end face, transmit the light from the proximal end to the distal end, and emit the light from the distal end face; and
   an optical element positioned to receive the light emitted from the distal end face and direct the light to an illumination region;
   wherein the optical element comprises a diffuser tip assembly adapted to receive the distal end of optical fiber, the assembly comprising:
      a reflective cavity comprising:
         a first reflector positioned proximal the distal end of the received fiber and comprising an aperture adapted to admit light emitted from the fiber into the cavity; and
         a second reflector positioned distal the first reflector; and a diffuser tube positioned between the first and second reflectors about a cavity axis extending from the first reflector to the second reflector, the diffuser tube comprising an inner void surrounded by an outer portion comprising a diffusive scattering material;

wherein the cavity and diffuser tube are arranged such that at least a portion of light admitted into the cavity is scattered by the diffusive scattering material out of the tip assembly through the outer portion in a direction transverse to the cavity axis.

2. The apparatus of claim 1, wherein the cavity and diffuser tube are configured such that:

light admitted into the cavity is directed from the aperture towards the second reflector;

a portion of the light directed towards the second reflector impinges upon the diffusive scattering material and is scattered out of the tip assembly in a direction transverse to the axis; and at least a portion of unscattered light impinges upon the second reflector and is reflected back towards the first reflector; and a portion of the light directed back towards the first reflector impinges upon the diffusive scattering material and is scattered out of the tip assembly in a direction transverse to the axis.

3. The apparatus of claim 2, wherein the cavity and diffuser tube are configured such that light admitted into the cavity travels multiple passes between the first and second reflectors, and on each pass, at least a portion of the light is scattered by the diffusive scattering material out of the tip assembly m a direction transverse to the axis.

4. The apparatus of claim 3, wherein the light scattered out of the tip assembly on each pass combine to produce a cumulative illumination pattern.

5. The apparatus of claim 4, wherein the cumulative illumination pattern is characterized by substantially uniform axial intensity profile along at least a portion of the diffuser tube.

6. The apparatus of claim 5, wherein the cumulative illumination pattern is characterized by a substantially uniform azimuthal illumination profile.

7. The apparatus of claim 6, wherein the cumulative illumination pattern is characterized by substantially proscribed illumination in the direction parallel to the axis.

8. The diffuser tip assembly of any of claim 7, wherein the cumulative illumination pattern is a substantially uniform cylindrical illumination pattern emitted radially from the outer surface of the diffuser tube.

9. The apparatus of claim 8, wherein the cumulative illumination pattern is determined by at least on at least one chosen from the list consisting of a length of the diffuser tube, the diameter of the inner void of the diffuser tube, a numerical aperture associate with the aperture in the first reflector.

10. The apparatus of claim 1, wherein the inner void is filled with a substantially transparent non-scattering material.

11. The apparatus of claim 1, wherein the at least one of the first and second reflectors comprises a curved reflector.

12. The apparatus of claim 1, wherein the first reflector is a diffuse reflector and the second reflector is a specular reflector.

13. The apparatus of claim 1, wherein the ratio of the distance between the first reflector and the second reflector along the cavity axis to the outer diameter of the diffusion tube is about 10 or less.

14. The apparatus of claim 1, wherein the ratio of the distance between the first reflector and the second reflector along the cavity axis to the outer diameter of the diffusion tube is about 1 or less.

15. The apparatus of claim 1, wherein the ratio of the distance between the first reflector and the second reflector along the cavity axis to the outer diameter of the diffusion tube is about 0.1 or less.

16. The apparatus of claim 1, wherein the diffusive scattering material comprises at least one selected from the list consisting of a plastic, a glass, a polymer, and a fluid.

17. The apparatus of claim 1, wherein the diffusive scattering material comprises PTFE.

18. The apparatus of claim 1, further comprising a substantially transparent outer jacket adapted to contain the reflective cavity and the diffuser tube.

19. The apparatus of claim 1, wherein the diffusive scattering material is adapted to scatter light in the near infrared.

20. The apparatus of claim 1, wherein the tip assembly is adapted to scatter about 80% or more of the light delivered from the fiber while absorbing about 20% or less of the light delivered from the fiber.

* * * * *